United States Patent
Roti-Roti et al.

(10) Patent No.: US 12,258,630 B2
(45) Date of Patent: *Mar. 25, 2025

(54) METHODS AND SYSTEMS FOR ASSESSING AND/OR QUANTIFYING SPERM CELL SUBPOPULATIONS BEARING A SPECIFIC GENETIC SIGNATURE

(71) Applicant: Genus plc, Basingstoke (GB)

(72) Inventors: Elon Roti-Roti, Windsor, WI (US); Nicole Cray, Madison, WI (US); Matthias Wagner, Cambridge, MA (US); Michael Reid Botts, DeForest, WI (US)

(73) Assignee: ABS Global, Inc., DeForest, WI (US)

( * ) Notice: Subject to any disclaimer, the term of this patent is extended or adjusted under 35 U.S.C. 154(b) by 1011 days.

This patent is subject to a terminal disclaimer.

(21) Appl. No.: 17/178,806

(22) Filed: Feb. 18, 2021

(65) Prior Publication Data

US 2021/0189488 A1 Jun. 24, 2021

Related U.S. Application Data

(63) Continuation of application No. 16/121,077, filed on Sep. 4, 2018, now Pat. No. 10,961,577.

(60) Provisional application No. 62/553,771, filed on Sep. 1, 2017.

(51) Int. Cl.
*C12Q 1/6879* (2018.01)
*C12Q 1/6841* (2018.01)

(52) U.S. Cl.
CPC ......... *C12Q 1/6879* (2013.01); *C12Q 1/6841* (2013.01); *C12Q 2600/124* (2013.01); *C12Q 2600/16* (2013.01); *C12Q 2600/166* (2013.01)

(58) Field of Classification Search
CPC ..... C12Q 1/68; C12Q 2600/124; C07H 21/00
See application file for complete search history.

(56) References Cited

U.S. PATENT DOCUMENTS

| | | |
|---|---|---|
| 3,687,803 A | 8/1972 | Grayson et al. |
| 3,894,529 A | 7/1975 | Shrimpton et al. |
| 4,009,260 A | 2/1977 | Ericsson |
| 4,067,965 A | 1/1978 | Bhattacharya |
| 4,083,957 A | 4/1978 | Lang |
| 4,085,205 A | 4/1978 | Hancock |
| 4,092,229 A | 5/1978 | Bhattacharya |
| 4,155,831 A | 5/1979 | Bhattacharya |
| 4,191,749 A | 3/1980 | Bryant |
| 4,225,405 A | 9/1980 | Lawson |
| 4,276,139 A | 6/1981 | Lawson |
| 4,339,434 A | 7/1982 | Ericsson |
| 4,448,767 A | 5/1984 | Bryant |
| 4,511,661 A | 4/1985 | Goldberg |
| RE32,350 E | 2/1987 | Bhattacharya et al. |
| 4,680,258 A | 7/1987 | Hammerling et al. |
| 4,683,195 A | 7/1987 | Mullis et al. |
| 4,683,202 A | 7/1987 | Mullis |
| 4,698,142 A | 10/1987 | Muroi et al. |
| 4,749,458 A | 6/1988 | Muroi et al. |
| 4,988,167 A | 1/1991 | Fergason |
| 4,999,283 A | 3/1991 | Zavos et al. |
| 5,021,244 A | 6/1991 | Spaulding |
| 5,135,759 A | 8/1992 | Johnson |
| 5,346,990 A | 9/1994 | Spaulding |
| 5,439,362 A | 8/1995 | Spaulding |
| 5,459,038 A | 10/1995 | Reed |
| 5,514,537 A | 5/1996 | Chandler |
| 5,596,089 A | 1/1997 | Silversides |
| 5,660,997 A | 8/1997 | Spaulding |
| 6,149,867 A | 11/2000 | Seidel |
| 8,858,943 B2 | 10/2014 | Burbidge |
| 9,588,100 B2 | 3/2017 | Appleyard et al. |
| 9,683,922 B2 | 6/2017 | Wagner et al. |
| 10,208,350 B2 | 2/2019 | Beim |
| 10,961,577 B2 * | 3/2021 | Roti-Roti ............. C12Q 1/6879 |
| 2004/0049801 A1 | 3/2004 | Seidel |
| 2004/0053243 A1 | 3/2004 | Evans |
| 2005/0130115 A1 | 6/2005 | Funk |
| 2009/0087847 A1 | 4/2009 | Lo |
| 2009/0227606 A1 | 9/2009 | DeLeo |
| 2010/0029498 A1 * | 2/2010 | Gnirke ................. C12Q 1/6811 506/9 |
| 2010/0260670 A1 | 10/2010 | Zeiger |

(Continued)

FOREIGN PATENT DOCUMENTS

| | | |
|---|---|---|
| EP | 3323828 | 5/2018 |
| KR | 2017 0008181 A | 1/2017 |

(Continued)

OTHER PUBLICATIONS

Aasen et al., Amplification of ZFY and ZFX genes for sex determination in humans, cattle, sheep and goats. Biotechnology 8:1279. (1990).
Ali et al., Enrich. of Bovine X-and Y-Chrom-Bearing Sperm with Monoclonal H-Y Antibody-Fluorescence-Activated Cell Sorter. Archives of Andrology 24:235 (1990).
Bilal et al., Buffalo : Black gold of Pakistan. Livestock Research for rural development 18(9) (2006).
Canavez et al., Genome sequence and assembly of Bos indicus. J. of Heredity 103(3) : 342 (2012).
Enciso et al., The ability of sperm selection techniques to remove single—or double-strand DNA damage. Asian J. of Andrology 13: 764-768 (2011).
Fernandez et al., The Effect of Low-Level Laser Irradiation on Sperm Motility, and Integrity of the Plasma Membrane and Acrosome in Cryopreserved Bovine Sperm. Plos One | DOI: 10.1371 Journal. pone.0121487 (Mar. 2015) 11 pgs., (2015).

(Continued)

*Primary Examiner* — Ethan C Whisenant
(74) *Attorney, Agent, or Firm* — Christopher J. Arnold; Daniel M. Lorentzen

(57) ABSTRACT

Technologies for assessing, quantifying and isolating sperm cell populations and/or subpopulations having specific genetic signatures are provided, as well as methods and systems to assess the efficacy of chromosomal differentiation processes. Compositions for identification and differentiation of X-chromosomes and Y-chromosomes in DNA are also provided.

20 Claims, 17 Drawing Sheets

Specification includes a Sequence Listing.

(56) References Cited

U.S. PATENT DOCUMENTS

| | | | |
|---|---|---|---|
| 2014/0182005 A1 | 6/2014 | Oksenberg | |
| 2014/0275219 A1 | 9/2014 | Cao | |
| 2016/0223442 A1* | 8/2016 | Guldberg | C12N 15/1017 |
| 2017/0204370 A1 | 3/2017 | Morjal et al. | |
| 2017/0226594 A1* | 8/2017 | Altayari | C12Q 1/6844 |
| 2019/0025212 A1 | 1/2019 | Evans | |

FOREIGN PATENT DOCUMENTS

| | | |
|---|---|---|
| WO | WO 95/11995 | 5/1995 |
| WO | WO 99/33956 | 7/1999 |
| WO | WO 00/06193 | 2/2000 |

OTHER PUBLICATIONS

Gravitt et al., Reproducibility of HPV 16 and HPV 18 viral load quantitation using TaqMan real-time PCR assays. J. of Virologicall Methods 112:233-33 (2003).
Johnson et al., Sex Preselection in Rabbits : Live Births from X and Y Sperm separated by DNA and cell sorting. Biology of Reproduction 41:199-203 (1989).
Kierstein et al., Analysis of mitochondrial D-loop region casts new light on domestic water buffalo (Bubalus bubalis) phylogeny. Molecular Phylogenetics and Evolution 30:308-324 (2004).
Liu et al. Bos taurus genome assembly. BMC Genomics 10:180 (2009).
Lun et al., Microfluidics Digital PCR Reveals a Higher than Expected Fraction of Fetal DNA in Maternal Plasma. Clinical Chemistry 54(10): 1664 (2008).
Peipo et al., Birth of Correctly Genotyped Calves After Multiplex Marker Detection From Bovine Embryo Microblade Biopsies. Molecular Reproduction and Development 74: 1373-1378 (2007).
Pruitt et al., NCBI reference sequences (RefSeq): a curated non-redundant sequence database of genomes, transcripts and proteins. Nucleic Acids Research 35: Database Issue D61-D65 (2007).
Rychlik et al., A computer program for choosing optimal oligonucleotides for filter hybridization, sequencing and in vitro amplification of DNA. Nucleic Acids Research 17(21) : 8543 (1989).
Schneider-Gadicke et al., ZFX has a gene structure similar to ZFY, the putative human sex determinant, and escapes X inactivation. Cell 57 : 1247 (1989).
Thellin et al. Housekeeping genes as internal standards: use and limits. J. of Biotechnology 75:291 (1999).
Vitra et al., Sex determination of bovine embryo blastomeres by fluorogenic probes. Theriogenology 57: 2229-2236 (2002).
Welch et al., Flow cytometic sperm sorting and PCR confirm separation of X- and Y-chromosome bearing bovine sperm. Animal Biotechnology 6(2) : 131-139 (2009).
Kirkpatrick et al., Sensitive sex determination assay applicable to bovine embryos derived from IVM and Ivf. J. of Reproduction and Fertility 98 : 335 (1993).
Zimin et al., A whole-genome assembly of the domestic cow, Bos taurus. Genome Biology 10:R42 (2009).
Floren et al., Species identification and quantification in meat and meat products using droplet digital PCR (ddPCR). Food Chemistry 173:1054-1058 (2015).
Kirkness et al., The Dog Genome : Survey Sequencing and comparative Analysis. Science 301 : 1898 (2003).
Nielsen et al., A Scan for Positively Selected Genes in the Genomes of Humans and Chimpanzees. PLoS Biology 3 (6) :e170 (2005).
Smith et al., Sequence Evaluation of Four Pooled-Tissue Normalized Bovine cDNA Libraries and Construction of a Gene Index for Cattle. Genome Research 11: 626 (2001).
Yu et al., Multiplex picoliter-droplet digital PCR for quantitative assessment of EGFR mutations in circulating cell-free DNA derived from advanced non-small cell lung cancer patients. Molecular Medicine Reports 16:1157 (Jun. 2017) (2017).

Helton et al., Selection and use of SNP markers for animal identification and paternity analysis in U.S. beef cattle. Mammalian Genome 13:272-281 (2002).
Smith et al., Sequence Evaluation of Four Pooled-Tissue Normalized Bovine cDNA Libraries and Construction of a Gene Index for Cattle. Genome Research 11: 626-630 (2001).
International Search Report and Written Opinion of the International Searching Authority dated Dec. 10, 2018; International Appln. No. PCT/IB2018/056710, Filed Sept. 3, 2018, Applicant: Genus plc.
U.S. Appl. No. 60/211,093, filed Jun. 12, 2000, Whittier et al.
U.S. Appl. No. 60/224,050, filed Aug. 9, 2000, Whittier et al.
U.S. Appl. No. 60/253,785, filed Nov. 29, 2000, Seidel et al.
Borchersen et al., "Danish A.I. field data with sexed semen," Theriogenology, 71(1):59-63 (2009).
Cerchiaro et al., "A field Study on fetility and purity of sex-sorted cattle sperm.," J Dairy Sci, 90(5):2538-2542 (2007).
Chen et al., "Single nucleotide poiymorphism genotyping: biochemistry, protocol, cost and throughput" Pharmacogenomis J., 3(2):77-96 (2003).
De Risi et al., "Use of a cDNA microarry to analyse gene expression patterns in human cancer." Nature Genetics, 14:457-460 (1996).
Deiahunty et al., "Testing the Feasibility of DNA Typing for Human Identification by PCR and an Oligonucleotide Ligation Assay," Am J Hum Genet, 58:1239-4246 (1996).
Egholm, et al., "PNA hybridizes to complementary oligonucleotides obeyign the Watson-Crick hydrogen-bonding rules," Nature, 365:566-568 (1993).
Faust et al., "1133 Effects for fertility of processing steps of a new technology platform for producing sexed sperm" Journal of Animal Sciences, 94(suppl_5):544-544 (2016).
Habermann et al., "Validation of sperm sexing in the cattle (Bos taurus) by dual colour fluorescence in situ hybridization," J Anim Breed Genet, 122 Suppl 1:22-27 (2005).
Hacia et al., "Detection of heterozygous mutations in BRCA1 using high density oligonucleotide arrays and two-colour fluoresence analysis," Nature Genetics, 14:441-447 (1996).
Healy et al., "Artificial insemination field data on the use of sexed and conventional semen in nulliparous Holstein heifers," J Dairy Sci, 96(3):1905-1914 (2013).
Hindson et al., "High-throughput droplet digital PCR system fo absolute quantitation of DNA copy number," Anal Chem, 83(22): 8604-8610 (2011).
International Search Report mail on Dec. 10, 2018, in Internationai Patent Application No. PCT/IB2018/056710.
Joerg et al., "Validating bovine sexed semen samples using quantitative PCR," J Anim Breed Genet, 121(3):209-215 (2004).
Johnson et al., "Sex preselection: high-speed flow cytometric sorting of X and Y sperm for maximum eficiency" Theriogenology, 52(8):1323-1341 (1999).
Johnson, "Sex preselection by flow cytometric separation of X and Y chromosome-bearing sperm based on DNA difference: a review," Reprod Fertil Dev, 7(4):893-903 (1995).
Kawarasaki et al., "Verification of flow cytometorically-sorted X- and Y- bearing porcine spermatozoa and reanalysis of spermatozoa for DNA content using the floresence in situ hybridization (FISH) technique," Theriogenology50(4):625-635 (1998).
Khalajzadeh et al., "Effect of widespread and limited use of sexed semen on genetic progress and reproductive performance of dairy cows," Animal, 6(9):1398-1406 (2012).
Khamlor et al., "Determination of Sperm Sex Ratio in Bovine Semen Using Multiplex Real-time Polymerase Chain Reaction," Asian-Australas J Anim Sci, 27(10):1411-1416 (2014).
Kwok et al., "Detection of single nucleotide polymorphisms," Curr Issues Mol Biol, 5(2):43-60 (2003).
Kwok, "Methods for genotyping single nucleotide polymorphisms," Annu Rev Genomics Hum Genet, 2:235-58 (2001).
Lalande et al., "Quantitative studies on the precursors of cytotoxic lymphocytes, VI. Second signal requirements of specifically activated precursors isolate 12 h after stimulation," The Journal of Experimental Medicine, 151(1):12-19 (1980).
Lalande et al., "Fluorescence flow analysis of lymphocyte activation using Hoechst 33342 dye," The Journal of Histochemistry and Cytochemistry, 27(1):394-397 (1979).

(56) References Cited

OTHER PUBLICATIONS

Lockhart et al., "Expression monitoring by hybridization to high-density oligonucleotide arrays," *Nature Biotechnol.*, 14:1675-1680 (1996).

Loken, "Separation of viable T and B lymphocytes using a cytochemical stain, Hoechst 33342," *The Journal of Histochemistry and Cytochemistry*, 28(1):36-39 (1980).

Loken, "Simultaneous Quantitation of Hoechst 33342 and Immunofluorescence on Viable Cells using a Fluorescence Activated Cell Sorter," *Cytometry*, 1(2):136-142. (1980).

Mateizel et al., "FISH analysis of chromosome X, Y and 18 abnormalities in testicular sperm from azoospermic patients," *Hum Reprod*, 17(9):2249-57 (2002).

Moruzzi, "Selecting a mammalian species for the separation of X- and Y-chromosome-bearing spermatozoa," *J Reprod Fertil*, 57(2):319-323 (1979).

Norman et al., "Use of sexed semen and its effect on conception rate, calf sex, dystocia, and stillbirth of Holsteins in the United States," *J Dairy Sci*, 93(8):3880-3890 (2010).

Ørum et al., "Single base pair mutation analysis by PNA directed PCR clamping," *Nucleic Acids Res*, 21(23):5332-5336 (1993).

Parati et al., "Sex ratio determination in bovine semen: a new approach by quantitative real time PCR" *Theriogenology*, 66(9):2202-2209 (2006).

Puglisi et al., "In vitro fertilisation with frozen-thawed bovine sperm sexed by flow cytometry and validated for acuracy by real-time PCR" *Reproduction*, 132(3):519-526 (2006).

Ramsay, "DNA chips: State-of-the art," *Nat Biotech*, 16:4044 (1998).

Rens et al., "An X-Y paint set and sperm FISH protocol that can be used for validation of cattle sperm separation procedures," *Reproduction*, 121(4):541-546 (2001).

Riley et al., "A novel, rapid method for the isolation of terminal sequences from yeast artificial chromosome (YAC) clones," *Nucleic Acids Res*, 18:2887-2890 (1990).

Saiki et al., "Enzymatic amplification of beta-globin genomic sequences and restriction site analysis for diagnosis of sickle cell anemia," *Science*, 230:1350-1354 (1985).

Seidel, "Update on sexed semen technology in cattle," *Animal*, 8(S1):160-164 (2014).

Shi, "Technologies for individual genotyping: detection of genetic polymorphisms in drug targets and disease genes," *Am J Pharmacogenomics*, 2(3):197-205 (2002).

Smith et al., "Advantages and limitations of quantitative PCR (Q-PCR)-based approaches in microbial ecology," *FEMS Microbiol Ecol*, 67(1):6-20 (2009).

Uhlmann et al., "Antisense oligonucleotides: a new therapeutic principle," *Chem Rev*, 90(4):543-584 (1990).

Van Munster et al., "Difference in volume of X- and Y-chromosome-bearing bovine sperm heads matches difference in DNA content," *Cytometry*, 35(2):125-128 (1979).

* cited by examiner

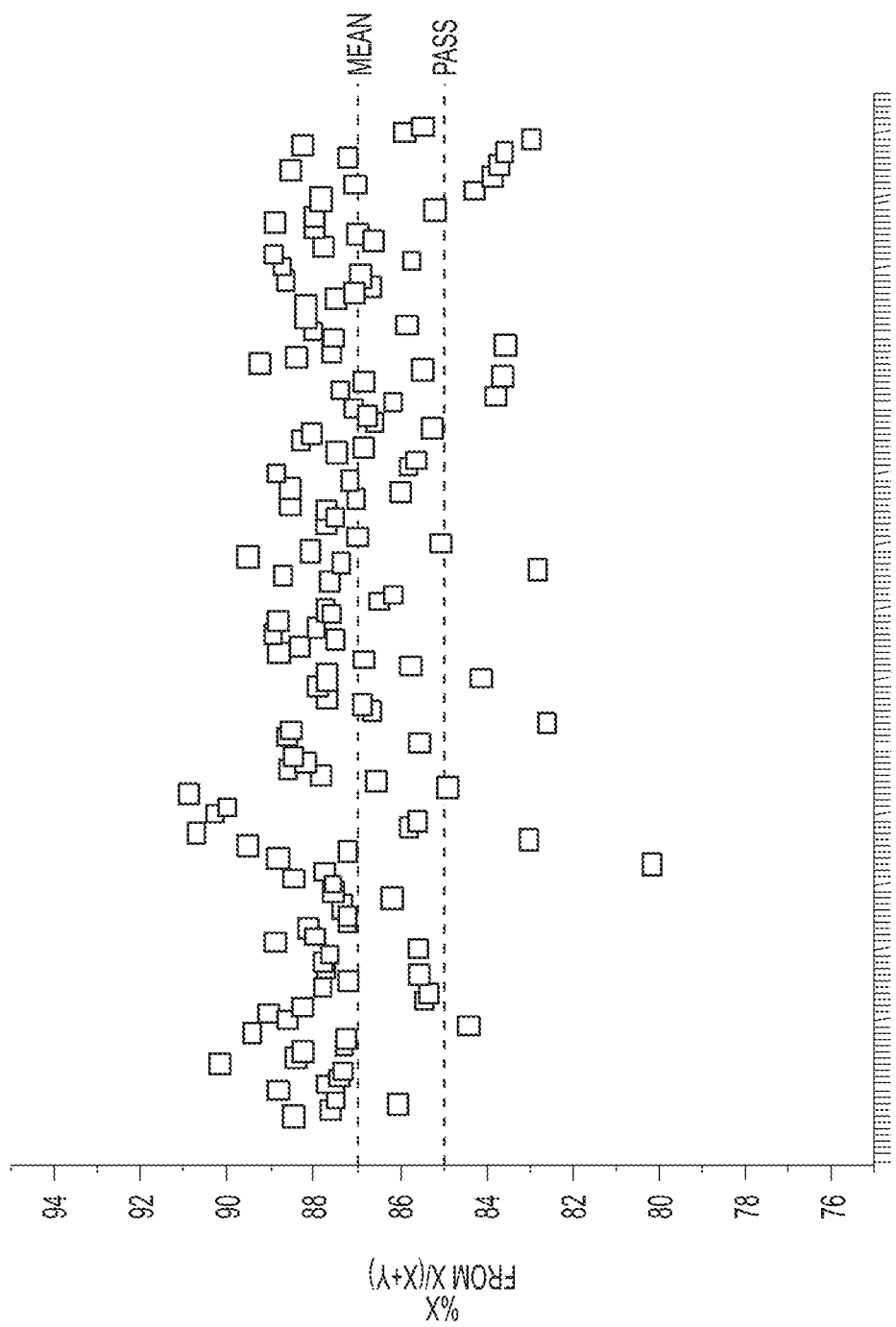

*FIG. 10* A-F

```
                        SEQUENCE LISTING

<160> NUMBER OF SEQ ID NOS: 900

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
agattgtcag gtgagcgcag                                              20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ccataagtcc ctccacgatg                                              20

<210> SEQ ID NO 3
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
caatgcctcc tgcaccacca ac                                           22

<210> SEQ ID NO 4
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
agagaagacc catgatgcaa agtcc                                        25

<210> SEQ ID NO 5
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
cctttcatag catccatgcc tcc                                          23
```

```
<210> SEQ ID NO 6
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
tcaacgatgg gagcacttta tgctgt                                              26

<210> SEQ ID NO 7
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ttaagccggt cacagtccg                                                      19

<210> SEQ ID NO 8
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gagataaaga gcgcctttgt tagcg                                               25

<210> SEQ ID NO 9
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
cgaaatccgt gtagccaatg ttac                                                24

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ccaaccgtga gaagatgacc                                                     20

<210> SEQ ID NO 11
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 11
gaacctgcaa agttccaaag gag                                              23

<210> SEQ ID NO 12
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gacgacatgg agaagatctg gc                                               22

<210> SEQ ID NO 13
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
tcagctcaga gaagaaagtc cta                                              23

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
agattgtcag gtgagcgcag                                                  20

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ccataagtcc ctccacgatg                                                  20

<210> SEQ ID NO 16
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
cagcatgaag atggccctg                                                   19

<210> SEQ ID NO 17
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 17
ggatgraggc actgggtgac                                                    20

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
tatgcttgcc cacggaagcc                                                    20

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gatcgttcag caatgcagcg                                                    20

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ctttctacct gctgtcccac g                                                  21

<210> SEQ ID NO 21
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
tacgcagcgg tttaataaca ttccc                                              25

<210> SEQ ID NO 22
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
tttgaacaga ctgatggttc cc                                                 22
```

<210> SEQ ID NO 23
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
caagaagtgt cacccctcgc                                                    20

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
gtaggcccct cagtacatgc                                                    20

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
tttctctcct cagtgacatc g                                                  21

<210> SEQ ID NO 26
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ttaaacaagt accaaacacc acgc                                               24

<210> SEQ ID NO 27
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
agcagccatt acgttgtctt cc                                                 22

<210> SEQ ID NO 28
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ttacctgaga aagaccat gatgc                          25

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
gagctttgta cagccttggg c                            21

<210> SEQ ID NO 30
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
gcacactcac taggagaaac aaacc                        25

<210> SEQ ID NO 31
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
tggaactgct cctcaaatct gc                           22

<210> SEQ ID NO 32
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gactcaagtc attgaagtct gctcc                        25

<210> SEQ ID NO 33
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
ctcctacagc ataaagtgct ccc                          23

<210> SEQ ID NO 34
<211> LENGTH: 25
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
agagaagacc catgatgcaa agtcc                                          25

<210> SEQ ID NO 35
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
cctttcatag catccatgcc tcc                                            23

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
aagcctgggc cacaataagg                                                20

<210> SEQ ID NO 37
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
aagagcgcct ttgttagcg                                                 19

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
attaagccgg tcacagtccg                                                20

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
aaagagcgcc tttgttagcg                                                20
```

```
<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gagcctggac tttcttgtgc                                               20

<210> SEQ ID NO 41
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ataaagagcg cctttgttag cg                                            22

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ttggctacac ggatttcggc                                               20

<210> SEQ ID NO 43
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
gataaagagc gcctttgtta gcg                                           23

<210> SEQ ID NO 44
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cattggctac acggatttcg g                                             21

<210> SEQ ID NO 45
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 45
gagataaaga gcgcctttgt tagcg        25

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
tactctcgct aacaaaggcg        20

<210> SEQ ID NO 47
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
tgaactcaag cagttttggt gc        22

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ttggctacac ggatttcggc        20

<210> SEQ ID NO 49
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
agagcgcctt tgttagcg        18

<210> SEQ ID NO 50
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
cttactctcg ctaacaaagg cg        22

<210> SEQ ID NO 51
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
gaactcaagc agttttggtg c                                              21

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ttactctcgc taacaaaggc g                                              21

<210> SEQ ID NO 53
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
aactcaagca gttttggtgc                                                20

<210> SEQ ID NO 54
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ttaagccggt cacagtccg                                                 19

<210> SEQ ID NO 55
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
gagataaaga gcgcctttgt tagcg                                          25

<210> SEQ ID NO 56
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (70)..(72)
```

<223> OTHER INFORMATION: a, c, t, g, unknown or other

<400> SEQUENCE: 56
ccaaccgtga aagatgacc caggtcagtg ggccgtcctg ccttgcctcc gcgcccctcc    60
tttcttgccn nnctttgcct cacccttctt    90

<210> SEQ ID NO 57
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ccaaccgtga aaaaatgacc caggtcagtg ggccgcccgg ccttgcctcc gcgcccctcc    60
tttcttgcct ttctttgcca cgcccttct    90

<210> SEQ ID NO 58
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (70)..(72)
<223> OTHER INFORMATION: a, c, t, g, unknown or other

<400> SEQUENCE: 58
ccaaccgtga aagatgacc caggtcagtg ggccgccctg ccttgcctcc gcgcccctcc    60
tttcttgccn nnctttgcct cacccttctt    90

<210> SEQ ID NO 59
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
cacttattct ctcttctgcc attttcctag gactttcttc tctgagctga gtctcctttg    60
gaactttgca ggttc    75

<210> SEQ ID NO 60
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
cacttattct ctcttctgcc atttccctag gactttcttc tctgagctga gtctcctttg    60
gaactctgca ggttc    75

<210> SEQ ID NO 61
<211> LENGTH: 75

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
cacttattct ctcttctgcc attttcctag gactttcttc tctgagctga gtctcctttg    60
gaactttgca ggttc                                                     75

<210> SEQ ID NO 62
<211> LENGTH: 243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (173)..(175)
<223> OTHER INFORMATION: a, c, t, g, unknown or other

<400> SEQUENCE: 62
gacgacatgg agaagatctg gcaccacacc ttctacaacg agctccgtgt ggcccctgag    60
gagcaccccg tgctgctgac cgaggccccc ctgaacccca aggccaaccg tgagaagatg   120
acccaggtca gtgggccgtc ctgccttgcc tccgcgcccc tcctttcttg ccnnnctttg   180 cctcacccctt tctcacttat tctctctcct gccattttcc taggactttc ttctctgagc   240
tga                                                                 243

<210> SEQ ID NO 63
<211> LENGTH: 243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63
gacgacatgg agaagatctg gcaccacacc ttctacaacg agctccgtgt ggcccctgag    60
gagcaccccg tgctgctgac cgaggccccc ctgaacccca aggccaaccg tgaaaagatg   120
acccaggtca gtgggccgcc cggccttgcc tccgcgcccc tcctttcttg cctttctttg   180 ccacgcccctt tctcacttat tctctctcct gccatttccc taggactttc ttctctgagc   240
tga                                                                 243

<210> SEQ ID NO 64
<211> LENGTH: 243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (173)..(175)
<223> OTHER INFORMATION: a, c, t, g, unknown or other

<400> SEQUENCE: 64
gacgacatgg agaagatctg gcaccacacc ttctacaacg agctccgtgt ggcccctgag    60
```

```
gagcaycccg tgctgctgac cgaggccccc ctgaacccca aggccaaccg tgagaagatg    120
acccaggtca gtgggccgcc ctgccttgcc tccgcgcccc tcctttcttg ccnnnctttg    180
cctcacccct tctcacttat tctctcttct gccattttcc taggactttc ttctctgagc    240
tga                                                                  243

<210> SEQ ID NO 65
<211> LENGTH: 185
<212> TYPE: DNA
<213> ORGANISM: Bos taurus

<400> SEQUENCE: 65
ccataagtcc ctccacgatg ccaaagtggt catggatgac cttggccagg ggggccaagc     60
agttggtggt gcaggaggca ttgctggaaa agagggaggc aagtcagggg cacgtccact    120
gggcaccagg gggcactatc agcccgcttc cccacctcct ctctgctgcg ctcacctgac    180
aatct                                                                185

<210> SEQ ID NO 66
<211> LENGTH: 185
<212> TYPE: DNA
<213> ORGANISM: Bubalus bubalis

<400> SEQUENCE: 66
ccataagtcc ctccacgatg ccaaagtggt catggatgac cttggccagg ggggccaagc     60
agttggtggt gcaggaggca ttgctggaaa agagggaggc aagtcagggg cacgtccact    120
gggcaccagg gggcactatc agcccgcttc cccacctcct ctctgctgcg ctcacctgac    180
aatct                                                                185

<210> SEQ ID NO 67
<211> LENGTH: 185
<212> TYPE: DNA
<213> ORGANISM: Bos indicus

<400> SEQUENCE: 67
ccataagtcc ctccacgatg ccaaagtggt catggatgac cttggccagg ggggccaagc     60
agttggtggt gcaggaggca ttgctggaaa agagggaggc aagtcagggg cacgtccact    120
gggcaccagg gggcactatc agcccgcttc cccacctcct ctctgctgcg ctcacctgac    180
aatct                                                                185

<210> SEQ ID NO 68
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: modified_base
<222> LOCATION: (223)..(224)
<223> OTHER INFORMATION: a, c, t, g, unknown or other

<400> SEQUENCE: 68
cagcatgaag atggccctga agatgatcca cagctggtgg gcatcactgc ccggaacatt     60
ccacgacaac cccagctggc tgctgagaac ctgggcatca gcctggccac cttgttgctg    120
```
aacaaaggag ccaagaacat cttggatgtt gcacggcagc tcaatgaagc ccactaattg    180
gtctgtgggg cacaggtgcc tgccttgctg gtcacccagt ngnncctrca tcc    233

<210> SEQ ID NO 69
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (214)..(214)
<223> OTHER INFORMATION: a, c, t, g, unknown or other

<400> SEQUENCE: 69
cagcatgaag atggccctga agatgatcca cagctggtgg gcatcactgc ccggaacatt    60
ccacgacaac cccagctggc tgctgagaac ctgggcatca gcctggccac cttgttgctg    120
aacaaaggag ccaagaacat cttggatgtt gcacggcagc tcaatgaagc ccactaattg    180
gtctgtgggg cacaggtgcc tgccttgctg gtgncccagt agtgcctaca tcc    233

<210> SEQ ID NO 70
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: modified_base
<222> LOCATION: (223)..(224)
<223> OTHER INFORMATION: a, c, t, g, unknown or other

<400> SEQUENCE: 70
cagcatgaag atggccctga agatgatcca cagctggtgg gcatcactgc ccggaacatt    60
ccacgacaac cccagctggc tgctgagaac ctgggcatca gcctggccac cttgttgctg    120
aacaaaggag ccaagaacat cttggatgtt gcacggcagc tcaatgaagc ccactaattg    180
gtctgtgggg cacaggtgcc tgccttgctg gtcacccagt ngnncctaca tcc    233

<210> SEQ ID NO 71
<211> LENGTH: 227
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
tatgcttgcc cacggaagcc atgtattgtt gtctcctcct tttgttttca accaagttct    60
gtcccttagc tccattggct ggggaaagat tggtactggt atcttaggct attttcccat    120 caggggggctc tgggtgtgga agttcgagcc aaagaccagg acatcttgga tctggtgggt    180
gtgttgcacg atcctgagac tctacttcgc tgcattgctg aacgatc    227

<210> SEQ ID NO 72

```
<211> LENGTH: 227
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (29)..(29)
<223> OTHER INFORMATION: a, c, t, g, unknown or other

<400> SEQUENCE: 72
tatgctcgac cacggaagcc atgtattgnt gtctcctcct tttgttttca accaagttct    60
gtcccttagc tccattggct ggggaaagat cggtactggt atcttaggct attttcccat   120 caggggctc tgggtgtgga agttcgagcc aaagaccagg acatcttgga tttggtgggt    180
gtgttgcacg atcctgagac tctacttcgc tgcattgctg aacgatc                 227

<210> SEQ ID NO 73
<211> LENGTH: 227
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
tatgcttgac cacggaagcc atgtattgtt gtctcctcct tttgttttca accaagttct    60
gtcccttagc tccattggct ggggaaagat tggtactggt atcttaggct attttcccat   120 caggggctc tgggtgtgga agttcgagcc aaagaccagg acatcttgga tctggtgggt    180
gtgttgcacg atcctgagac tctacttcgc tgcattgctg aacgatc                 227

<210> SEQ ID NO 74
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
ctttctacct gctgtcccac gctgagttca ctcccaacag caaggatcag tacagctgcc    60
gagtgaaaca cgttactttg gaacaacccc ggatagttaa gtggggtaag ttttcaagtt   120
ctttggttaa ccactgacag ttgtatctga gcacagctgc ggcatatagc tgctttgata   180
taaaaacgtc tgcatactgg gattatcagg gaatgtkatt aaacctctgc gta          233

<210> SEQ ID NO 75
<211> LENGTH: 92
<212> TYPE: DNA
<213> ORGANISM: Bubalus bubalis

<400> SEQUENCE: 75
ctttctacct gctgtcccac gctgagttca ctcccaacag caaggatcag tacagctgcc    60
gagtgaaaca cgttactttg gaacaacccc gg                                  92

<210> SEQ ID NO 76
<211> LENGTH: 233
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 76
ctttctacct gctgtcccac gctgagttca ctcccaacag caaggatcag tacagctgcc      60
gagtgaaaca cgttactttg gaacaacccc ggatagttaa gtggggtaag ttttcaagtt     120
ctttggttaa ccactgacag ttgtatctga gcacagctgc ggcatatagc tgctttgata    180
taamaacgtc tgcatactgg gattatcagg gaatgtkatt aaacctctgc rta            233

<210> SEQ ID NO 77
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
tttgaacaga ctgatggttc ccattagtca cataaagctg tagtcaagta cagacatcct      60
tagagctgga acttggccag gcgagggtga cacttcttg                             99

<210> SEQ ID NO 78
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
ttcgaacaga ctgatggttc ccattagtcg cataaagctg tagtcaagta cagacgtcct      60
tagagctgga acttggccag gcgagggtga cacttcttg                             99

<210> SEQ ID NO 79
<211> LENGTH: 99
<212> TYPE: DNA
<213> ORGANISM: Bos indicus

<400> SEQUENCE: 79
tttgaacaga ctgatggttc ccattagtca cataaagctg tagtcaagta cagacatcct      60
tagagctgga acttggccag gcgagggtga cacttcttg                             99

<210> SEQ ID NO 80
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
ttacctgaga gaagacccat gatgcaaagt cctaggacaa ggcctagaaa atcaacgatg      60
ggagcacttt atgctgtagg ag                                               82

<210> SEQ ID NO 81
<211> LENGTH: 82
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 81
ttacctgaga gaagacccat gatgcaaagt cctaggacaa ggcctagaaa atcaaccatg    60
ggagcacttt atgctgtagg ag    82

<210> SEQ ID NO 82
<211> LENGTH: 82
<212> TYPE: DNA
<213> ORGANISM: Bos indicus

<400> SEQUENCE: 82
ttacctgaga gaagacccat gatgcaaagt cctaggacaa ggcctagaaa atcaacgatg    60
ggagcacttt atgctgtagg ag    82

<210> SEQ ID NO 83
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83
gcacactcac taggagaaac aaaccatatt ctcacactta tgccccttc agactggcta    60 cacagcatgc tgaagacatg agtgttagca gatttgagga gcagttcca    109

<210> SEQ ID NO 84
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 84
gcacactcac taggagaaac aaaccatatt ctcacacttt tccccctttc agactggcta    60
cacagcatgc tgaagacatg agtgttagca gatttgagga gcagttcca    109

<210> SEQ ID NO 85
<211> LENGTH: 109
<212> TYPE: DNA
<213> ORGANISM: Bos indicus

<400> SEQUENCE: 85
gcacactcac taggagaaac aaaccatatt ctcacactta tgccccttc agactggcta    60 cacagcatgc tgaagacatg agtgttagca gatttgagga gcagttcca    109

<210> SEQ ID NO 86
<211> LENGTH: 106
<212> TYPE: DNA
<213> ORGANISM: Bos taurus

<400> SEQUENCE: 86
gactcaagtc attgaagtct gctccaattt tcttataaag cagctccacc cttcaaactg    60
cttagggatt ctatcatttg gagatgccca aggctgtaca aagctc    106

<210> SEQ ID NO 87
<211> LENGTH: 106
<212> TYPE: DNA
<213> ORGANISM: Bubalus bubalis

<400> SEQUENCE: 87
gactcaagtc attgaagtct gctccaattt tcttataaag cagctccacc cttcaaactg    60
cttagggatt ctatcatttg gagatgccca aggctgtaca aagctc                  106

<210> SEQ ID NO 88
<211> LENGTH: 106
<212> TYPE: DNA
<213> ORGANISM: Bos indicus

<400> SEQUENCE: 88
gactcaagtc attgaagtct gctccaattt tcttataaag cagctccacc cttcaaactg    60
cttagggatt ctatcatttg gagatgccca aggctgtaca aagctc                  106

<210> SEQ ID NO 89
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
agagaagacc catgatgcaa agtcctagga caaggcctag aaaatcaacg atgggagcac    60
tttatgctgt aggaggcatg gatgctatga aagg                                94

<210> SEQ ID NO 90
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
agagaagacc catgatgcaa agtcctagga caaggcctag aaaatcaacc atgggagcac    60
tttatgctgt aggaggcatg gatgctatga aagg                                94

<210> SEQ ID NO 91
<211> LENGTH: 94
<212> TYPE: DNA
<213> ORGANISM: Bos indicus

<400> SEQUENCE: 91
agagaagacc catgatgcaa agtcctagga caaggcctag aaaatcaacg atgggagcac    60
tttatgctgt aggaggcatg gatgctatga aagg                                94

<210> SEQ ID NO 92
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92

```
gaactcaagc agttttggtg ctgttaagat aattttttac aaaaaagtac tcttatagaa    60
agaactgatt aacagaggac cagttatatt ggaaagtctg aattctttac atgttaaatg   120
tacttactta ttgggcttct tataaaatta agtcgcaggt gaaactgtag taaaattgag   180
ataaagagcg cctttgttag cgagagtaag                                    210
```

<210> SEQ ID NO 93
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
gaactcaagc agttttggtg ctgttaagat aattttttac aaaaaagtac tcttacagaa    60
agaactgatt aacagaggac caattatatt ggaaagtctg aatcctttac atgttaaatg   120
tacttactta ttgggcttct tttaaaatta agtcgcaggt gaaattgtag taaaattgag   180
ataaagagtg cctttgagag cgagagtaag                                    210
```

<210> SEQ ID NO 94
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
gaactcaagc agttttggtg ctgttaagat aattttttac aaaaaagtac tcttatagaa    60
agaactgrtt aacagaggac cagttatatt ggaaagtctg aattctttac atgttaaatg   120
tacttactta ttgggcttct tataaaatta agtcgcaggt gaaactgtag taaaattgag   180
ataaagagcg cctttgttag cgagagtaag                                    210
```

<210> SEQ ID NO 95
<211> LENGTH: 208
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 95

```
ttactctcgc taacaaaggc gctctttatc tcaattttac tacagtttca cctgcgactt    60
aattttataa gaagcccaat aagtaagtac atttaacatg taaagaattc agactttcca   120
atataactgg tcctctgtta atcagttctt tctataagag tacttttttg taaaaaatta   180
tcttaacagc accaaaactg cttgagtt                                      208
```

<210> SEQ ID NO 96
<211> LENGTH: 208
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 96
ttactctcgc tctcaaaggc actctttatc tcaattttac tacaatttca cctgcgactt    60
aattttaaaa gaagcccaat aagtaagtac atttaacatg taaaggattc agactttcca    120
atataattgg tcctctgtta atcagttctt tctgtaagag tacttttttg taaaaaatta    180
tcttaacagc accaaaactg cttgagtt    208

<210> SEQ ID NO 97
<211> LENGTH: 208
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
ttactctcgc taacaaaggc gctctttatc tcaattttac tacagtttca cctgcgactt    60
aattttataa gaagcccaat aagtaagtac atttaacatg taaagaattc agactttcca    120
atataactgg tcctctgtta aycagttctt tctataagag tacttttttg taaaaaatta    180
tcttaacagc accaaaactg cttgagtt    208

<210> SEQ ID NO 98
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
aattcggcca gtgtcaggca ctagtattgg ttaagtgagg acgttttcct cgtagtgtcg    60
tcgacctgtt cggacccggt gttattccat tgtaaccgat gtgcctaaag ccgcctgaaa    120
gggacattgt tttcgaatct cggacctgaa agaacacgaa taaaagttat aactgaagga    180
atgagagcga ttgtttccgc gagaaataga g    211

<210> SEQ ID NO 99
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
aattcggcca gtgtcaggca ctagtattgg ttaagtgagg acgttttcct cgtagtgtcg    60
tcgacctgtt cggacccggt gttatcccat tgtaaccgat gtgcctaaag cctcctgaaa    120
gggatattgt tttcgaatct cggacctgaa agaacacgaa taaaagttat aactgaagga    180
atgagagcga gagtttccgt gagaaataga g    211

<210> SEQ ID NO 100
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 100

```
gagataaaga gcgcctttgt tagcgagagt aaggaagtca atattgaaaa taagcacaag    60
aaagtccagg ctctaagctt ttgttaaagg gaaagtccgc cgaaatccgt gtagccaatg   120
ttaccttatt gtgcccagg cttgtccagc tgctgtgatg ctcctttgc aggagtgaat    180
tggttatgat cacggactgt gaccggctta a                                   211
```

<210> SEQ ID NO 101
<211> LENGTH: 185
<212> TYPE: DNA
<213> ORGANISM: Bos taurus

<400> SEQUENCE: 101

```
agattgtcag gtgagcgcag cagagaggag gtggggaagc gggctgatag tgcccctgg     60
tgcccagtgg acgtgcccct gacttgcctc cctctttcc agcaatgcct cctgcaccac   120
caactgcttg gccccctgg ccaaggtcat ccatgaccac tttggcatcg tggagggact   180
tatgg                                                                185
```

<210> SEQ ID NO 102
<211> LENGTH: 185
<212> TYPE: DNA
<213> ORGANISM: Bubalus bubalis

<400> SEQUENCE: 102

```
agattgtcag gtgagcgcag cagagaggag gtggggaagc gggctgatag tgcccctgg     60
tgcccagtgg acgtgcccct gacttgcctc cctctttcc agcaatgcct cctgcaccac   120
caactgcttg gccccctgg ccaaggtcat ccatgaccac tttggcatcg tggagggact   180
tatgg                                                                185
```

<210> SEQ ID NO 103
<211> LENGTH: 185
<212> TYPE: DNA
<213> ORGANISM: Bos indicus

<400> SEQUENCE: 103

```
agattgtcag gtgagcgcag cagagaggag gtggggaagc gggctgatag tgcccctgg     60
tgcccagtgg acgtgcccct gacttgcctc cctctttcc agcaatgcct cctgcaccac   120
caactgcttg gccccctgg ccaaggtcat ccatgaccac tttggcatcg tggagggact   180
tatgg                                                                185
```

<210> SEQ ID NO 104
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104

```
ctcctgcgac ttcaacagcg acactcactc ttctaccttc gatgctgggg ctggcattgc     60
cctcaacgac cactttgtca agctcatttc ctggtatgtg gggggtgggg gtggggtgg   120
gatgatgctt cagcatgtgg tctggtgccc cctggtggct ggctcggtaa ac           172
```

```
<210> SEQ ID NO 105
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (113)..(118)
<223> OTHER INFORMATION: a, c, t, g, unknown or other

<400> SEQUENCE: 105
ctcctgcgac ttcaacagcg acactcactc ttctaccttc gatgctgggg ctggcattgc    60
cctcaacgac cactttgtca agctcatttc ctggtatgtg ggggntgggg gcnnnnnngg   120
gatgatgctt cagcatgtga tctggtgccc cctggtggct ggctcggtaa ac           172

<210> SEQ ID NO 106
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
ctcctgcgac ttcaacagcg acactcactc ttctaccttc gatgctgggg ctggcattgc    60
cctcaacgac cactttgtca agctcatttc ctggtatgtg ggggtgggg gtggggtgg    120 gatgatgctt cagcatgtgg tctggtgccc cctggtggct ggctcggtaa ac           172

<210> SEQ ID NO 107
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (111)..(112)
<223> OTHER INFORMATION: a, c, t, g, unknown or other

<400> SEQUENCE: 107
cgacaatgaa ttcggctaca gcaacagggt ggtggacctc atggtccaca tggcctccaa    60
ggagtaaggt ccctggaccc ccagcccag caggagcacg agaggaagag nnttcctcag   120
ctg                                                                  123

<210> SEQ ID NO 108
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108
cgacaatgaa ttcggctaca gcaacagggt ggtggacctc atggtccaca tggcctccaa    60
```
ggagtaaggt ccctggaccc tcagccccag caggagcatg agaggaagag agttcctccg    120
ctg                                                                 123

<210> SEQ ID NO 109
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (111)..(112)
<223> OTHER INFORMATION: a, c, t, g, unknown or other

<400> SEQUENCE: 109
cgacaatgaa tttggctaca gcaacagggt ggtggacctc atggtccaca tggcctccaa    60
ggagtaaggt ccctggaccc ccagccccag caggagcacg agaggaagag nnttcctcag   120
ctg                                                                 123

<210> SEQ ID NO 110
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gaagacccat gatgcaaagt cctaggacaa ggcctagaaa atcaacgatg ggagcacttt    60
atgctgtagg aggcatggat gctatgaaag g                                   91

<210> SEQ ID NO 111
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
gaagacccat gatgcaaagt cctaggacaa ggcctagaaa atcaaccatg ggagcacttt    60
atgctgtagg aggcatggat gctatgaaag g                                   91

<210> SEQ ID NO 112
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gaagacccat gatgcaaagt cctaggacaa ggcctagaaa atcaacgatg ggagcacttt    60
atgctgtagg aggcatggat gctatgaaag g                                   91

<210> SEQ ID NO 113
<211> LENGTH: 178
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (131)..(131)
<223> OTHER INFORMATION: a, c, t, g, unknown or other

<400> SEQUENCE: 113
gtggttggag gatatgatgg acatacttat ttgcacactg ttgaatcgta tgatgcacag    60
aaagatgaat ggagagaggt actcttaatt taagtatcca aattgatata tttcagggtt   120
taactcaaaa nttaaaatat atatttggaa ttcatcccat tctcttccac tctagggc    178

<210> SEQ ID NO 114
<211> LENGTH: 178
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
gtggttggag gatatgatgg acatacttat ttgaacactg ttgaatcgta tgatgcacag    60
aaagatgaat ggagagaggt actcttaatt taagtatcca aattgatata tttcaggttt   120
taactcaaaa attaaaatat atatttggaa ttcatcccat tctcttccac tctagggc    178

<210> SEQ ID NO 115
<211> LENGTH: 178
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (131)..(131)
<223> OTHER INFORMATION: a, c, t, g, unknown or other

<400> SEQUENCE: 115
gtggttggag gatatgatgg acatacttat ttgcacactg ttgaatcgta tgatgcacag    60
aaagatgaat ggagagaggt actcttaatt taagtatcca aattgatata tttcagggtt   120
taactcaaaa nttaaaatat atatttggaa ttcatcccat tctcttccac tctagggc    178

<210> SEQ ID NO 116
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (114)..(118)
<223> OTHER INFORMATION: a, c, t, g, unknown or other

<400> SEQUENCE: 116
gcacagaaag atgaatggag agaggtactc ttaatttaag tatccaaatt gatatatttc    60
```

-continued agggtttaac tcaaaantta aaatatatat ttggaattca tcccattctc ttcnnnnnta    120
gggctgaatc aaattacttt agtg                                           144

<210> SEQ ID NO 117
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
gcacagaaag atgaatggag agaggtactc ttaatttaag tatccaaatt gatatatttc    60
aggttttaac tcaaaaatta aaatatatat ttggaattca tcccattctc ttccactcta   120
gggctgaatc aaattacttt agtg                                           144

<210> SEQ ID NO 118
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (114)..(118)
<223> OTHER INFORMATION: a, c, t, g, unknown or other

<400> SEQUENCE: 118
gcacagaaag atgaatggag agaggtactc ttaatttaag tatccaaatt gatatatttc    60
agggtttaac tcaaaantta aaatatatat ttggaattca tcccattctc ttcnnnnnta   120
gggctgaatc aaattacttt agtg                                           144

<210> SEQ ID NO 119
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 119
gcacactcac taggagaaac aaaccatatt ctcacactta tgcccctttc agactggcta    60
cacagcatgc tgaagacatg agtgttagca gatttgagga gcagttcca               109

<210> SEQ ID NO 120
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
gcacactcac taggagaaac aaaccatatt ctcacacttt tccccctttc agactggcta    60
cacagcatgc tgaagacatg agtgttagca gatttgagga gcagttcca               109

<210> SEQ ID NO 121
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
gcacactcac taggagaaac aaaccatatt ctcacactta tgcccctttc agactggcta    60
cacagcatgc tgaagacatg agtgttagca gatttgagga gcagttcca              109

<210> SEQ ID NO 122
<211> LENGTH: 89
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
cagtgatgcc tcccatgtca acacacaggc atggtttagg taagagctta atgttgtata    60
gtttctaaag actgtacatt tactagagc                                    89

<210> SEQ ID NO 123
<211> LENGTH: 89
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
cagtgatgcc tcccatgtca acacacaggc atggtttagg taagagctta atgttgtata    60
gtttctaaag actgtgcatt tactagagc                                    89

<210> SEQ ID NO 124
<211> LENGTH: 89
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
cagtgatgcc tcccatgtca acacacaggc atggtttagg taagagctta atgttgtata    60
gtttctaaag actgtacatt tactagagc                                    89

<210> SEQ ID NO 125
<211> LENGTH: 83
<212> TYPE: DNA
<213> ORGANISM: Bos taurus

<400> SEQUENCE: 125
ggcatgatgt gcaggctagg caacaagacc tagcaatgct gctttcttac atcagattgc    60
cgttacttcc accacaggta tgg                                          83

<210> SEQ ID NO 126

```
<211> LENGTH: 83
<212> TYPE: DNA
<213> ORGANISM: Bubalus bubalis

<400> SEQUENCE: 126
ggcatgatgt gcaggctagg caacaagacc tagcaatgct gctttcttac atcagattgc    60
cgttacttcc accacaggta tgg                                            83

<210> SEQ ID NO 127
<211> LENGTH: 83
<212> TYPE: DNA
<213> ORGANISM: Bos indicus

<400> SEQUENCE: 127
ggcatgatgt gcaggctagg caacaagacc tagcaatgct gctttcttac atcagattgc    60
cgttacttcc accacaggta tgg                                            83

<210> SEQ ID NO 128
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 128
ttaagccggt cacagtccgt gatcataacc aattcactcc tgcaaaagga gcatcacagc    60
agctggacaa gcctgggcca caataaggta acattggcta cacggatttc ggcggacttt   120
ccctktaaca aaagcttaga gcctggactt tcttgtgctt attttcaata ttgacttcct   180
tactctcgct aacaaaggcg ctctttatct c                                  211

<210> SEQ ID NO 129
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129
ttaagccggt cacagtccgt gatcataacc aattcactcc tgcaaaagga gcatcacagc    60
agctggacaa gcctgggcca caatagggta acattggcta cacggatttc ggaggacttt   120
ccctttaaca aaagcttaga gcctggactt tcttgtgctt attttcaata ttgacttcct   180
tactctcgct ctcaaaggca ctctttatct c                                  211

<210> SEQ ID NO 130
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
ttaagccggt cacagtccgt gatcataacc aattcactcc tgcaaaagga gcatcacagc    60
agctggacaa gcctgggcca caataaggta acattggcta cacggatttc ggcggacttt   120
ccctttaaca aaagcttaga gcctggactt tcttgtgctt attttcaata ttgacttcct   180
```
tactctcgct aacaaaggcg ctctttatct c                                   211

<210> SEQ ID NO 131
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
cctgggccac aataaggtaa cattggctac acggatttcg gcggactttc cctgtaacaa    60
aagcttagag cctggacttt cttgtgctta ttttcaatat tgacttcctt actctcgcta   120
acaaaggcgc                                                          130

<210> SEQ ID NO 132
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132
cctgggccac aatagggtaa cattggctac acggatttcg gaggactttc cctttaacaa    60
aagcttagag cctggacttt cttgtgctta ttttcaatat tgacttcctt actctcgctc   120
tcaaaggcac                                                          130

<210> SEQ ID NO 133
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133
cctgggccac aataaggtaa cattggctac acggatttcg gcggactttc cctttaacaa    60
aagcttagag cctggacttt cttgtgctta ttttcaatat tgacttcctt actctcgcta   120
acaaaggcgc                                                          130

<210> SEQ ID NO 134
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
cttactctcg ctaacaaagg cgctctttat ctcaatttta ctacagtttc acctgcgact    60 taatttata agaagcccaa taagtaagta catttaacat gtaaagaatt cagactttcc   120
aatataactg gtcctctgtt aatcagttct ttctataaga gtactttttt gtaaaaaatt   180
atcttaacag caccaaaact gcttgagttc                                    210

<210> SEQ ID NO 135

```
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135
cttactctcg ctctcaaagg cactctttat ctcaattta ctacaatttc acctgcgact      60 taatttaaa agaagcccaa taagtaagta catttaacat gtaaaggatt cagactttcc    120
aatataattg gtcctctgtt aatcagttct ttctgtaaga gtactttttt gtaaaaaatt    180
atcttaacag caccaaaact gcttgagttc                                     210

<210> SEQ ID NO 136
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136
cttactctcg ctaacaaagg cgctctttat ctcaattta ctacagtttc acctgcgact      60 taatttata agaagcccaa taagtaagta catttaacat gtaaagaatt cagactttcc    120
aatataactg gtcctctgtt aaycagttct ttctataaga gtactttttt gtaaaaaatt    180
atcttaacag caccaaaact gcttgagttc                                     210

<210> SEQ ID NO 137
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 137
cagtgcagtc gtatgcttct gctatgttca gagtattgaa cgacgatgtt tacagtccag     60
ctgtggtaca gcaacaaact actctcgctt ttaggaaaga ctcttccttg tgcacagac    119

<210> SEQ ID NO 138
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 138
cagtgcagtc gtatgcttct gctatgttca gagtattgaa cgacgatgtt tacagtccag     60
cggtggtaca gcaacaaaat attctcgctt ttaggaaaga ctcttcctcg tgcacagac    119

<210> SEQ ID NO 139
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 139
cagtgcagtc gtatgcttct gctatgttca gagtattgaa cgacgatgtt tacagtccag    60
ctgtggtaca gcaacaaact actctcgctt ttaggaaaga ctcttccttg tgcacagac    119

<210> SEQ ID NO 140
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
caccgcatat tacttcctcc cctttttaaac agtgcagtcg tatgcttctg ctatgttcag    60
agtattgaac gacgatgttt acagtc    86

<210> SEQ ID NO 141
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
caccgcatat tatttcctcc tcttttaaac agtgcagtcg tatgcttctg ctatgttcag    60
agtattgaac gacgatgttt acagtc    86

<210> SEQ ID NO 142
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
caccgcatat tacttcctcc cctttttaaac agtgcagtcg tatgcttctg ctatgttcag    60
agtattgaac gacgatgttt acagtc    86

<210> SEQ ID NO 143
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gattgtttga gtaggaccac atattggtca tcttggtatg tccagttcct ggaaagtaaa    60
atattaataa cactgaggac gtggtacctg tg    92

<210> SEQ ID NO 144
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 144
gattgtttga gcaggaccac atattggtca tcttggtatg tccagttcct ggaaaataaa      60
atattaataa cactgaggac gtggtacctg tg      92

<210> SEQ ID NO 145
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
gattgtttga gtaggaccac atattggtca tcttggtatg tccagttcct ggaaagtaaa      60
atattaataa cactgaggac gtggtacctg tg      92

<210> SEQ ID NO 146
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 146
gaggagcctt catactagac actctaagat tgtttgagta ggaccacata ttggtcatct      60
tggtatgtcc agttcctgga aagtaaaata ttaataacac tgaggacgtg gtacctg      117

<210> SEQ ID NO 147
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 147
gaggagcctt catactagac actctaagat tgtttgagca ggaccacata ttggtcatct      60
tggtatgtcc agttcctgga aaataaaata ttaataacac tgaggacgtg gtacctg      117

<210> SEQ ID NO 148
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 148
gaggagcctt catactagac actctaagat tgtttgagta ggaccacata ttggtcatct      60
tggtatgtcc agttcctgga aagtaaaata ttaataacac tgaggacgtg gtacctg      117

<210> SEQ ID NO 149
<211> LENGTH: 155
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 149
cttgctctga gcctcatccc ccacgtacga gtccttctgg cccatgccca ccattacgcc    60
ctgcggagag aggagcgagg aggcgccttc agctccggcc aagtcccacc gaccccacc    120 acccacccag aaagccaaaa aggcctccct ccacc                              155

<210> SEQ ID NO 150
<211> LENGTH: 155
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (65)..(66)
<223> OTHER INFORMATION: a, c, t, g, unknown or other

<400> SEQUENCE: 150
cttgctctga gcctcatccc ccacgtacga gtccttctgg cccatgccca ccattacgcc    60
ctgcnnagag aggagcgagg aggcgccttc agctacggcc aagtcccacc gaccccacc    120 acccacccag aaagcctaaa aggcctccct tcacc                              155

<210> SEQ ID NO 151
<211> LENGTH: 155
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 151
cttgctctga gcctcatccc ccacgtacga gtccttctgg cccatgccca ccattacgcc    60
ctgcggagag aggagcgagg aggcgccttc agctccggcc aagtcccacc gaccccacc    120 acccacccag aaagccaaaa aggcctccct ccacc                              155

<210> SEQ ID NO 152
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 152
gacttagcct ccagtgtggc cacagggtga ccttcgtgtg gggcaggcag ggcgggcctt    60
ctcactcacc caggaaggaa ggctggaaga gagcc                              95

<210> SEQ ID NO 153
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 153

```
gacttagcct ccagtgtggc cacagggtga ccttcgtgtg gggcgggcag ggcgggcctt    60
ctcactcacc caggaaggaa ggctggaaga gagcc                              95

<210> SEQ ID NO 154
<211> LENGTH: 95
<212> TYPE: DNA
<213> ORGANISM: Bos indicus

<400> SEQUENCE: 154
gacttagcct ccagtgtggc cacagggtga ccttcgtgtg gggcgggcag ggcgggcctt    60
ctcactcacc caggaaggaa ggctggaaga gagcc                              95

<210> SEQ ID NO 155
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
caccgcatat tacttcctcc cctttaaaac agtgcagtcg tatgcttctg ctatgttcag    60
agtattgaac gacgatgttt acagtc                                        86

<210> SEQ ID NO 156
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
cagtgcagtc gtatgcttct gctatgttca gagtattgaa cgacgatgtt tacagtccag    60
ctgtggtaca gcaacaaact actctcgctt ttaggaaaga ctcttccttg tgcacagac   119

<210> SEQ ID NO 157
<211> LENGTH: 432
<212> TYPE: DNA
<213> ORGANISM: Bos taurus

<400> SEQUENCE: 157
agtcatagcg caaatgatca gtgtgaaagg ggagaacatg ttagggagag cagccaggac    60
cacgtcaagc gacccatgaa cgccttcatt gtgtggtctc gtgaacgaag acgaaaggtg   120
gctctagaga atcccaaaat gaaaaactca gacatcagca agcagctggg atatgagtgg   180
aaaaggctta cagatgctga aaagcgccca ttctttgagg aggcacagag actactagcc   240
atacaccgag acaaataccc gggctataaa tatcgacctc gtcggagagc caagaggcca   300
cagaaatcgc ttcctgcaga ctcttcaata ctatgcaacc cgatgcatgt agagacattg   360
caccccttca catacaggga tggttgtgcc aagaccacat actcacaaat ggaaagccaa   420
ttaagccggt ca                                                      432

<210> SEQ ID NO 158
<211> LENGTH: 12
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"

<400> SEQUENCE: 158
ttaagccggt ca                                                            12

<210> SEQ ID NO 159
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 159
aattcggcca gtgtcaggca ctagtattgg ttaagtgagg acgttttcct cgtagtgtcg        60
tcgacctgtt cggacccggt gttattccat tgtaaccgat gtgcctaaag ccgcctgaaa       120
gggacattgt tttcgaatct cggacctgaa agaacacgaa taaaagttat aactgaagga       180
atgagagcga ttgtttccgc gagaaataga g                                      211

<210> SEQ ID NO 160
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160
cctgggccac aataaggtaa cattggctac acggatttcg gcggactttc cctgtaacaa        60
aagcttagag cctggacttt cttgtgctta ttttcaatat tgacttcctt actctcgcta       120
acaaaggcgc                                                              130

<210> SEQ ID NO 161
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 161
gaatgagagc gattgtttcc gcgagaaata gagttaaaat gatgtcaaag tggacgctga        60
attaaaatat tcttcgggtt attcattcat gtaaattgta catttcttaa gtctgaaagg       120
ttatattgac caggagacaa ttagtcaaga aagatattct catgaaaaaa catttttaa        180 tagaattgtc gtggttttga cgaactcaag                                        210

<210> SEQ ID NO 162
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
ccaaccgtga gaagatgacc                                                    20

```
<210> SEQ ID NO 163
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
ccaaccgtga aaaaatgacc                                              20

<210> SEQ ID NO 164
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
ccaaccgtga gaagatgacc                                              20

<210> SEQ ID NO 165
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
ctcctttgga actttgcagg ttc                                          23

<210> SEQ ID NO 166
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
ctcctttgga actctgcagg ttc                                          23

<210> SEQ ID NO 167
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
ctcctttgga actttgcagg ttc                                          23

<210> SEQ ID NO 168
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 168
gacgacatgg agaagatctg gc                                              22

<210> SEQ ID NO 169
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(5)
<223> OTHER INFORMATION: a, c, t, g, unknown or other

<400> SEQUENCE: 169
ccnnnctttg cctcaccctt tctcact                                         27

<210> SEQ ID NO 170
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
taggactttc ttctctgagc tga                                             23

<210> SEQ ID NO 171
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
gacgacatgg agaagatctg gc                                              22

<210> SEQ ID NO 172
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
cctttctttg ccacgcccTt tctcact                                         27

<210> SEQ ID NO 173
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
taggactttc ttctctgagc tga                                             23
```

```
<210> SEQ ID NO 174
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gacgacatgg agaagatctg gc                                              22

<210> SEQ ID NO 175
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(5)
<223> OTHER INFORMATION: a, c, t, g, unknown or other

<400> SEQUENCE: 175
ccnnnctttg cctcaccctt tctcact                                         27

<210> SEQ ID NO 176
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
taggactttc ttctctgagc tga                                             23

<210> SEQ ID NO 177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
ccataagtcc ctccacgatg                                                 20

<210> SEQ ID NO 178
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gttggtggtg caggaggcat tg                                              22

<210> SEQ ID NO 179
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 179
ctgcgctcac ctgacaatct                                                  20

<210> SEQ ID NO 180
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
ccataagtcc ctccacgatg                                                  20

<210> SEQ ID NO 181
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gttggtggtg caggaggcat tg                                               22

<210> SEQ ID NO 182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
ctgcgctcac ctgacaatct                                                  20

<210> SEQ ID NO 183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ccataagtcc ctccacgatg                                                  20

<210> SEQ ID NO 184
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gttggtggtg caggaggcat tg                                               22
```

```
<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
ctgcgctcac ctgacaatct                                                  20

<210> SEQ ID NO 186
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
cagcatgaag atggccctg                                                   19

<210> SEQ ID NO 187
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 187
gtcacccagt ngnncctrca tcc                                              23

<210> SEQ ID NO 188
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
cagcatgaag atggccctg                                                   19

<210> SEQ ID NO 189
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(4)
<223> OTHER INFORMATION: a, c, t, g, unknown or other

<400> SEQUENCE: 189
```
gtgncccagt agtgcctaca tcc                                           23

<210> SEQ ID NO 190
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
cagcatgaag atggccctg                                                19

<210> SEQ ID NO 191
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 191
gtcacccagt ngnncctaca tcc                                           23

<210> SEQ ID NO 192
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
tatgcttgcc cacggaagcc                                               20

<210> SEQ ID NO 193
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
cgctgcattg ctgaacgatc                                               20

<210> SEQ ID NO 194
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
tatgctcgac cacggaagcc                                               20

<210> SEQ ID NO 195
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
ttggatttgg tgggtgtgtt gca                                           23

<210> SEQ ID NO 196
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
cgctgcattg ctgaacgatc                                               20

<210> SEQ ID NO 197
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
tatgcttgac cacggaagcc                                               20

<210> SEQ ID NO 198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
cgctgcattg ctgaacgatc                                               20

<210> SEQ ID NO 199
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ctttctacct gctgtcccac g                                             21

<210> SEQ ID NO 200
<211> LENGTH: 24
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 200
agctgccgag tgaaacacgt tact                                          24

<210> SEQ ID NO 201
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
gggaatgtka ttaaacctct gcgta                                         25

<210> SEQ ID NO 202
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
ctttctacct gctgtcccac g                                             21

<210> SEQ ID NO 203
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
agctgccgag tgaaacacgt tact                                          24

<210> SEQ ID NO 204
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
ctttctacct gctgtcccac g                                             21

<210> SEQ ID NO 205
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
agctgccgag tgaaacacgt tact                                          24

<210> SEQ ID NO 206
```

```
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
gggaatgtka ttaaacctct gcrta                                          25

<210> SEQ ID NO 207
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
tttgaacaga ctgatggttc cc                                             22

<210> SEQ ID NO 208
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
acatccttag agctggaact tggcc                                          25

<210> SEQ ID NO 209
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
gcgagggtga cacttcttg                                                 19

<210> SEQ ID NO 210
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ttcgaacaga ctgatggttc cc                                             22

<210> SEQ ID NO 211
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
```

```
acgtccttag agctggaact tggcc                                              25

<210> SEQ ID NO 212
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
gcgagggtga cacttcttg                                                     19

<210> SEQ ID NO 213
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
tttgaacaga ctgatggttc cc                                                 22

<210> SEQ ID NO 214
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
acatccttag agctggaact tggcc                                              25

<210> SEQ ID NO 215
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
gcgagggtga cacttcttg                                                     19

<210> SEQ ID NO 216
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
ttacctgaga gaagacccat gatgc                                              25

<210> SEQ ID NO 217
<211> LENGTH: 23
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 217
gggagcactt tatgctgtag gag                                            23

<210> SEQ ID NO 218
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
ttacctgaga gaagacccat gatgc                                          25

<210> SEQ ID NO 219
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
gggagcactt tatgctgtag gag                                            23

<210> SEQ ID NO 220
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
ttacctgaga gaagacccat gatgc                                          25

<210> SEQ ID NO 221
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
gggagcactt tatgctgtag gag                                            23

<210> SEQ ID NO 222
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
gcacactcac taggagaaac aaacc                                          25
```

```
<210> SEQ ID NO 223
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223 cccttttcaga ctggctacac agca                                         24

<210> SEQ ID NO 224
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
gcagatttga ggagcagttc ca                                            22

<210> SEQ ID NO 225
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
gcacactcac taggagaaac aaacc                                         25

<210> SEQ ID NO 226
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226 cccttttcaga ctggctacac agca                                         24

<210> SEQ ID NO 227
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
gcagatttga ggagcagttc ca                                            22

<210> SEQ ID NO 228
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 228
gcacactcac taggagaaac aaacc                                          25

<210> SEQ ID NO 229
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
ccctttcaga ctggctacac agca                                           24

<210> SEQ ID NO 230
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
gcagatttga ggagcagttc ca                                             22

<210> SEQ ID NO 231
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
gactcaagtc attgaagtct gctcc                                          25

<210> SEQ ID NO 232
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
gcccaaggct gtacaaagct c                                              21

<210> SEQ ID NO 233
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
gactcaagtc attgaagtct gctcc                                          25

<210> SEQ ID NO 234
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 234
gcccaaggct gtacaaagct c                                                   21

<210> SEQ ID NO 235
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
gactcaagtc attgaagtct gctcc                                               25

<210> SEQ ID NO 236
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
gcccaaggct gtacaaagct c                                                   21

<210> SEQ ID NO 237
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
agagaagacc catgatgcaa agtcc                                               25

<210> SEQ ID NO 238
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
tcaacgatgg gagcacttta tgctgt                                              26

<210> SEQ ID NO 239
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
ggaggcatgg atgctatgaa agg                                                 23
```

<210> SEQ ID NO 240
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
agagaagacc catgatgcaa agtcc                                         25

<210> SEQ ID NO 241
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
tcaaccatgg gagcacttta tgctgt                                        26

<210> SEQ ID NO 242
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
ggaggcatgg atgctatgaa agg                                           23

<210> SEQ ID NO 243
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
agagaagacc catgatgcaa agtcc                                         25

<210> SEQ ID NO 244
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
tcaacgatgg gagcacttta tgctgt                                        26

<210> SEQ ID NO 245
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 245
ggaggcatgg atgctatgaa agg                                          23

<210> SEQ ID NO 246
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gaactcaagc agttttggtg c                                            21

<210> SEQ ID NO 247
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ttaagtcgca ggtgaaactg tagt                                         24

<210> SEQ ID NO 248
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
cgcctttgtt agcgagagta ag                                           22

<210> SEQ ID NO 249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
gaactcaagc agttttggtg c                                            21

<210> SEQ ID NO 250
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
ttaagtcgca ggtgaaattg tagt                                         24

<210> SEQ ID NO 251
<211> LENGTH: 22
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
tgcctttgag agcgagagta ag                                              22

<210> SEQ ID NO 252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
gaactcaagc agttttggtg c                                               21

<210> SEQ ID NO 253
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
ttaagtcgca ggtgaaactg tagt                                            24

<210> SEQ ID NO 254
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
cgcctttgtt agcgagagta ag                                              22

<210> SEQ ID NO 255
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
ttactctcgc taacaaaggc g                                               21

<210> SEQ ID NO 256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
gcaccaaaac tgcttgagtt                                                 20
```

-continued

<210> SEQ ID NO 257
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
ttactctcgc tctcaaaggc a                                              21

<210> SEQ ID NO 258
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
gcaccaaaac tgcttgagtt                                                20

<210> SEQ ID NO 259
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
ttactctcgc taacaaaggc g                                              21

<210> SEQ ID NO 260
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
gcaccaaaac tgcttgagtt                                                20

<210> SEQ ID NO 261
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
aattcggcca gtgtcaggc                                                 19

<210> SEQ ID NO 262
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:

```
      Synthetic oligonucleotide"

<400> SEQUENCE: 262
cattgtaacc gatgtgccta aagc                                       24

<210> SEQ ID NO 263
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
gcgattgttt ccgcgagaaa tagag                                      25

<210> SEQ ID NO 264
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
aattcggcca gtgtcaggc                                             19

<210> SEQ ID NO 265
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
cattgtaacc gatgtgccta aagc                                       24

<210> SEQ ID NO 266
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
gcgagagttt ccgtgagaaa tagag                                      25

<210> SEQ ID NO 267
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
gagataaaga gcgcctttgt tagcg                                      25

<210> SEQ ID NO 268
<211> LENGTH: 24
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
cgaaatccgt gtagccaatg ttac                                          24

<210> SEQ ID NO 269
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
cggactgtga ccggcttaa                                                19

<210> SEQ ID NO 270
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
agattgtcag gtgagcgcag                                               20

<210> SEQ ID NO 271
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
caatgcctcc tgcaccacca ac                                            22

<210> SEQ ID NO 272
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
catcgtggag ggacttatgg                                               20

<210> SEQ ID NO 273
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
```

```
agattgtcag gtgagcgcag                                               20

<210> SEQ ID NO 274
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
caatgcctcc tgcaccacca ac                                            22

<210> SEQ ID NO 275
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
catcgtggag ggacttatgg                                               20

<210> SEQ ID NO 276
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
agattgtcag gtgagcgcag                                               20

<210> SEQ ID NO 277
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
caatgcctcc tgcaccacca ac                                            22

<210> SEQ ID NO 278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
catcgtggag ggacttatgg                                               20

<210> SEQ ID NO 279
<211> LENGTH: 20
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"

<400> SEQUENCE: 279
ctcctgcgac ttcaacagcg                                          20

<210> SEQ ID NO 280
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
ttgccctcaa cgaccacttt gtca                                     24

<210> SEQ ID NO 281
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
ggtggctggc tcggtaaac                                           19

<210> SEQ ID NO 282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
ctcctgcgac ttcaacagcg                                          20

<210> SEQ ID NO 283
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
ttgccctcaa cgaccacttt gtca                                     24

<210> SEQ ID NO 284
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
ggtggctggc tcggtaaac                                           19

<210> SEQ ID NO 285

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
ctcctgcgac ttcaacagcg                                            20

<210> SEQ ID NO 286
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
ttgccctcaa cgaccacttt gtca                                       24

<210> SEQ ID NO 287
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
ggtggctggc tcggtaaac                                             19

<210> SEQ ID NO 288
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
cgacaatgaa ttcggctaca g                                          21

<210> SEQ ID NO 289
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
tcatggtcca catggcctcc aag                                        23

<210> SEQ ID NO 290
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (7)..(8)
<223> OTHER INFORMATION: a, c, t, g, unknown or other

<400> SEQUENCE: 290
gaagagnntt cctcagctg                                                19

<210> SEQ ID NO 291
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
cgacaatgaa ttcggctaca g                                             21

<210> SEQ ID NO 292
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
tcatggtcca catggcctcc aag                                           23

<210> SEQ ID NO 293
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
gaagagagtt cctccgctg                                                19

<210> SEQ ID NO 294
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
cgacaatgaa tttggctaca g                                             21

<210> SEQ ID NO 295
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
tcatggtcca catggcctcc aag                                           23

<210> SEQ ID NO 296
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(8)
<223> OTHER INFORMATION: a, c, t, g, unknown or other

<400> SEQUENCE: 296
gaagagnntt cctcagctg                                                19

<210> SEQ ID NO 297
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
gaagacccat gatgcaaagt cc                                            22

<210> SEQ ID NO 298
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
tcaacgatgg gagcacttta tgctgt                                        26

<210> SEQ ID NO 299
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
ggaggcatgg atgctatgaa agg                                           23

<210> SEQ ID NO 300
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
gaagacccat gatgcaaagt cc                                            22

<210> SEQ ID NO 301
<211> LENGTH: 26
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"

<400> SEQUENCE: 301
tcaaccatgg gagcacttta tgctgt                                          26

<210> SEQ ID NO 302
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
ggaggcatgg atgctatgaa agg                                             23

<210> SEQ ID NO 303
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
gaagacccat gatgcaaagt cc                                              22

<210> SEQ ID NO 304
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
tcaacgatgg gagcacttta tgctgt                                          26

<210> SEQ ID NO 305
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
ggaggcatgg atgctatgaa agg                                             23

<210> SEQ ID NO 306
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
gtggttggag gatatgatgg ac                                              22

<210> SEQ ID NO 307

```
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
tgcacagaaa gatgaatgga gagaggt                                          27

<210> SEQ ID NO 308
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
ccattctctt ccactctagg gc                                               22

<210> SEQ ID NO 309
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
gtggttggag gatatgatgg ac                                               22

<210> SEQ ID NO 310
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
tgcacagaaa gatgaatgga gagaggt                                          27

<210> SEQ ID NO 311
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
ccattctctt ccactctagg gc                                               22

<210> SEQ ID NO 312
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
```

```
gtggttggag gatatgatgg ac                                            22

<210> SEQ ID NO 313
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
tgcacagaaa gatgaatgga gagaggt                                       27

<210> SEQ ID NO 314
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
ccattctctt ccactctagg gc                                            22

<210> SEQ ID NO 315
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
gcacagaaag atgaatggag ag                                            22

<210> SEQ ID NO 316
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (23)..(27)
<223> OTHER INFORMATION: a, c, t, g, unknown or other

<400> SEQUENCE: 316
tggaattcat cccattctct tcnnnnnt                                      28

<210> SEQ ID NO 317
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
gggctgaatc aaattacttt agtg                                          24

<210> SEQ ID NO 318
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gcacagaaag atgaatggag ag                                             22

<210> SEQ ID NO 319
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
tggaattcat cccattctct tccactct                                       28

<210> SEQ ID NO 320
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
gggctgaatc aaattacttt agtg                                           24

<210> SEQ ID NO 321
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
gcacagaaag atgaatggag ag                                             22

<210> SEQ ID NO 322
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (23)..(27)
<223> OTHER INFORMATION: a, c, t, g, unknown or other

<400> SEQUENCE: 322
tggaattcat cccattctct tcnnnnnt                                       28

<210> SEQ ID NO 323
<211> LENGTH: 24
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 323
gggctgaatc aaattacttt agtg                                          24

<210> SEQ ID NO 324
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
gcacactcac taggagaaac aaacc                                         25

<210> SEQ ID NO 325
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
ccctttcaga ctggctacac agca                                          24

<210> SEQ ID NO 326
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
gcagatttga ggagcagttc ca                                            22

<210> SEQ ID NO 327
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
gcacactcac taggagaaac aaacc                                         25

<210> SEQ ID NO 328
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
ccctttcaga ctggctacac agca                                          24

<210> SEQ ID NO 329
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
gcagatttga ggagcagttc ca                                              22

<210> SEQ ID NO 330
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
gcacactcac taggagaaac aaacc                                           25

<210> SEQ ID NO 331
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331 cccttcaga ctggctacac agca                                             24

<210> SEQ ID NO 332
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
gcagatttga ggagcagttc ca                                              22

<210> SEQ ID NO 333
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
cagtgatgcc tcccatgtc                                                  19

<210> SEQ ID NO 334
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
```
acaggcatgg tttaggtaag agct                                          24

<210> SEQ ID NO 335
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
gactgtacat ttactagagc                                               20

<210> SEQ ID NO 336
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
cagtgatgcc tcccatgtc                                                19

<210> SEQ ID NO 337
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
acaggcatgg tttaggtaag agct                                          24

<210> SEQ ID NO 338
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
gactgtgcat ttactagagc                                               20

<210> SEQ ID NO 339
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
cagtgatgcc tcccatgtc                                                19

<210> SEQ ID NO 340
<211> LENGTH: 24
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 340
acaggcatgg tttaggtaag agct                                          24

<210> SEQ ID NO 341
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
gactgtacat ttactagagc                                               20

<210> SEQ ID NO 342
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
ggcatgatgt gcaggctag                                                19

<210> SEQ ID NO 343
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
gcaacaagac ctagcaatgc tgct                                          24

<210> SEQ ID NO 344
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
gttacttcca ccacaggtat gg                                            22

<210> SEQ ID NO 345
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
ggcatgatgt gcaggctag                                                19
```

```
<210> SEQ ID NO 346
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
gcaacaagac ctagcaatgc tgct                                              24

<210> SEQ ID NO 347
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
gttacttcca ccacaggtat gg                                                22

<210> SEQ ID NO 348
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
ggcatgatgt gcaggctag                                                    19

<210> SEQ ID NO 349
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
gcaacaagac ctagcaatgc tgct                                              24

<210> SEQ ID NO 350
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
gttacttcca ccacaggtat gg                                                22

<210> SEQ ID NO 351
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 351
ttaagccggt cacagtccg                                              19

<210> SEQ ID NO 352
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
gtaacattgg ctacacggat ttcg                                        24

<210> SEQ ID NO 353
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
cgctaacaaa ggcgctcttt atctc                                       25

<210> SEQ ID NO 354
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
ttaagccggt cacagtccg                                              19

<210> SEQ ID NO 355
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
gtaacattgg ctacacggat ttcg                                        24

<210> SEQ ID NO 356
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
cgctctcaaa ggcactcttt atctc                                       25

<210> SEQ ID NO 357
<211> LENGTH: 19
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 357
ttaagccggt cacagtccg                                                  19

<210> SEQ ID NO 358
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gtaacattgg ctacacggat ttcg                                            24

<210> SEQ ID NO 359
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
cgctaacaaa ggcgctcttt atctc                                           25

<210> SEQ ID NO 360
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
cctgggccac aataagg                                                    17

<210> SEQ ID NO 361
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
acacggattt cggcggactt tccc                                            24

<210> SEQ ID NO 362
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
ctctcgctaa caaaggcgc                                                  19
```

```
<210> SEQ ID NO 363
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
cctgggccac aataggg                                                17

<210> SEQ ID NO 364
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
acacggattt cggaggactt tccc                                        24

<210> SEQ ID NO 365
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
ctctcgctct caaaggcac                                              19

<210> SEQ ID NO 366
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
cctgggccac aataagg                                                17

<210> SEQ ID NO 367
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
acacggattt cggcggactt tccc                                        24

<210> SEQ ID NO 368
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 368
ctctcgctaa caaaggcgc                                              19

<210> SEQ ID NO 369
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
cttactctcg ctaacaaagg cg                                          22

<210> SEQ ID NO 370
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
ggtcctctgt taatcagttc tttcta                                      26

<210> SEQ ID NO 371
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
gcaccaaaac tgcttgagtt c                                           21

<210> SEQ ID NO 372
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
cttactctcg ctctcaaagg ca                                          22

<210> SEQ ID NO 373
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
ggtcctctgt taatcagttc tttctg                                      26

<210> SEQ ID NO 374
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
gcaccaaaac tgcttgagtt c                                        21

<210> SEQ ID NO 375
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
cttactctcg ctaacaaagg cg                                       22

<210> SEQ ID NO 376
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
ggtcctctgt taaycagttc tttcta                                   26

<210> SEQ ID NO 377
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
gcaccaaaac tgcttgagtt c                                        21

<210> SEQ ID NO 378
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
cagtgcagtc gtatgcttc                                           19

<210> SEQ ID NO 379
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
cgacgatgtt tacagtccag ctgt                                     24
```

<210> SEQ ID NO 380
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
ctcttccttg tgcacagac                                                19

<210> SEQ ID NO 381
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
cagtgcagtc gtatgcttc                                                19

<210> SEQ ID NO 382
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
cgacgatgtt tacagtccag cggt                                          24

<210> SEQ ID NO 383
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
ctcttcctcg tgcacagac                                                19

<210> SEQ ID NO 384
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
cagtgcagtc gtatgcttc                                                19

<210> SEQ ID NO 385
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:

```
                      Synthetic oligonucleotide"

<400> SEQUENCE: 385
cgacgatgtt tacagtccag ctgt                                          24

<210> SEQ ID NO 386
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
ctcttccttg tgcacagac                                                19

<210> SEQ ID NO 387
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
caccgcatat tacttcctcc cc                                            22

<210> SEQ ID NO 388
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
acagtgcagt cgtatgcttc tgct                                          24

<210> SEQ ID NO 389
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
gtattgaacg acgatgttta cagtc                                         25

<210> SEQ ID NO 390
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
caccgcatat tatttcctcc tc                                            22

<210> SEQ ID NO 391
<211> LENGTH: 24
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
acagtgcagt cgtatgcttc tgct                                          24

<210> SEQ ID NO 392
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
gtattgaacg acgatgttta cagtc                                         25

<210> SEQ ID NO 393
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
caccgcatat tacttcctcc cc                                            22

<210> SEQ ID NO 394
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
acagtgcagt cgtatgcttc tgct                                          24

<210> SEQ ID NO 395
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
gtattgaacg acgatgttta cagtc                                         25

<210> SEQ ID NO 396
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
```

```
gattgtttga gtaggaccac                                              20

<210> SEQ ID NO 397
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
ggtcatcttg gtatgtccag ttcctgg                                      27

<210> SEQ ID NO 398
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
gaggacgtgg tacctgtg                                                18

<210> SEQ ID NO 399
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
gattgtttga gcaggaccac                                              20

<210> SEQ ID NO 400
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
ggtcatcttg gtatgtccag ttcctgg                                      27

<210> SEQ ID NO 401
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
gaggacgtgg tacctgtg                                                18

<210> SEQ ID NO 402
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 402
gattgtttga gtaggaccac                                              20

<210> SEQ ID NO 403
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
ggtcatcttg gtatgtccag ttcctgg                                      27

<210> SEQ ID NO 404
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
gaggacgtgg tacctgtg                                                18

<210> SEQ ID NO 405
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
gaggagcctt catactagac ac                                           22

<210> SEQ ID NO 406
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
ggtcatcttg gtatgtccag ttcctgg                                      27

<210> SEQ ID NO 407
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
cactgaggac gtggtacctg                                              20

<210> SEQ ID NO 408
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
gaggagcctt catactagac ac                                             22

<210> SEQ ID NO 409
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
ggtcatcttg gtatgtccag ttcctgg                                        27

<210> SEQ ID NO 410
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
cactgaggac gtggtacctg                                                20

<210> SEQ ID NO 411
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
gaggagcctt catactagac ac                                             22

<210> SEQ ID NO 412
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
ggtcatcttg gtatgtccag ttcctgg                                        27

<210> SEQ ID NO 413
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
```

```
cactgaggac gtggtacctg                                            20

<210> SEQ ID NO 414
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
cttgctctga gcctcatcc                                             19

<210> SEQ ID NO 415
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
cttcagctcc ggccaagtcc ca                                         22

<210> SEQ ID NO 416
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
ccaaaaaggc ctccctccac c                                          21

<210> SEQ ID NO 417
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
cttgctctga gcctcatcc                                             19

<210> SEQ ID NO 418
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
cttcagctac ggccaagtcc ca                                         22

<210> SEQ ID NO 419
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 419
cctaaaaggc ctcccttcac c                                              21

<210> SEQ ID NO 420
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
cttgctctga gcctcatcc                                                 19

<210> SEQ ID NO 421
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
cttcagctcc ggccaagtcc ca                                             22

<210> SEQ ID NO 422
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
ccaaaaaggc ctccctccac c                                              21

<210> SEQ ID NO 423
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
gacttagcct ccagtgtggc                                                20

<210> SEQ ID NO 424
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
ggccttctca ctcacccagg aa                                             22
```

```
<210> SEQ ID NO 425
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
ggaaggctgg aagagagcc                                                    19

<210> SEQ ID NO 426
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
gacttagcct ccagtgtggc                                                   20

<210> SEQ ID NO 427
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
ggccttctca ctcacccagg aa                                                22

<210> SEQ ID NO 428
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
ggaaggctgg aagagagcc                                                    19

<210> SEQ ID NO 429
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
gacttagcct ccagtgtggc                                                   20

<210> SEQ ID NO 430
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 430
ggccttctca ctcacccagg aa                                           22

<210> SEQ ID NO 431
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
ggaaggctgg aagagagcc                                               19

<210> SEQ ID NO 432
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
caccgcatat tacttcctcc cc                                           22

<210> SEQ ID NO 433
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
acagtgcagt cgtatgcttc tgct                                         24

<210> SEQ ID NO 434
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
gtattgaacg acgatgttta cagtc                                        25

<210> SEQ ID NO 435
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
cagtgcagtc gtatgcttc                                               19

<210> SEQ ID NO 436
<211> LENGTH: 24
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 436
cgacgatgtt tacagtccag ctgt                                          24

<210> SEQ ID NO 437
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
ctcttccttg tgcacagac                                                19

<210> SEQ ID NO 438
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
aattcggcca gtgtcaggc                                                19

<210> SEQ ID NO 439
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
cattgtaacc gatgtgccta aagc                                          24

<210> SEQ ID NO 440
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
gcgattgttt ccgcgagaaa tagag                                         25

<210> SEQ ID NO 441
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
cctgggccac aataagg                                                  17
```

<210> SEQ ID NO 442
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
acacggattt cggcggactt tccc                                            24

<210> SEQ ID NO 443
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
ctctcgctaa caaaggcgc                                                  19

<210> SEQ ID NO 444
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
gaatgagagc gattgtttcc gc                                              22

<210> SEQ ID NO 445
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
tgatgtcaaa gtggacgctg aatt                                            24

<210> SEQ ID NO 446
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
cgtggttttg acgaactcaa g                                               21

<210> SEQ ID NO 447
<211> LENGTH: 243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<220> FEATURE:
<221> NAME/KEY: modified_base
<222> LOCATION: (173)..(175)
<223> OTHER INFORMATION: a, c, t, g, unknown or other

<400> SEQUENCE: 447
gacgacatgg agaagatctg gcaccacacc ttctacaacg agctccgtgt ggcccctgag    60
gagcaccccg tgctgctgac cgaggccccc ctgaacccca aggccaaccg tgagaagatg   120
acccaggtca gtgggccgtc ctgccttgcc tccgcgcccc tcctttcttg ccnnnctttg   180
cctcaccctt tctcacttat tctctcttct gccattttcc taggactttc ttctctgagc   240
tga                                                                 243

<210> SEQ ID NO 448
<211> LENGTH: 243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 448
gacgacatgg agaagatctg gcaccacacc ttctacaacg agctccgtgt ggcccctgag    60
gagcaccccg tgctgctgac cgaggccccc ctgaacccca aggccaaccg tgaaaagatg   120
acccaggtca gtgggccgcc cggccttgcc tccgcgcccc tcctttcttg cctttctttg   180
ccacgcccct tctcacttat tctctcttct gccatttccc taggactttc ttctctgagc   240
tga                                                                 243

<210> SEQ ID NO 449
<211> LENGTH: 243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (173)..(175)
<223> OTHER INFORMATION: a, c, t, g, unknown or other

<400> SEQUENCE: 449
gacgacatgg agaagatctg gcaccacacc ttctacaacg agctccgtgt ggcccctgag    60 gagcayccccg tgctgctgac cgaggccccc ctgaacccca aggccaaccg tgagaagatg   120
acccaggtca gtgggccgcc ctgccttgcc tccgcgcccc tcctttcttg ccnnnctttg   180
cctcaccctt tctcacttat tctctcttct gccattttcc taggactttc ttctctgagc   240
tga                                                                 243

<210> SEQ ID NO 450
<211> LENGTH: 185
<212> TYPE: DNA
<213> ORGANISM: Bos taurus

<400> SEQUENCE: 450
ccataagtcc ctccacgatg ccaaagtggt catggatgac cttggccagg ggggccaagc    60
agttggtggt gcaggaggca ttgctggaaa agagggaggc aagtcagggg cacgtccact   120
gggcaccagg gggcactatc agcccgcttc cccacctcct ctctgctgcg ctcacctgac   180

```
aatct                                                                    185

<210> SEQ ID NO 451
<211> LENGTH: 185
<212> TYPE: DNA
<213> ORGANISM: Bubalus bubalis

<400> SEQUENCE: 451
ccataagtcc ctccacgatg ccaaagtggt catggatgac cttggccagg ggggccaagc        60
agttggtggt gcaggaggca ttgctggaaa agagggaggc aagtcagggg cacgtccact       120
gggcaccagg gggcactatc agcccgcttc ccacctcct ctctgctgcg ctcacctgac        180
aatct                                                                    185

<210> SEQ ID NO 452
<211> LENGTH: 185
<212> TYPE: DNA
<213> ORGANISM: Bos indicus

<400> SEQUENCE: 452
ccataagtcc ctccacgatg ccaaagtggt catggatgac cttggccagg ggggccaagc        60
agttggtggt gcaggaggca ttgctggaaa agagggaggc aagtcagggg cacgtccact       120
gggcaccagg gggcactatc agcccgcttc ccacctcct ctctgctgcg ctcacctgac        180
aatct                                                                    185

<210> SEQ ID NO 453
<211> LENGTH: 151
<212> TYPE: DNA
<213> ORGANISM: Bubalus bubalis

<400> SEQUENCE: 453
ggaagcgggc tgatagtgcc ccctggtgcc cagtggacgt gcccctgact tgcctccctc        60
ttttccagca atgcctcctg caccaccaac tgcttggccc cctggccaa ggtcatccat        120 gaccactttg gcatcgtgga gggacttatg g                                       151

<210> SEQ ID NO 454
<211> LENGTH: 160
<212> TYPE: DNA
<213> ORGANISM: Bubalus bubalis

<400> SEQUENCE: 454
agattgtcag gtgagcgcag cagagaggag gtggggaagc gggctgatag tgcccctgg         60 tgcccagtgg acgtgcccct gacttgcctc cctctcaatg cctcctgcac caccaactgc       120
ttggcccccc tggccaaggt catccatgac cactttggca                             160

<210> SEQ ID NO 455
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: modified_base
<222> LOCATION: (223)..(224)
<223> OTHER INFORMATION: a, c, t, g, unknown or other
```

<400> SEQUENCE: 455

| cagcatgaag atggccctga agatgatcca cagctggtgg gcatcactgc ccggaacatt | 60 |
| --- | --- |
| ccacgacaac cccagctggc tgctgagaac ctgggcatca gcctggccac cttgttgctg | 120 |
| aacaaaggag ccaagaacat cttggatgtt gcacggcagc tcaatgaagc ccactaattg | 180 |
| gtctgtgggg cacaggtgcc tgccttgctg gtcacccagt ngnncctrca tcc | 233 |

<210> SEQ ID NO 456
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (214)..(214)
<223> OTHER INFORMATION: a, c, t, g, unknown or other

<400> SEQUENCE: 456

| cagcatgaag atggccctga agatgatcca cagctggtgg gcatcactgc ccggaacatt | 60 |
| --- | --- |
| ccacgacaac cccagctggc tgctgagaac ctgggcatca gcctggccac cttgttgctg | 120 |
| aacaaaggag ccaagaacat cttggatgtt gcacggcagc tcaatgaagc ccactaattg | 180 |
| gtctgtgggg cacaggtgcc tgccttgctg gtgnccagt agtgcctaca tcc | 233 |

<210> SEQ ID NO 457
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: modified_base
<222> LOCATION: (223)..(224)
<223> OTHER INFORMATION: a, c, t, g, unknown or other

<400> SEQUENCE: 457

| cagcatgaag atggccctga agatgatcca cagctggtgg gcatcactgc ccggaacatt | 60 |
| --- | --- |
| ccacgacaac cccagctggc tgctgagaac ctgggcatca gcctggccac cttgttgctg | 120 |
| aacaaaggag ccaagaacat cttggatgtt gcacggcagc tcaatgaagc ccactaattg | 180 |
| gtctgtgggg cacaggtgcc tgccttgctg gtcacccagt ngnncctaca tcc | 233 |

<210> SEQ ID NO 458
<211> LENGTH: 227
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 458

| tatgcttgcc cacggaagcc atgtattgtt gtctcctcct tttgttttca accaagttct | 60 |
| --- | --- |
| gtcccttagc tccattggct ggggaaagat tggtactggt atcttaggct attttcccat | 120 |

```
caggggctc tgggtgtgga agttcgagcc aaagaccagg acatcttgga tctggtgggt    180
gtgttgcacg atcctgagac tctacttcgc tgcattgctg aacgatc                227
```

<210> SEQ ID NO 459
<211> LENGTH: 227
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (29)..(29)
<223> OTHER INFORMATION: a, c, t, g, unknown or other

<400> SEQUENCE: 459

```
tatgctcgac cacggaagcc atgtattgnt gtctcctcct tttgttttca accaagttct    60
gtcccttagc tccattggct ggggaaagat cggtactggt atcttaggct attttcccat   120 caggggctc tgggtgtgga agttcgagcc aaagaccagg acatcttgga tttggtgggt   180
gtgttgcacg atcctgagac tctacttcgc tgcattgctg aacgatc                227
```

<210> SEQ ID NO 460
<211> LENGTH: 227
<212> TYPE: DNA
<213> ORGANISM: Bos indicus

<400> SEQUENCE: 460

```
tatgcttgac cacggaagcc atgtattgtt gtctcctcct tttgttttca accaagttct    60
gtcccttagc tccattggct ggggaaagat tggtactggt atcttaggct attttcccat   120 caggggctc tgggtgtgga agttcgagcc aaagaccagg acatcttgga tctggtgggt   180
gtgttgcacg atcctgagac tctacttcgc tgcattgctg aacgatc                227
```

<210> SEQ ID NO 461
<211> LENGTH: 233
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 461

```
ctttctacct gctgtcccac gctgagttca ctcccaacag caaggatcag tacagctgcc    60
gagtgaaaca cgttactttg gaacaacccc ggatagttaa gtggggtaag ttttcaagtt   120
ctttggttaa ccactgacag ttgtatctga gcacagctgc ggcatatagc tgctttgata   180
taaaaacgtc tgcatactgg gattatcagg gaatgtkatt aaacctctgc gta          233
```

<210> SEQ ID NO 462
<211> LENGTH: 92
<212> TYPE: DNA
<213> ORGANISM: Bubalus bubalis

<400> SEQUENCE: 462

```
ctttctacct gctgtcccac gctgagttca ctcccaacag caaggatcag tacagctgcc    60
gagtgaaaca cgttactttg gaacaacccc gg                                  92
```

<210> SEQ ID NO 463
<211> LENGTH: 233

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 463
ctttctacct gctgtcccac gctgagttca ctcccaacag caaggatcag tacagctgcc      60
gagtgaaaca cgttactttg aacaacccc ggatagttaa gtggggtaag ttttcaagtt     120
ctttggttaa ccactgacag ttgtatctga gcacagctgc ggcatatagc tgctttgata    180
taamaacgtc tgcatactgg gattatcagg gaatgtkatt aaacctctgc rta           233

<210> SEQ ID NO 464
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
tttgaacaga ctgatggttc ccattagtca cataaagctg tagtcaagta cagacatcct     60
tagagctgga acttggccag gcgagggtga cacttcttg                            99

<210> SEQ ID NO 465
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
ttcgaacaga ctgatggttc ccattagtcg cataaagctg tagtcaagta cagacgtcct     60
tagagctgga acttggccag gcgagggtga cacttcttg                            99

<210> SEQ ID NO 466
<211> LENGTH: 99
<212> TYPE: DNA
<213> ORGANISM: Bos indicus

<400> SEQUENCE: 466
tttgaacaga ctgatggttc ccattagtca cataaagctg tagtcaagta cagacatcct     60
tagagctgga acttggccag gcgagggtga cacttcttg                            99

<210> SEQ ID NO 467
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
ttacctgaga gaagacccat gatgcaaagt cctaggacaa ggcctagaaa atcaacgatg     60
ggagcacttt atgctgtagg ag                                              82

<210> SEQ ID NO 468
```

```
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
ttacctgaga gaagacccat gatgcaaagt cctaggacaa ggcctagaaa atcaaccatg    60
ggagcacttt atgctgtagg ag                                            82

<210> SEQ ID NO 469
<211> LENGTH: 82
<212> TYPE: DNA
<213> ORGANISM: Bos indicus

<400> SEQUENCE: 469
ttacctgaga gaagacccat gatgcaaagt cctaggacaa ggcctagaaa atcaacgatg    60
ggagcacttt atgctgtagg ag                                            82

<210> SEQ ID NO 470
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 470
gcacactcac taggagaaac aaaccatatt ctcacactta tgcccctttc agactggcta    60
cacagcatgc tgaagacatg agtgttagca gatttgagga gcagttcca              109

<210> SEQ ID NO 471
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 471
gcacactcac taggagaaac aaaccatatt ctcacacttt tcccccttte agactggcta    60 cacagcatgc tgaagacatg agtgttagca gatttgagga gcagttcca              109

<210> SEQ ID NO 472
<211> LENGTH: 109
<212> TYPE: DNA
<213> ORGANISM: Bos indicus

<400> SEQUENCE: 472
gcacactcac taggagaaac aaaccatatt ctcacactta tgcccctttc agactggcta    60
cacagcatgc tgaagacatg agtgttagca gatttgagga gcagttcca              109

<210> SEQ ID NO 473
<211> LENGTH: 205
<212> TYPE: DNA
<213> ORGANISM: Bos indicus

<400> SEQUENCE: 473
gcacactcac taggagaaac aaaccatatt ctcacactta tgcccctttc agactggcta    60
```

```
cacagcatgc tgaagacatg agtgttagca gatttgagga gcagttccat gctgtaaacc    120
atgcacaaca aactcttcaa aaaatggaga actacttgaa agagaaacaa ctgtgtgatg    180
tgttactcat tgctggacat ctccg                                          205
```

<210> SEQ ID NO 474
<211> LENGTH: 122
<212> TYPE: DNA
<213> ORGANISM: Bos indicus

<400> SEQUENCE: 474

```
ccactggata tttgcacact cactaggaga aacaaaccat attctcacac ttatgcccct    60
ttcagactgg ctacacagca tgctgaagac atgagtgtta gcagatttga ggagcagttc    120
ca                                                                   122
```

<210> SEQ ID NO 475
<211> LENGTH: 106
<212> TYPE: DNA
<213> ORGANISM: Bos taurus

<400> SEQUENCE: 475

```
gactcaagtc attgaagtct gctccaattt tcttataaag cagctccacc cttcaaactg    60
cttagggatt ctatcatttg gagatgccca aggctgtaca aagctc                   106
```

<210> SEQ ID NO 476
<211> LENGTH: 106
<212> TYPE: DNA
<213> ORGANISM: Bubalus bubalis

<400> SEQUENCE: 476

```
gactcaagtc attgaagtct gctccaattt tcttataaag cagctccacc cttcaaactg    60
cttagggatt ctatcatttg gagatgccca aggctgtaca aagctc                   106
```

<210> SEQ ID NO 477
<211> LENGTH: 106
<212> TYPE: DNA
<213> ORGANISM: Bos indicus

<400> SEQUENCE: 477

```
gactcaagtc attgaagtct gctccaattt tcttataaag cagctccacc cttcaaactg    60
cttagggatt ctatcatttg gagatgccca aggctgtaca aagctc                   106
```

<210> SEQ ID NO 478
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478

```
agagaagacc catgatgcaa agtcctagga caaggcctag aaaatcaacg atgggagcac    60
tttatgctgt aggaggcatg gatgctatga aagg                                94
```

<210> SEQ ID NO 479
<211> LENGTH: 94
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 479
agagaagacc catgatgcaa agtcctagga caaggcctag aaaatcaacc atgggagcac    60
tttatgctgt aggaggcatg gatgctatga aagg                                94

<210> SEQ ID NO 480
<211> LENGTH: 94
<212> TYPE: DNA
<213> ORGANISM: Bos indicus

<400> SEQUENCE: 480
agagaagacc catgatgcaa agtcctagga caaggcctag aaaatcaacg atgggagcac    60
tttatgctgt aggaggcatg gatgctatga aagg                                94

<210> SEQ ID NO 481
<211> LENGTH: 138
<212> TYPE: DNA
<213> ORGANISM: Bos taurus

<400> SEQUENCE: 481
agagaagacc catgatgcaa agtcctagga caaggcctag aaaatcaacg atgggagcac    60
tttatgctgt aggaggcatg gatgctatga aggtaacag aagcaaatta attactcttg   120
ctgctgctaa gtcacgtc                                                 138

<210> SEQ ID NO 482
<211> LENGTH: 168
<212> TYPE: DNA
<213> ORGANISM: Bos taurus

<400> SEQUENCE: 482
cagctccatg tttactggtg atcttgaatg tcagaaactc ctgatggaag ctatgaagta    60
tcatctctta cctgagagaa gacccatgat gcaaagtcct aggacaaggc ctagaaaatc   120
aacgatggga gcactttatg ctgtaggagg catggatgct atgaaagg                168

<210> SEQ ID NO 483
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 483
gaactcaagc agttttggtg ctgttaagat aattttttac aaaaaagtac tcttatagaa    60
agaactgatt aacagaggac cagttatatt ggaaagtctg aattctttac atgttaaatg   120
tacttactta tgggcttct tataaaatta agtcgcaggt gaaactgtag taaaattgag    180
ataaagagcg cctttgttag cgagagtaag                                    210

<210> SEQ ID NO 484
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

-continued

<400> SEQUENCE: 484
gaactcaagc agttttggtg ctgttaagat aattttttac aaaaaagtac tcttacagaa    60
agaactgatt aacagaggac caattatatt ggaaagtctg aatcctttac atgttaaatg   120
tacttactta ttgggcttct tttaaaatta agtcgcaggt gaaattgtag taaaattgag   180
ataaagagtg cctttgagag cgagagtaag                                    210

<210> SEQ ID NO 485
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 485
gaactcaagc agttttggtg ctgttaagat aattttttac aaaaaagtac tcttatagaa    60
agaactgrtt aacagaggac cagttatatt ggaaagtctg aattctttac atgttaaatg   120
tacttactta ttgggcttct tataaaatta agtcgcaggt gaaactgtag taaaattgag   180
ataaagagcg cctttgttag cgagagtaag                                    210

<210> SEQ ID NO 486
<211> LENGTH: 208
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 486
ttactctcgc taacaaaggc gctctttatc tcaattttac tacagtttca cctgcgactt    60
aattttataa gaagcccaat aagtaagtac atttaacatg taaagaattc agactttcca   120
atataactgg tcctctgtta atcagttctt tctataagag tactttttg taaaaaatta    180 tcttaacagc accaaaactg cttgagtt                                      208

<210> SEQ ID NO 487
<211> LENGTH: 208
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 487
ttactctcgc tctcaaaggc actctttatc tcaattttac tacaatttca cctgcgactt    60
aattttaaaa gaagcccaat aagtaagtac atttaacatg taaaggattc agactttcca   120
atataattgg tcctctgtta atcagttctt tctgtaagag tactttttg taaaaaatta    180 tcttaacagc accaaaactg cttgagtt                                      208

<210> SEQ ID NO 488
<211> LENGTH: 208
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 488

```
ttactctcgc taacaaaggc gctctttatc tcaattttac tacagtttca cctgcgactt        60
aattttataa gaagcccaat aagtaagtac atttaacatg taaagaattc agactttcca       120
atataactgg tcctctgtta aycagttctt tctataagag tactttttg taaaaaatta        180
tcttaacagc accaaaactg cttgagtt                                          208
```

<210> SEQ ID NO 489
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 489

```
gagataaaga gcgcctttgt tagcgagagt aaggaagtca atattgaaaa taagcacaag        60
aaagtccagg ctctaagctt ttgttacagg gaaagtccgc cgaaatccgt gtagccaatg       120
ttaccttatt gtggcccagg cttgtccagc tgctgtgatg ctccttttgc aggagtgaat       180
tggttatgat cacggactgt gaccggctta a                                      211
```

<210> SEQ ID NO 490
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 490

```
gagataaaga gtgcctttga gagcgagagt aaggaagtca atattgaaaa taagcacaag        60
aaagtccagg ctctaagctt ttgttatagg gaaagtcctc cgaaatccgt gtagccaatg       120
ttaccctatt gtggcccagg cttgtccagc tgctgtgatg ctccttttgc aggagtgaat       180
tggttatgat cacggactgt gaccggctta a                                      211
```

<210> SEQ ID NO 491
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 491

```
gagataaaga gcgcctttgt tagcgagagt aaggaagtca atattgaaaa taagcacaag        60
aaagtccagg ctctaagctt ttgttaaagg gaaagtccgc cgaaatccgt gtagccaatg       120
ttaccttatt gtggcccagg cttgtccagc tgctgtgatg ctccttttgc aggagtgaat       180
tggttatgat cacggactgt gaccggctta a                                      211
```

<210> SEQ ID NO 492
<211> LENGTH: 185
<212> TYPE: DNA
<213> ORGANISM: Bos taurus

<400> SEQUENCE: 492

```
agattgtcag gtgagcgcag cagagaggag gtggggaagc gggctgatag tgcccctgg    60 tgcccagtgg acgtgcccct gacttgcctc cctcttttcc agcaatgcct cctgcaccac   120
caactgcttg gccccctgg ccaaggtcat ccatgaccac tttggcatcg tggagggact   180
tatgg                                                                185
```

<210> SEQ ID NO 493
<211> LENGTH: 185
<212> TYPE: DNA
<213> ORGANISM: Bubalus bubalis

<400> SEQUENCE: 493

```
agattgtcag gtgagcgcag cagagaggag gtggggaagc gggctgatag tgcccctgg    60 tgcccagtgg acgtgcccct gacttgcctc cctcttttcc agcaatgcct cctgcaccac   120
caactgcttg gccccctgg ccaaggtcat ccatgaccac tttggcatcg tggagggact   180
tatgg                                                                185
```

<210> SEQ ID NO 494
<211> LENGTH: 185
<212> TYPE: DNA
<213> ORGANISM: Bos indicus

<400> SEQUENCE: 494

```
agattgtcag gtgagcgcag cagagaggag gtggggaagc gggctgatag tgcccctgg    60 tgcccagtgg acgtgcccct gacttgcctc cctcttttcc agcaatgcct cctgcaccac   120
caactgcttg gccccctgg ccaaggtcat ccatgaccac tttggcatcg tggagggact   180
tatgg                                                                185
```

<210> SEQ ID NO 495
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 495

```
ctcctgcgac ttcaacagcg acactcactc ttctaccttc gatgctgggg ctggcattgc    60
cctcaacgac cactttgtca agctcatttc ctggtatgtg gggggtgggg gtggggtgg   120 gatgatgctt cagcatgtgg tctggtgccc cctggtggct ggctcggtaa ac           172
```

<210> SEQ ID NO 496
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (113)..(118)
<223> OTHER INFORMATION: a, c, t, g, unknown or other

<400> SEQUENCE: 496
ctcctgcgac ttcaacagcg acactcactc ttctaccttc gatgctgggg ctggcattgc        60
cctcaacgac cactttgtca agctcatttc ctggtatgtg ggggntgggg gcnnnnnngg       120
gatgatgctt cagcatgtga tctggtgccc cctggtggct ggctcggtaa ac              172

<210> SEQ ID NO 497
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 497
ctcctgcgac ttcaacagcg acactcactc ttctaccttc gatgctgggg ctggcattgc        60
cctcaacgac cactttgtca agctcatttc ctggtatgtg ggggtgggg gtggggtgg        120 gatgatgctt cagcatgtgg tctggtgccc cctggtggct ggctcggtaa ac              172

<210> SEQ ID NO 498
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (111)..(112)
<223> OTHER INFORMATION: a, c, t, g, unknown or other

<400> SEQUENCE: 498
cgacaatgaa ttcggctaca gcaacagggt ggtggacctc atggtccaca tggcctccaa        60
ggagtaaggt ccctggaccc ccagccccag caggagcacg agaggaagag nnttcctcag       120
ctg                                                                    123

<210> SEQ ID NO 499
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 499
cgacaatgaa ttcggctaca gcaacagggt ggtggacctc atggtccaca tggcctccaa        60
ggagtaaggt ccctggaccc tcagccccag caggagcatg agaggaagag agttcctccg       120
ctg                                                                    123

<210> SEQ ID NO 500
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (111)..(112)
<223> OTHER INFORMATION: a, c, t, g, unknown or other

<400> SEQUENCE: 500
cgacaatgaa tttggctaca gcaacagggt ggtggacctc atggtccaca tggcctccaa    60
ggagtaaggt ccctggaccc ccagccccag caggagcacg agaggaagag nnttcctcag   120
ctg                                                                 123

<210> SEQ ID NO 501
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
gaagacccat gatgcaaagt cctaggacaa ggcctagaaa atcaacgatg ggagcacttt    60
atgctgtagg aggcatggat gctatgaaag g                                   91

<210> SEQ ID NO 502
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
gaagacccat gatgcaaagt cctaggacaa ggcctagaaa atcaaccatg ggagcacttt    60
atgctgtagg aggcatggat gctatgaaag g                                   91

<210> SEQ ID NO 503
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
gaagacccat gatgcaaagt cctaggacaa ggcctagaaa atcaacgatg ggagcacttt    60
atgctgtagg aggcatggat gctatgaaag g                                   91

<210> SEQ ID NO 504
<211> LENGTH: 178
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (131)..(131)
<223> OTHER INFORMATION: a, c, t, g, unknown or other

<400> SEQUENCE: 504
gtggttggag gatatgatgg acatacttat ttgcacactg ttgaatcgta tgatgcacag    60
aaagatgaat ggagagaggt actcttaatt taagtatcca aattgatata tttcagggtt   120
taactcaaaa nttaaaatat atatttggaa ttcatcccat tctcttccac tctagggc     178

<210> SEQ ID NO 505

```
<211> LENGTH: 178
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 505
gtggttggag gatatgatgg acatacttat ttgaacactg ttgaatcgta tgatgcacag    60
aaagatgaat ggagagaggt actcttaatt taagtatcca aattgatata tttcaggttt   120
taactcaaaa attaaaatat atatttggaa ttcatcccat tctcttccac tctagggc     178

<210> SEQ ID NO 506
<211> LENGTH: 178
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (131)..(131)
<223> OTHER INFORMATION: a, c, t, g, unknown or other

<400> SEQUENCE: 506
gtggttggag gatatgatgg acatacttat ttgcacactg ttgaatcgta tgatgcacag    60
aaagatgaat ggagagaggt actcttaatt taagtatcca aattgatata tttcagggtt   120
taactcaaaa nttaaaatat atatttggaa ttcatcccat tctcttccac tctagggc     178

<210> SEQ ID NO 507
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (114)..(118)
<223> OTHER INFORMATION: a, c, t, g, unknown or other

<400> SEQUENCE: 507
gcacagaaag atgaatggag agaggtactc ttaatttaag tatccaaatt gatatatttc    60
agggtttaac tcaaaantta aaatatatat ttggaattca tcccattctc ttcnnnnnta   120
gggctgaatc aaattacttt agtg                                          144

<210> SEQ ID NO 508
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 508
gcacagaaag atgaatggag agaggtactc ttaatttaag tatccaaatt gatatatttc    60
aggttttaac tcaaaaatta aaatatatat ttggaattca tcccattctc ttccactcta   120
```

```
gggctgaatc aaattacttt agtg                                          144
```

<210> SEQ ID NO 509
<211> LENGTH: 144
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (114)..(118)
<223> OTHER INFORMATION: a, c, t, g, unknown or other

<400> SEQUENCE: 509

```
gcacagaaag atgaatggag agaggtactc ttaatttaag tatccaaatt gatatatttc    60
agggtttaac tcaaaantta aaatatatat ttggaattca tcccattctc ttcnnnnnta   120
gggctgaatc aaattacttt agtg                                          144
```

<210> SEQ ID NO 510
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 510

```
gcacactcac taggagaaac aaaccatatt ctcacactta tgccccttc agactggcta     60 cacagcatgc tgaagacatg agtgttagca gatttgagga gcagttcca              109
```

<210> SEQ ID NO 511
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 511

```
gcacactcac taggagaaac aaaccatatt ctcacacttt tccccctttc agactggcta    60
cacagcatgc tgaagacatg agtgttagca gatttgagga gcagttcca              109
```

<210> SEQ ID NO 512
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 512

```
gcacactcac taggagaaac aaaccatatt ctcacactta tgccccttc agactggcta     60 cacagcatgc tgaagacatg agtgttagca gatttgagga gcagttcca              109
```

<210> SEQ ID NO 513

```
<211> LENGTH: 89
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
cagtgatgcc tcccatgtca acacacaggc atggtttagg taagagctta atgttgtata      60
gtttctaaag actgtacatt tactagagc                                        89

<210> SEQ ID NO 514
<211> LENGTH: 89
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
cagtgatgcc tcccatgtca acacacaggc atggtttagg taagagctta atgttgtata      60
gtttctaaag actgtgcatt tactagagc                                        89

<210> SEQ ID NO 515
<211> LENGTH: 89
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
cagtgatgcc tcccatgtca acacacaggc atggtttagg taagagctta atgttgtata      60
gtttctaaag actgtacatt tactagagc                                        89

<210> SEQ ID NO 516
<211> LENGTH: 83
<212> TYPE: DNA
<213> ORGANISM: Bos taurus

<400> SEQUENCE: 516
ggcatgatgt gcaggctagg caacaagacc tagcaatgct gctttcttac atcagattgc      60
cgttacttcc accacaggta tgg                                              83

<210> SEQ ID NO 517
<211> LENGTH: 83
<212> TYPE: DNA
<213> ORGANISM: Bubalus bubalis

<400> SEQUENCE: 517
ggcatgatgt gcaggctagg caacaagacc tagcaatgct gctttcttac atcagattgc      60
cgttacttcc accacaggta tgg                                              83

<210> SEQ ID NO 518
<211> LENGTH: 83
<212> TYPE: DNA
<213> ORGANISM: Bos indicus

<400> SEQUENCE: 518
ggcatgatgt gcaggctagg caacaagacc tagcaatgct gctttcttac atcagattgc      60
```
cgttacttcc accacaggta tgg                                           83

<210> SEQ ID NO 519
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 519
ttaagccggt cacagtccgt gatcataacc aattcactcc tgcaaaagga gcatcacagc    60
agctggacaa gcctgggcca caataaggta acattggcta cacggatttc ggcggacttt   120
ccctktaaca aaagcttaga gcctggactt tcttgtgctt attttcaata ttgacttcct   180
tactctcgct aacaaaggcg ctctttatct c                                  211

<210> SEQ ID NO 520
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 520
ttaagccggt cacagtccgt gatcataacc aattcactcc tgcaaaagga gcatcacagc    60
agctggacaa gcctgggcca caatagggta acattggcta cacggatttc ggaggacttt   120
ccctttaaca aaagcttaga gcctggactt tcttgtgctt attttcaata ttgacttcct   180
tactctcgct ctcaaaggca ctctttatct c                                  211

<210> SEQ ID NO 521
<211> LENGTH: 211
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 521
ttaagccggt cacagtccgt gatcataacc aattcactcc tgcaaaagga gcatcacagc    60
agctggacaa gcctgggcca caataaggta acattggcta cacggatttc ggcggacttt   120
ccctttaaca aaagcttaga gcctggactt tcttgtgctt attttcaata ttgacttcct   180
tactctcgct aacaaaggcg ctctttatct c                                  211

<210> SEQ ID NO 522
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 522
cctgggccac aataaggtaa cattggctac acggatttcg gcggactttc cctgtaacaa    60
aagcttagag cctggacttt cttgtgctta ttttcaatat tgacttcctt actctcgcta   120
acaaaggcgc 130

<210> SEQ ID NO 523
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 523
cctgggccac aatagggtaa cattggctac acggatttcg gaggactttc cctttaacaa    60
aagcttagag cctggacttt cttgtgctta ttttcaatat tgacttcctt actctcgctc   120
tcaaaggcac                                                          130

<210> SEQ ID NO 524
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 524
cctgggccac aataaggtaa cattggctac acggatttcg gcggactttc cctttaacaa    60
aagcttagag cctggacttt cttgtgctta ttttcaatat tgacttcctt actctcgcta   120
acaaaggcgc                                                          130

<210> SEQ ID NO 525
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 525
cttactctcg ctaacaaagg cgctctttat ctcaatttta ctacagtttc acctgcgact    60 taatttata agaagcccaa taagtaagta catttaacat gtaaagaatt cagactttcc   120
aatataactg gtcctctgtt aatcagttct ttctataaga gtactttttt gtaaaaaatt   180
atcttaacag caccaaaact gcttgagttc                                    210

<210> SEQ ID NO 526
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 526
cttactctcg ctctcaaagg cactctttat ctcaatttta ctacaatttc acctgcgact    60
taattttaaa agaagcccaa taagtaagta catttaacat gtaaaggatt cagactttcc   120
aatataattg gtcctctgtt aatcagttct ttctgtaaga gtactttttt gtaaaaaatt   180
atcttaacag caccaaaact gcttgagttc                                    210

```
<210> SEQ ID NO 527
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 527
cttactctcg ctaacaaagg cgctctttat ctcaattta ctacagtttc acctgcgact      60
taattttata agaagcccaa taagtaagta catttaacat gtaaagaatt cagactttcc    120
aatataactg gtcctctgtt aaycagttct ttctataaga gtacttttt gtaaaaaatt    180 atcttaacag caccaaaact gcttgagttc                                     210

<210> SEQ ID NO 528
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 528
cagtgcagtc gtatgcttct gctatgttca gagtattgaa cgacgatgtt tacagtccag     60
ctgtggtaca gcaacaaact actctcgctt ttaggaaaga ctcttccttg tgcacagac    119

<210> SEQ ID NO 529
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 529
cagtgcagtc gtatgcttct gctatgttca gagtattgaa cgacgatgtt tacagtccag     60
cggtggtaca gcaacaaaat attctcgctt ttaggaaaga ctcttcctcg tgcacagac    119

<210> SEQ ID NO 530
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 530
cagtgcagtc gtatgcttct gctatgttca gagtattgaa cgacgatgtt tacagtccag     60
ctgtggtaca gcaacaaact actctcgctt ttaggaaaga ctcttccttg tgcacagac    119

<210> SEQ ID NO 531
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
```

```
caccgcatat tacttcctcc cctttaaaac agtgcagtcg tatgcttctg ctatgttcag    60
agtattgaac gacgatgttt acagtc                                        86
```

<210> SEQ ID NO 532
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532

```
caccgcatat tatttcctcc tcttttaaac agtgcagtcg tatgcttctg ctatgttcag    60
agtattgaac gacgatgttt acagtc                                        86
```

<210> SEQ ID NO 533
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533

```
caccgcatat tacttcctcc cctttaaaac agtgcagtcg tatgcttctg ctatgttcag    60
agtattgaac gacgatgttt acagtc                                        86
```

<210> SEQ ID NO 534
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534

```
gattgtttga gtaggaccac atattggtca tcttggtatg tccagttcct ggaaagtaaa    60
atattaataa cactgaggac gtggtacctg tg                                 92
```

<210> SEQ ID NO 535
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535

```
gattgtttga gcaggaccac atattggtca tcttggtatg tccagttcct ggaaaataaa    60
atattaataa cactgaggac gtggtacctg tg                                 92
```

<210> SEQ ID NO 536
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
gattgtttga gtaggaccac atattggtca tcttggtatg tccagttcct ggaaagtaaa    60
atattaataa cactgaggac gtggtacctg tg    92

<210> SEQ ID NO 537
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 537
gaggagcctt catactagac actctaagat tgtttgagta ggaccacata ttggtcatct    60
tggtatgtcc agttcctgga aagtaaaata ttaataacac tgaggacgtg gtacctg    117

<210> SEQ ID NO 538
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 538
gaggagcctt catactagac actctaagat tgtttgagca ggaccacata ttggtcatct    60
tggtatgtcc agttcctgga aaataaaata ttaataacac tgaggacgtg gtacctg    117

<210> SEQ ID NO 539
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 539
gaggagcctt catactagac actctaagat tgtttgagta ggaccacata ttggtcatct    60
tggtatgtcc agttcctgga aagtaaaata ttaataacac tgaggacgtg gtacctg    117

<210> SEQ ID NO 540
<211> LENGTH: 155
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 540
cttgctctga gcctcatccc ccacgtacga gtccttctgg cccatgccca ccattacgcc    60
ctgcggagag aggagcgagg aggcgccttc agctccggcc aagtcccacc gacccccacc    120
acccacccag aaagccaaaa aggcctccct ccacc    155

<210> SEQ ID NO 541
<211> LENGTH: 155
<212> TYPE: DNA
<213> ORGANISM: Artificial Sequence
<220> FEATURE:
<221> NAME/KEY: source
<223> OTHER INFORMATION: /note="Description of Artificial Sequence:

```
       Synthetic polynucleotide"
<220> FEATURE:
<221> NAME/KEY: modified_base
<222> LOCATION: (65)..(66)
<223> OTHER INFORMATION: a, c, t, g, unknown or other

<400> SEQUENCE: 541
cttgctctga gcctcatccc ccacgtacga gtccttctgg cccatgccca ccattacgcc      60
ctgcnnagag aggagcgagg aggcgccttc agctacggcc aagtcccacc gacccccacc     120
acccacccag aaagcctaaa aggcctccct tcacc                                155

<210> SEQ ID NO 542
<211> LENGTH: 155
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 542
cttgctctga gcctcatccc ccacgtacga gtccttctgg cccatgccca ccattacgcc      60
ctgcggagag aggagcgagg aggcgccttc agctccggcc aagtcccacc gacccccacc     120
acccacccag aaagccaaaa aggcctccct ccacc                                155

<210> SEQ ID NO 543
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 543
gacttagcct ccagtgtggc cacagggtga ccttcgtgtg gggcaggcag ggcgggcctt      60
ctcactcacc caggaaggaa ggctggaaga gagcc                                 95

<210> SEQ ID NO 544
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 544
gacttagcct ccagtgtggc cacagggtga ccttcgtgtg gggcgggcag ggcgggcctt      60
ctcactcacc caggaaggaa ggctggaaga gagcc                                 95

<210> SEQ ID NO 545
<211> LENGTH: 95
<212> TYPE: DNA
<213> ORGANISM: Bos indicus

<400> SEQUENCE: 545
gacttagcct ccagtgtggc cacagggtga ccttcgtgtg gggcgggcag ggcgggcctt      60
ctcactcacc caggaaggaa ggctggaaga gagcc                                 95

<210> SEQ ID NO 546
<211> LENGTH: 108
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 546
ccagggacct tactccttgg aggccatgtg gaccatgagg tccaccaccc tgttgctgta    60
gccaaattca ttgtcgtacc tggaaggaga gtgtgaaggg ctgtttac               108

<210> SEQ ID NO 547
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
gacgacatgg agaagatctg gc                                            22

<210> SEQ ID NO 548
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(5)
<223> OTHER INFORMATION: a, c, t, g, unknown or other

<400> SEQUENCE: 548
ccnnnctttg cctcaccctt tctcact                                       27

<210> SEQ ID NO 549
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
taggactttc ttctctgagc tga                                           23

<210> SEQ ID NO 550
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
gacgacatgg agaagatctg gc                                            22

<210> SEQ ID NO 551
<211> LENGTH: 27
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 551
cctttctttg ccacgccctt tctcact                                       27

<210> SEQ ID NO 552
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
taggactttc ttctctgagc tga                                           23

<210> SEQ ID NO 553
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
gacgacatgg agaagatctg gc                                            22

<210> SEQ ID NO 554
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(5)
<223> OTHER INFORMATION: a, c, t, g, unknown or other

<400> SEQUENCE: 554
ccnnnctttg cctcaccctt tctcact                                       27

<210> SEQ ID NO 555
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
taggactttc ttctctgagc tga                                           23

<210> SEQ ID NO 556
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
```

```
ccataagtcc ctccacgatg                                              20

<210> SEQ ID NO 557
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
gttggtggtg caggaggcat tg                                           22

<210> SEQ ID NO 558
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
ctgcgctcac ctgacaatct                                              20

<210> SEQ ID NO 559
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
ccataagtcc ctccacgatg                                              20

<210> SEQ ID NO 560
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
gttggtggtg caggaggcat tg                                           22

<210> SEQ ID NO 561
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
ctgcgctcac ctgacaatct                                              20

<210> SEQ ID NO 562
<211> LENGTH: 20
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 562
ccataagtcc ctccacgatg                                                    20

<210> SEQ ID NO 563
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
gttggtggtg caggaggcat tg                                                 22

<210> SEQ ID NO 564
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
ctgcgctcac ctgacaatct                                                    20

<210> SEQ ID NO 565
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
ggaagcgggc tgatagtg                                                      18

<210> SEQ ID NO 566
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
caatgcctcc tgcaccacca ac                                                 22

<210> SEQ ID NO 567
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
catcgtggag ggacttatgg                                                    20

```
<210> SEQ ID NO 568
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
agattgtcag gtgagcgcag                                                    20

<210> SEQ ID NO 569
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
caatgcctcc tgcaccacca ac                                                 22

<210> SEQ ID NO 570
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
atccatgacc actttggca                                                     19

<210> SEQ ID NO 571
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
cagcatgaag atggccctg                                                     19

<210> SEQ ID NO 572
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 572
gtcacccagt ngnncctrca tcc                                                23

<210> SEQ ID NO 573
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
cagcatgaag atggccctg                                              19

<210> SEQ ID NO 574
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(4)
<223> OTHER INFORMATION: a, c, t, g, unknown or other

<400> SEQUENCE: 574
gtgncccagt agtgcctaca tcc                                         23

<210> SEQ ID NO 575
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
cagcatgaag atggccctg                                              19

<210> SEQ ID NO 576
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 576
gtcacccagt ngnncctaca tcc                                         23

<210> SEQ ID NO 577
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
tatgcttgcc cacggaagcc                                             20
```

<210> SEQ ID NO 578
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 578
cgctgcattg ctgaacgatc                                                  20

<210> SEQ ID NO 579
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 579
tatgctcgac cacggaagcc                                                  20

<210> SEQ ID NO 580
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 580
ttggatttgg tgggtgtgtt gca                                              23

<210> SEQ ID NO 581
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 581
cgctgcattg ctgaacgatc                                                  20

<210> SEQ ID NO 582
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 582
tatgcttgac cacggaagcc                                                  20

<210> SEQ ID NO 583
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 583
cgctgcattg ctgaacgatc                                          20

<210> SEQ ID NO 584
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
ctttctacct gctgtcccac g                                        21

<210> SEQ ID NO 585
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
agctgccgag tgaaacacgt tact                                     24

<210> SEQ ID NO 586
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
gggaatgtka ttaaacctct gcgta                                    25

<210> SEQ ID NO 587
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
ctttctacct gctgtcccac g                                        21

<210> SEQ ID NO 588
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
agctgccgag tgaaacacgt tact                                     24

<210> SEQ ID NO 589
<211> LENGTH: 21

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
ctttctacct gctgtcccac g                                                    21

<210> SEQ ID NO 590
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
agctgccgag tgaaacacgt tact                                                 24

<210> SEQ ID NO 591
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
gggaatgtka ttaaacctct gcrta                                                25

<210> SEQ ID NO 592
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
tttgaacaga ctgatggttc cc                                                   22

<210> SEQ ID NO 593
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
acatccttag agctggaact tggcc                                                25

<210> SEQ ID NO 594
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
```

```
gcgagggtga cacttcttg                                              19
```

<210> SEQ ID NO 595
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595

```
ttcgaacaga ctgatggttc cc                                          22
```

<210> SEQ ID NO 596
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596

```
acgtccttag agctggaact tggcc                                       25
```

<210> SEQ ID NO 597
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597

```
gcgagggtga cacttcttg                                              19
```

<210> SEQ ID NO 598
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598

```
tttgaacaga ctgatggttc cc                                          22
```

<210> SEQ ID NO 599
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599

```
acatccttag agctggaact tggcc                                       25
```

<210> SEQ ID NO 600
<211> LENGTH: 19
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 600
gcgagggtga cacttcttg                                                19

<210> SEQ ID NO 601
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
ttacctgaga gaagacccat gatgc                                         25

<210> SEQ ID NO 602
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
gggagcactt tatgctgtag gag                                           23

<210> SEQ ID NO 603
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
ttacctgaga gaagacccat gatgc                                         25

<210> SEQ ID NO 604
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
gggagcactt tatgctgtag gag                                           23

<210> SEQ ID NO 605
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
ttacctgaga gaagacccat gatgc                                         25

<210> SEQ ID NO 606
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
gggagcactt tatgctgtag gag                                                  23

<210> SEQ ID NO 607
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
gcacactcac taggagaaac aaacc                                                25

<210> SEQ ID NO 608
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
ccctttcaga ctggctacac agca                                                 24

<210> SEQ ID NO 609
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
gcagatttga ggagcagttc ca                                                   22

<210> SEQ ID NO 610
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
gcacactcac taggagaaac aaacc                                                25

<210> SEQ ID NO 611
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
```

```
ccctttcaga ctggctacac agca                                              24
```

<210> SEQ ID NO 612
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612

```
gcagatttga ggagcagttc ca                                                22
```

<210> SEQ ID NO 613
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613

```
gcacactcac taggagaaac aaacc                                             25
```

<210> SEQ ID NO 614
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614

```
ccctttcaga ctggctacac agca                                              24
```

<210> SEQ ID NO 615
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615

```
gcagatttga ggagcagttc ca                                                22
```

<210> SEQ ID NO 616
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616

```
gcacactcac taggagaaac aaacc                                             25
```

<210> SEQ ID NO 617
<211> LENGTH: 24
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 617
ccctttcaga ctggctacac agca                                            24

<210> SEQ ID NO 618
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
ctcattgctg gacatctccg                                                 20

<210> SEQ ID NO 619
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
ccactggata tttgcacact cac                                             23

<210> SEQ ID NO 620
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
ccctttcaga ctggctacac agca                                            24

<210> SEQ ID NO 621
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
gcagatttga ggagcagttc ca                                              22

<210> SEQ ID NO 622
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
gactcaagtc attgaagtct gctcc                                           25
```

```
<210> SEQ ID NO 623
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
gcccaaggct gtacaaagct c                                              21

<210> SEQ ID NO 624
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
gactcaagtc attgaagtct gctcc                                          25

<210> SEQ ID NO 625
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
agctccaccc ttcaaactgc ttagg                                          25

<210> SEQ ID NO 626
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
gcccaaggct gtacaaagct c                                              21

<210> SEQ ID NO 627
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
gactcaagtc attgaagtct gctcc                                          25

<210> SEQ ID NO 628
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 628
gcccaaggct gtacaaagct c                                              21

<210> SEQ ID NO 629
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
agagaagacc catgatgcaa agtcc                                          25

<210> SEQ ID NO 630
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
tcaacgatgg gagcacttta tgctgt                                         26

<210> SEQ ID NO 631
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
ggaggcatgg atgctatgaa agg                                            23

<210> SEQ ID NO 632
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
agagaagacc catgatgcaa agtcc                                          25

<210> SEQ ID NO 633
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
tcaaccatgg gagcacttta tgctgt                                         26

<210> SEQ ID NO 634
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 634
ggaggcatgg atgctatgaa agg                                              23

<210> SEQ ID NO 635
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
agagaagacc catgatgcaa agtcc                                            25

<210> SEQ ID NO 636
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
tcaacgatgg gagcacttta tgctgt                                           26

<210> SEQ ID NO 637
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
ggaggcatgg atgctatgaa agg                                              23

<210> SEQ ID NO 638
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
agagaagacc catgatgcaa agtcc                                            25

<210> SEQ ID NO 639
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
tcaacgatgg gagcacttta tgctgt                                           26
```

<210> SEQ ID NO 640
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
ctcttgctgc tgctaagtca cgtc                                              24

<210> SEQ ID NO 641
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
cagctccatg tttactggtg atc                                               23

<210> SEQ ID NO 642
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
tcaacgatgg gagcacttta tgctgt                                            26

<210> SEQ ID NO 643
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
ggaggcatgg atgctatgaa agg                                               23

<210> SEQ ID NO 644
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
gaactcaagc agttttggtg c                                                 21

<210> SEQ ID NO 645
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
ttaagtcgca ggtgaaactg tagt                                          24

<210> SEQ ID NO 646
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
cgcctttgtt agcgagagta ag                                            22

<210> SEQ ID NO 647
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
gaactcaagc agttttggtg c                                             21

<210> SEQ ID NO 648
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
ttaagtcgca ggtgaaattg tagt                                          24

<210> SEQ ID NO 649
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
tgcctttgag agcgagagta ag                                            22

<210> SEQ ID NO 650
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
gaactcaagc agttttggtg c                                             21

<210> SEQ ID NO 651
<211> LENGTH: 24
<212> TYPE: DNA

-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
ttaagtcgca ggtgaaactg tagt                                              24

<210> SEQ ID NO 652
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
cgcctttgtt agcgagagta ag                                                22

<210> SEQ ID NO 653
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
ttactctcgc taacaaaggc g                                                 21

<210> SEQ ID NO 654
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
gcaccaaaac tgcttgagtt                                                   20

<210> SEQ ID NO 655
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
ttactctcgc tctcaaaggc a                                                 21

<210> SEQ ID NO 656
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
gcaccaaaac tgcttgagtt                                                   20

<210> SEQ ID NO 657
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
ttactctcgc taacaaaggc g                                            21

<210> SEQ ID NO 658
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
gcaccaaaac tgcttgagtt                                              20

<210> SEQ ID NO 659
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
aattcggcca gtgtcaggc                                               19

<210> SEQ ID NO 660
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
cattgtaacc gatgtgccta aagc                                         24

<210> SEQ ID NO 661
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
gcgattgttt ccgcgagaaa tagag                                        25

<210> SEQ ID NO 662
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

```
                     Synthetic oligonucleotide"

<400> SEQUENCE: 662
aattcggcca gtgtcaggc                                               19

<210> SEQ ID NO 663
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
cattgtaacc gatgtgccta aagc                                         24

<210> SEQ ID NO 664
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
gcgagagttt ccgtgagaaa tagag                                        25

<210> SEQ ID NO 665
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
gagataaaga gcgcctttgt tagcg                                        25

<210> SEQ ID NO 666
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
cgaaatccgt gtagccaatg ttac                                         24

<210> SEQ ID NO 667
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
cggactgtga ccggcttaa                                               19

<210> SEQ ID NO 668
<211> LENGTH: 20
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 668
agattgtcag gtgagcgcag                                            20

<210> SEQ ID NO 669
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 669
caatgcctcc tgcaccacca ac                                         22

<210> SEQ ID NO 670
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 670
catcgtggag ggacttatgg                                            20

<210> SEQ ID NO 671
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 671
agattgtcag gtgagcgcag                                            20

<210> SEQ ID NO 672
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 672
caatgcctcc tgcaccacca ac                                         22

<210> SEQ ID NO 673
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 673

```
catcgtggag ggacttatgg                                            20
```

<210> SEQ ID NO 674
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674

```
agattgtcag gtgagcgcag                                            20
```

<210> SEQ ID NO 675
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675

```
caatgcctcc tgcaccacca ac                                         22
```

<210> SEQ ID NO 676
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676

```
catcgtggag ggacttatgg                                            20
```

<210> SEQ ID NO 677
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677

```
ctcctgcgac ttcaacagcg                                            20
```

<210> SEQ ID NO 678
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678

```
ttgccctcaa cgaccacttt gtca                                       24
```

<210> SEQ ID NO 679
<211> LENGTH: 19
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 679
ggtggctggc tcggtaaac                                                    19

<210> SEQ ID NO 680
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
ctcctgcgac ttcaacagcg                                                   20

<210> SEQ ID NO 681
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
ttgccctcaa cgaccacttt gtca                                              24

<210> SEQ ID NO 682
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
ggtggctggc tcggtaaac                                                    19

<210> SEQ ID NO 683
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
ctcctgcgac ttcaacagcg                                                   20

<210> SEQ ID NO 684
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
ttgccctcaa cgaccacttt gtca                                              24

<210> SEQ ID NO 685
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
ggtggctggc tcggtaaac                                                  19

<210> SEQ ID NO 686
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
cgacaatgaa ttcggctaca g                                               21

<210> SEQ ID NO 687
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
tcatggtcca catggcctcc aag                                             23

<210> SEQ ID NO 688
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(8)
<223> OTHER INFORMATION: a, c, t, g, unknown or other

<400> SEQUENCE: 688
gaagagnntt cctcagctg                                                  19

<210> SEQ ID NO 689
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
cgacaatgaa ttcggctaca g                                               21

<210> SEQ ID NO 690
<211> LENGTH: 23
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 690
tcatggtcca catggcctcc aag                                               23

<210> SEQ ID NO 691
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
gaagagagtt cctccgctg                                                    19

<210> SEQ ID NO 692
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
cgacaatgaa tttggctaca g                                                 21

<210> SEQ ID NO 693
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
tcatggtcca catggcctcc aag                                               23

<210> SEQ ID NO 694
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(8)
<223> OTHER INFORMATION: a, c, t, g, unknown or other

<400> SEQUENCE: 694
gaagagnntt cctcagctg                                                    19

<210> SEQ ID NO 695
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
```

```
gaagacccat gatgcaaagt cc                                            22
```

<210> SEQ ID NO 696
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696

```
tcaacgatgg gagcacttta tgctgt                                        26
```

<210> SEQ ID NO 697
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697

```
ggaggcatgg atgctatgaa agg                                           23
```

<210> SEQ ID NO 698
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698

```
gaagacccat gatgcaaagt cc                                            22
```

<210> SEQ ID NO 699
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699

```
tcaaccatgg gagcacttta tgctgt                                        26
```

<210> SEQ ID NO 700
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700

```
ggaggcatgg atgctatgaa agg                                           23
```

<210> SEQ ID NO 701
<211> LENGTH: 22
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 701
gaagacccat gatgcaaagt cc                                            22

<210> SEQ ID NO 702
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
tcaacgatgg gagcacttta tgctgt                                        26

<210> SEQ ID NO 703
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
ggaggcatgg atgctatgaa agg                                           23

<210> SEQ ID NO 704
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
gtggttggag gatatgatgg ac                                            22

<210> SEQ ID NO 705
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
tgcacagaaa gatgaatgga gagaggt                                       27

<210> SEQ ID NO 706
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
ccattctctt ccactctagg gc                                            22

<210> SEQ ID NO 707
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
gtggttggag gatatgatgg ac                                              22

<210> SEQ ID NO 708
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
tgcacagaaa gatgaatgga gagaggt                                         27

<210> SEQ ID NO 709
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
ccattctctt ccactctagg gc                                              22

<210> SEQ ID NO 710
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
gtggttggag gatatgatgg ac                                              22

<210> SEQ ID NO 711
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
tgcacagaaa gatgaatgga gagaggt                                         27

<210> SEQ ID NO 712
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
```

```
ccattctctt ccactctagg gc                                          22

<210> SEQ ID NO 713
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
gcacagaaag atgaatggag ag                                          22

<210> SEQ ID NO 714
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (23)..(27)
<223> OTHER INFORMATION: a, c, t, g, unknown or other

<400> SEQUENCE: 714
tggaattcat cccattctct tcnnnnnt                                    28

<210> SEQ ID NO 715
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715
gggctgaatc aaattacttt agtg                                        24

<210> SEQ ID NO 716
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
gcacagaaag atgaatggag ag                                          22

<210> SEQ ID NO 717
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
tggaattcat cccattctct tccactct                                    28

<210> SEQ ID NO 718
```

```
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
gggctgaatc aaattacttt agtg                                          24

<210> SEQ ID NO 719
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
gcacagaaag atgaatggag ag                                            22

<210> SEQ ID NO 720
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (23)..(27)
<223> OTHER INFORMATION: a, c, t, g, unknown or other

<400> SEQUENCE: 720
tggaattcat cccattctct tcnnnnnt                                      28

<210> SEQ ID NO 721
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
gggctgaatc aaattacttt agtg                                          24

<210> SEQ ID NO 722
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
gcacactcac taggagaaac aaacc                                         25

<210> SEQ ID NO 723
<211> LENGTH: 24
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 723
ccctttcaga ctggctacac agca                                           24

<210> SEQ ID NO 724
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
gcagatttga ggagcagttc ca                                             22

<210> SEQ ID NO 725
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
gcacactcac taggagaaac aaacc                                          25

<210> SEQ ID NO 726
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
ccctttcaga ctggctacac agca                                           24

<210> SEQ ID NO 727
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
gcagatttga ggagcagttc ca                                             22

<210> SEQ ID NO 728
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
gcacactcac taggagaaac aaacc                                          25

<210> SEQ ID NO 729
```

```
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
ccctttcaga ctggctacac agca                                          24

<210> SEQ ID NO 730
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
gcagatttga ggagcagttc ca                                            22

<210> SEQ ID NO 731
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
cagtgatgcc tcccatgtc                                                19

<210> SEQ ID NO 732
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
acaggcatgg tttaggtaag agct                                          24

<210> SEQ ID NO 733
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
gactgtacat ttactagagc                                               20

<210> SEQ ID NO 734
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
```
cagtgatgcc tcccatgtc                                               19

<210> SEQ ID NO 735
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
acaggcatgg tttaggtaag agct                                         24

<210> SEQ ID NO 736
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 736
gactgtgcat ttactagagc                                              20

<210> SEQ ID NO 737
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
cagtgatgcc tcccatgtc                                               19

<210> SEQ ID NO 738
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
acaggcatgg tttaggtaag agct                                         24

<210> SEQ ID NO 739
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
gactgtacat ttactagagc                                              20

<210> SEQ ID NO 740
<211> LENGTH: 19
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 740
ggcatgatgt gcaggctag                                                    19

<210> SEQ ID NO 741
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
gcaacaagac ctagcaatgc tgct                                              24

<210> SEQ ID NO 742
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
gttacttcca ccacaggtat gg                                                22

<210> SEQ ID NO 743
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
ggcatgatgt gcaggctag                                                    19

<210> SEQ ID NO 744
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
gcaacaagac ctagcaatgc tgct                                              24

<210> SEQ ID NO 745
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
gttacttcca ccacaggtat gg                                                22
```

```
<210> SEQ ID NO 746
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
ggcatgatgt gcaggctag                                                  19

<210> SEQ ID NO 747
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
gcaacaagac ctagcaatgc tgct                                            24

<210> SEQ ID NO 748
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
gttacttcca ccacaggtat gg                                              22

<210> SEQ ID NO 749
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
ttaagccggt cacagtccg                                                  19

<210> SEQ ID NO 750
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
gtaacattgg ctacacggat ttcg                                            24

<210> SEQ ID NO 751
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 751
cgctaacaaa ggcgctcttt atctc                                         25

<210> SEQ ID NO 752
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752
ttaagccggt cacagtccg                                                19

<210> SEQ ID NO 753
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
gtaacattgg ctacacggat ttcg                                          24

<210> SEQ ID NO 754
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
cgctctcaaa ggcactcttt atctc                                         25

<210> SEQ ID NO 755
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
ttaagccggt cacagtccg                                                19

<210> SEQ ID NO 756
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
gtaacattgg ctacacggat ttcg                                          24

<210> SEQ ID NO 757
<211> LENGTH: 25
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 757
cgctaacaaa ggcgctcttt atctc                                          25

<210> SEQ ID NO 758
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
cctgggccac aataagg                                                   17

<210> SEQ ID NO 759
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
acacggattt cggcggactt tccc                                           24

<210> SEQ ID NO 760
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
ctctcgctaa caaaggcgc                                                 19

<210> SEQ ID NO 761
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
cctgggccac aataggg                                                   17

<210> SEQ ID NO 762
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
acacggattt cggaggactt tccc                                           24
```

<210> SEQ ID NO 763
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 763
ctctcgctct caaaggcac                                                19

<210> SEQ ID NO 764
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 764
cctgggccac aataagg                                                  17

<210> SEQ ID NO 765
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 765
acacggattt cggcggactt tccc                                          24

<210> SEQ ID NO 766
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 766
ctctcgctaa caaaggcgc                                                19

<210> SEQ ID NO 767
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 767
cttactctcg ctaacaaagg cg                                            22

<210> SEQ ID NO 768
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 768
ggtcctctgt taatcagttc tttcta        26

<210> SEQ ID NO 769
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
gcaccaaaac tgcttgagtt c        21

<210> SEQ ID NO 770
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
cttactctcg ctctcaaagg ca        22

<210> SEQ ID NO 771
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
ggtcctctgt taatcagttc tttctg        26

<210> SEQ ID NO 772
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
gcaccaaaac tgcttgagtt c        21

<210> SEQ ID NO 773
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
cttactctcg ctaacaaagg cg        22

<210> SEQ ID NO 774
<211> LENGTH: 26
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
ggtcctctgt taaycagttc tttcta                                          26

<210> SEQ ID NO 775
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
gcaccaaaac tgcttgagtt c                                               21

<210> SEQ ID NO 776
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 776
cagtgcagtc gtatgcttc                                                  19

<210> SEQ ID NO 777
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
cgacgatgtt tacagtccag ctgt                                            24

<210> SEQ ID NO 778
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
ctcttccttg tgcacagac                                                  19

<210> SEQ ID NO 779
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
cagtgcagtc gtatgcttc                                                  19

<210> SEQ ID NO 780
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
cgacgatgtt tacagtccag cggt                                          24

<210> SEQ ID NO 781
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
ctcttcctcg tgcacagac                                                19

<210> SEQ ID NO 782
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
cagtgcagtc gtatgcttc                                                19

<210> SEQ ID NO 783
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
cgacgatgtt tacagtccag ctgt                                          24

<210> SEQ ID NO 784
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
ctcttccttg tgcacagac                                                19

<210> SEQ ID NO 785
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 785
caccgcatat tacttcctcc cc                                    22

<210> SEQ ID NO 786
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
acagtgcagt cgtatgcttc tgct                                  24

<210> SEQ ID NO 787
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
gtattgaacg acgatgttta cagtc                                 25

<210> SEQ ID NO 788
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
caccgcatat tatttcctcc tc                                    22

<210> SEQ ID NO 789
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
acagtgcagt cgtatgcttc tgct                                  24

<210> SEQ ID NO 790
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
gtattgaacg acgatgttta cagtc                                 25

<210> SEQ ID NO 791
<211> LENGTH: 22

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
caccgcatat tacttcctcc cc                                         22

<210> SEQ ID NO 792
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
acagtgcagt cgtatgcttc tgct                                       24

<210> SEQ ID NO 793
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 793
gtattgaacg acgatgttta cagtc                                      25

<210> SEQ ID NO 794
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794
gattgtttga gtaggaccac                                            20

<210> SEQ ID NO 795
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
ggtcatcttg gtatgtccag ttcctgg                                    27

<210> SEQ ID NO 796
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
```
gaggacgtgg tacctgtg                                              18

<210> SEQ ID NO 797
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797
gattgtttga gcaggaccac                                            20

<210> SEQ ID NO 798
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
ggtcatcttg gtatgtccag ttcctgg                                    27

<210> SEQ ID NO 799
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
gaggacgtgg tacctgtg                                              18

<210> SEQ ID NO 800
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
gattgtttga gtaggaccac                                            20

<210> SEQ ID NO 801
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
ggtcatcttg gtatgtccag ttcctgg                                    27

<210> SEQ ID NO 802
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 802
gaggacgtgg tacctgtg                                                        18

<210> SEQ ID NO 803
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 803
gaggagcctt catactagac ac                                                   22

<210> SEQ ID NO 804
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 804
ggtcatcttg gtatgtccag ttcctgg                                              27

<210> SEQ ID NO 805
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 805
cactgaggac gtggtacctg                                                      20

<210> SEQ ID NO 806
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 806
gaggagcctt catactagac ac                                                   22

<210> SEQ ID NO 807
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 807
ggtcatcttg gtatgtccag ttcctgg                                              27

<210> SEQ ID NO 808

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
cactgaggac gtggtacctg                                              20

<210> SEQ ID NO 809
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
gaggagcctt catactagac ac                                           22

<210> SEQ ID NO 810
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
ggtcatcttg gtatgtccag ttcctgg                                      27

<210> SEQ ID NO 811
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
cactgaggac gtggtacctg                                              20

<210> SEQ ID NO 812
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
cttgctctga gcctcatcc                                               19

<210> SEQ ID NO 813
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
```
cttcagctcc ggccaagtcc ca                                              22

<210> SEQ ID NO 814
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
ccaaaaaggc ctccctccac c                                               21

<210> SEQ ID NO 815
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
cttgctctga gcctcatcc                                                  19

<210> SEQ ID NO 816
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
cttcagctac ggccaagtcc ca                                              22

<210> SEQ ID NO 817
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
cctaaaaggc ctcccttcac c                                               21

<210> SEQ ID NO 818
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
cttgctctga gcctcatcc                                                  19

<210> SEQ ID NO 819
<211> LENGTH: 22
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 819
cttcagctcc ggccaagtcc ca                                            22

<210> SEQ ID NO 820
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
ccaaaaaggc ctccctccac c                                             21

<210> SEQ ID NO 821
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
gacttagcct ccagtgtggc                                               20

<210> SEQ ID NO 822
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
ggccttctca ctcacccagg aa                                            22

<210> SEQ ID NO 823
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
ggaaggctgg aagagagcc                                                19

<210> SEQ ID NO 824
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
gacttagcct ccagtgtggc                                               20
```

```
<210> SEQ ID NO 825
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
ggccttctca ctcacccagg aa                                              22

<210> SEQ ID NO 826
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
ggaaggctgg aagagagcc                                                  19

<210> SEQ ID NO 827
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
gacttagcct ccagtgtggc                                                 20

<210> SEQ ID NO 828
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
ggccttctca ctcacccagg aa                                              22

<210> SEQ ID NO 829
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
ggaaggctgg aagagagcc                                                  19

<210> SEQ ID NO 830
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 830
ccagggacct tactccttg                                                    19

<210> SEQ ID NO 831
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
caccctgttg ctgtagccaa attc                                              24

<210> SEQ ID NO 832
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
gagtgtgaag ggctgtttac                                                   20

<210> SEQ ID NO 833
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
ccagggacct tactccttg                                                    19

<210> SEQ ID NO 834
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
caccctgttg ctgtagccaa attc                                              24

<210> SEQ ID NO 835
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
gtaaacagcc cttcacactc                                                   20

<210> SEQ ID NO 836
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 836
gtcacccagt ngnncctaca tcc                                             23

<210> SEQ ID NO 837
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837
tatgcttgac cacggaagcc                                                 20

<210> SEQ ID NO 838
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
gggaatgtka ttaaaccgct gcgta                                           25

<210> SEQ ID NO 839
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
gcgaggggtg acacttcttg                                                 20

<210> SEQ ID NO 840
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 840
```
gtcacccagt ngnncctaca tcc                                    23

<210> SEQ ID NO 841
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
tatgcttgac cacggaagcc                                        20

<210> SEQ ID NO 842
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
gggaatgtka ttaaaccgct gcgta                                  25

<210> SEQ ID NO 843
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
gcgaggggtg acacttcttg                                        20

<210> SEQ ID NO 844
<211> LENGTH: 23
<212> TYPE: DNA
<213> ORGANISM: Bos taurus

<400> SEQUENCE: 844
cctttcatag catccatgcc tcc                                    23

<210> SEQ ID NO 845
<211> LENGTH: 22
<212> TYPE: DNA
<213> ORGANISM: Bos taurus

<400> SEQUENCE: 845
tggaactgct cctcaaatct gc                                     22

<210> SEQ ID NO 846
<211> LENGTH: 25
<212> TYPE: DNA
<213> ORGANISM: Bos taurus

<400> SEQUENCE: 846
ttacctgaga gaagacccat gatgc                                  25

<210> SEQ ID NO 847
<211> LENGTH: 23
<212> TYPE: DNA
<213> ORGANISM: Bos taurus

-continued

```
<400> SEQUENCE: 847
ctcctacagc ataaagtgct ccc                                            23

<210> SEQ ID NO 848
<211> LENGTH: 25
<212> TYPE: DNA
<213> ORGANISM: Bos taurus

<400> SEQUENCE: 848
gactcaagtc attgaagtct gctcc                                          25

<210> SEQ ID NO 849
<211> LENGTH: 21
<212> TYPE: DNA
<213> ORGANISM: Bos taurus

<400> SEQUENCE: 849
gagctttgta cagccttggg c                                              21

<210> SEQ ID NO 850
<211> LENGTH: 20
<212> TYPE: DNA
<213> ORGANISM: Bos taurus

<400> SEQUENCE: 850
aagcctgggc cacaataagg                                                20

<210> SEQ ID NO 851
<211> LENGTH: 24
<212> TYPE: DNA
<213> ORGANISM: Bos taurus

<400> SEQUENCE: 851
tcggcggact ttccctgtaa caaa                                           24

<210> SEQ ID NO 852
<211> LENGTH: 19
<212> TYPE: DNA
<213> ORGANISM: Bos taurus

<400> SEQUENCE: 852
aagagcgcct ttgttagcg                                                 19

<210> SEQ ID NO 853
<211> LENGTH: 20
<212> TYPE: DNA
<213> ORGANISM: Bos taurus

<400> SEQUENCE: 853
attaagccgg tcacagtccg                                                20

<210> SEQ ID NO 854
<211> LENGTH: 20
<212> TYPE: DNA
<213> ORGANISM: Bos taurus

<400> SEQUENCE: 854
aaagagcgcc tttgttagcg                                                20

<210> SEQ ID NO 855
<211> LENGTH: 24
<212> TYPE: DNA
```

```
<213> ORGANISM: Bos taurus

<400> SEQUENCE: 855
tcggcggact ttccctgtaa caaa                                              24

<210> SEQ ID NO 856
<211> LENGTH: 20
<212> TYPE: DNA
<213> ORGANISM: Bos taurus

<400> SEQUENCE: 856
gagcctggac tttcttgtgc                                                   20

<210> SEQ ID NO 857
<211> LENGTH: 22
<212> TYPE: DNA
<213> ORGANISM: Bos taurus

<400> SEQUENCE: 857
ataaagagcg cctttgttag cg                                                22

<210> SEQ ID NO 858
<211> LENGTH: 23
<212> TYPE: DNA
<213> ORGANISM: Bos taurus

<400> SEQUENCE: 858
ttcaatattg acttccttac tct                                               23

<210> SEQ ID NO 859
<211> LENGTH: 20
<212> TYPE: DNA
<213> ORGANISM: Bos taurus

<400> SEQUENCE: 859
ttggctacac ggatttcggc                                                   20

<210> SEQ ID NO 860
<211> LENGTH: 23
<212> TYPE: DNA
<213> ORGANISM: Bos taurus

<400> SEQUENCE: 860
gataaagagc gcctttgtta gcg                                               23

<210> SEQ ID NO 861
<211> LENGTH: 24
<212> TYPE: DNA
<213> ORGANISM: Bos taurus

<400> SEQUENCE: 861
aaataagcac aagaaagtcc aggc                                              24

<210> SEQ ID NO 862
<211> LENGTH: 21
<212> TYPE: DNA
<213> ORGANISM: Bos taurus

<400> SEQUENCE: 862
cattggctac acggatttcg g                                                 21

<210> SEQ ID NO 863
<211> LENGTH: 24
```

```
<212> TYPE: DNA
<213> ORGANISM: Bos taurus

<400> SEQUENCE: 863
gagataaaga gcgctttgtt agcg                                    24

<210> SEQ ID NO 864
<211> LENGTH: 20
<212> TYPE: DNA
<213> ORGANISM: Bos taurus

<400> SEQUENCE: 864
tactctcgct aacaaaggcg                                         20

<210> SEQ ID NO 865
<211> LENGTH: 21
<212> TYPE: DNA
<213> ORGANISM: Bos taurus

<400> SEQUENCE: 865
tgactcaagc agttttggtg c                                       21

<210> SEQ ID NO 866
<211> LENGTH: 24
<212> TYPE: DNA
<213> ORGANISM: Bos taurus

<400> SEQUENCE: 866
actacagttt cacctgcgac ttaa                                    24

<210> SEQ ID NO 867
<211> LENGTH: 20
<212> TYPE: DNA
<213> ORGANISM: Bos taurus

<400> SEQUENCE: 867
ttggctacac ggatttcggc                                         20

<210> SEQ ID NO 868
<211> LENGTH: 18
<212> TYPE: DNA
<213> ORGANISM: Bos taurus

<400> SEQUENCE: 868
agagcgcctt tgttagcg                                           18

<210> SEQ ID NO 869
<211> LENGTH: 24
<212> TYPE: DNA
<213> ORGANISM: Bos taurus

<400> SEQUENCE: 869
aaataagcac aagaaagtcc aggc                                    24

<210> SEQ ID NO 870
<211> LENGTH: 21
<212> TYPE: DNA
<213> ORGANISM: Bos taurus

<400> SEQUENCE: 870
gaactcaagc agttttggtg c                                       21

<210> SEQ ID NO 871
```

```
<211> LENGTH: 21
<212> TYPE: DNA
<213> ORGANISM: Bos taurus

<400> SEQUENCE: 871
ttactctcgc taacaaaggc g                                          21

<210> SEQ ID NO 872
<211> LENGTH: 20
<212> TYPE: DNA
<213> ORGANISM: Bos taurus

<400> SEQUENCE: 872
aactcaagca gttttggtgc                                            20

<210> SEQ ID NO 873
<211> LENGTH: 24
<212> TYPE: DNA
<213> ORGANISM: Bos taurus

<400> SEQUENCE: 873
actacagttt cacctgcgac ttaa                                       24

<210> SEQ ID NO 874
<211> LENGTH: 19
<212> TYPE: DNA
<213> ORGANISM: Bos taurus

<400> SEQUENCE: 874
ttaagccggt cacagtccg                                             19

<210> SEQ ID NO 875
<211> LENGTH: 25
<212> TYPE: DNA
<213> ORGANISM: Bos taurus

<400> SEQUENCE: 875
gagataaaga gcgcctttgt tagcg                                      25

<210> SEQ ID NO 876
<211> LENGTH: 20
<212> TYPE: DNA
<213> ORGANISM: Bos taurus

<400> SEQUENCE: 876
ccaaccgtga gaagatgacc                                            20

<210> SEQ ID NO 877
<211> LENGTH: 23
<212> TYPE: DNA
<213> ORGANISM: Bos taurus

<400> SEQUENCE: 877
gaacctgcaa agttccaaag gag                                        23

<210> SEQ ID NO 878
<211> LENGTH: 23
<212> TYPE: DNA
<213> ORGANISM: Bos taurus

<400> SEQUENCE: 878
ccctttgcct caccctctc act                                         23
```

```
<210> SEQ ID NO 879
<211> LENGTH: 22
<212> TYPE: DNA
<213> ORGANISM: Bos taurus

<400> SEQUENCE: 879
gacgacatgg agaagatctg gc                                              22

<210> SEQ ID NO 880
<211> LENGTH: 23
<212> TYPE: DNA
<213> ORGANISM: Bos taurus

<400> SEQUENCE: 880
tcagctcaga gaagaaagtc cta                                             23

<210> SEQ ID NO 881
<211> LENGTH: 24
<212> TYPE: DNA
<213> ORGANISM: Bos taurus

<400> SEQUENCE: 881
ccctttgcct caccctttct cact                                            24

<210> SEQ ID NO 882
<211> LENGTH: 21
<212> TYPE: DNA
<213> ORGANISM: Bos taurus

<400> SEQUENCE: 882
ctttctacct gctgtcccac g                                               21

<210> SEQ ID NO 883
<211> LENGTH: 25
<212> TYPE: DNA
<213> ORGANISM: Bos taurus

<400> SEQUENCE: 883
tacgcagagg tttaataaca ttccc                                           25

<210> SEQ ID NO 884
<211> LENGTH: 23
<212> TYPE: DNA
<213> ORGANISM: Bos taurus

<400> SEQUENCE: 884
agctgccgag tgaaacacgt tac                                             23

<210> SEQ ID NO 885
<211> LENGTH: 20
<212> TYPE: DNA
<213> ORGANISM: Bos taurus

<400> SEQUENCE: 885
agattgtcag gtgagcgcag                                                 20

<210> SEQ ID NO 886
<211> LENGTH: 20
<212> TYPE: DNA
<213> ORGANISM: Bos taurus

<400> SEQUENCE: 886
ccataagtcc ctccacgatg                                                 20
```

```
<210> SEQ ID NO 887
<211> LENGTH: 22
<212> TYPE: DNA
<213> ORGANISM: Bos taurus

<400> SEQUENCE: 887
caatgcctcc tgcaccacca ac                                              22

<210> SEQ ID NO 888
<211> LENGTH: 19
<212> TYPE: DNA
<213> ORGANISM: Bos taurus

<400> SEQUENCE: 888
cagcatgaag atggccctg                                                  19

<210> SEQ ID NO 889
<211> LENGTH: 20
<212> TYPE: DNA
<213> ORGANISM: Bos taurus

<400> SEQUENCE: 889
ggatgtaggc actgggtgac                                                 20

<210> SEQ ID NO 890
<211> LENGTH: 23
<212> TYPE: DNA
<213> ORGANISM: Bos taurus

<400> SEQUENCE: 890
atcttgcacg gcagctcaat gaa                                             23

<210> SEQ ID NO 891
<211> LENGTH: 20
<212> TYPE: DNA
<213> ORGANISM: Bos taurus

<400> SEQUENCE: 891
gatcgttcag caatgcagcg                                                 20

<210> SEQ ID NO 892
<211> LENGTH: 23
<212> TYPE: DNA
<213> ORGANISM: Bos taurus

<400> SEQUENCE: 892
aagttcgagc caaagaccag gac                                             23

<210> SEQ ID NO 893
<211> LENGTH: 20
<212> TYPE: DNA
<213> ORGANISM: Bos taurus

<400> SEQUENCE: 893
caagaagtgt caccctcgcc                                                 20

<210> SEQ ID NO 894
<211> LENGTH: 25
<212> TYPE: DNA
<213> ORGANISM: Bos taurus

<400> SEQUENCE: 894
acatccttag agctggaact tggcc                                           25
```

```
<210> SEQ ID NO 895
<211> LENGTH: 20
<212> TYPE: DNA
<213> ORGANISM: Bos taurus

<400> SEQUENCE: 895
gtaggccctc agtacatgcc                                               20

<210> SEQ ID NO 896
<211> LENGTH: 21
<212> TYPE: DNA
<213> ORGANISM: Bos taurus

<400> SEQUENCE: 896
tttctctcct cagtgacatc g                                             21

<210> SEQ ID NO 897
<211> LENGTH: 23
<212> TYPE: DNA
<213> ORGANISM: Bos taurus

<400> SEQUENCE: 897
agggattgcc acgcagggtt taa                                           23

<210> SEQ ID NO 898
<211> LENGTH: 24
<212> TYPE: DNA
<213> ORGANISM: Bos taurus

<400> SEQUENCE: 898
ttaaacaagt accaaacacc acgc                                          24

<210> SEQ ID NO 899
<211> LENGTH: 22
<212> TYPE: DNA
<213> ORGANISM: Bos taurus

<400> SEQUENCE: 899
agcagccatt acgttgtctt cc                                            22

<210> SEQ ID NO 900
<211> LENGTH: 23
<212> TYPE: DNA
<213> ORGANISM: Bos taurus

<400> SEQUENCE: 900
ctaccctatt ctgaagggtt tca                                           23
```

METHODS AND SYSTEMS FOR ASSESSING AND/OR QUANTIFYING SPERM CELL SUBPOPULATIONS BEARING A SPECIFIC GENETIC SIGNATURE

CROSS-REFERENCE TO RELATED APPLICATION

This application claims benefit of and priority to U.S. Non-Provisional application Ser. No. 16/121,077 filed on Sep. 4, 2018. Ser. No. 16/121,077 claims priority to Provisional Application No. 62/553,771, filed Sep. 1, 2017. Each of these applications is incorporated by reference in its entirety herein.

INCORPORATION OF SEQUENCE LISTING

This application contains a sequence listing, submitted herewith electronically, containing the file named "P34577US01_SL.txt", which is 258,243 bytes in size which was created on Jan. 28, 2021, and which is herein incorporated by reference in its entirety.

BACKGROUND

High purity sperm cell populations that have been differentiated based on chromosomal differences—such as, for example, sperm cell populations that are skewed toward X-chromosome bearing or Y-chromosome bearing populations of spermatozoa, rather than the naturally-occurring 50:50 X:Y chromosome split—can be utilized to accomplish in vitro or in vivo fertilization, including artificial insemination (A) or in vitro fertilization (IVF) of ova or oocytes of numerous mammals such as bovids, equids, ovids, goats, swine, dogs, cats, camels, elephants, oxen, buffalo, or the like. See, e.g., U.S. Pat. No. 5,135,759.

Quantifying the relative population of sperm cells bearing the X or Y chromosome in a sexed semen sample has historically been limited to methods that are either low throughput and sensitive to user subjectivity (like fluorescent in situ hybridization), or relatively insensitive (like qPCR with a change detection threshold of 2×). Customers pay a premium for sexed semen, and should have access to reliable quality control data, which include an accurate, precise test for sex skew that is orthogonal to the method used to generate sexed semen.

However, conventional technologies are significantly limited in their ability to reliably assess the degree to which populations have been effectively skewed to X-chromosome bearing and Y-chromosome bearing populations. This can result in spermatozoa populations having unrecognized underrepresentation of the population of interest. Regardless of the separation method, there has not been a mechanism for directly and quantifiably assessing the sex-skewing of spermatozoa.

Sexed semen from sires with desired genetic traits provides farmers with the opportunity to advance herd genetics, and therefore farm profitability, while ensuring calves predominately of the desired sex are born as the herd turns over. Dairy farmers, for example, utilize X-skewed sexed semen (enriched for X chromosome sperm) to maintain a female, milk-producing herd (See Khalajzadeh et al., "Effect of widespread and limited use of sexed semen on genetic progress and reproductive performance of dairy cows," Animal, 6(9):1398-1406 (2012)). The ultimate utility of sexed semen is dependent upon the relative percentage of X or Y chromosome bearing sperm ('female or male cells') present in the product, and therefore dependent upon the accuracy of both making sexed semen and verifying the final sex skew.

Commercial sexed semen is currently produced by staining sperm with Hoechst 33342, a dye that penetrates live cells, binds stoichiometrically to DNA, and releases a fluorescent signal which quantitatively reflects total cellular DNA content when binding has been driven to completion (See, Lalande et al., "Quantitative studies on the precursors of cytotoxic lymphocytes. VI. Second signal requirements of specifically activated precursors isolated 12 h after stimulation," The Journal of Experimental Medicine, 151(1):12-19 (1980), Lalande et al., "Fluorescence flow analysis of lymphocyte activation using Hoechst 33342 dye," The Journal of Histochemistry and Cytochemistry, 27(1):394-397 (1979), Loken, "Separation of viable T and B lymphocytes using a cytochemical stain, Hoechst 33342," The Journal of Histochemistry and Cytochemistry, 28(1):36-39 (1980) and Loken, "Simultaneous Quantitation of Hoechst 33342 and Immunofluorescence on Viable Cells using a Fluorescence Activated Cell Sorter," Cytometry, 1(2):136-142. (1980)). Custom, high-throughput sexing cytometers discriminate the roughly 4% difference in total DNA content between X and Y chromosome containing sperm (due to the relative size of the sex chromosomes) (See, Moruzzi, "Selecting a mammalian species for the separation of X- and Y-chromosome-bearing spermatozoa," J Reprod Fertil, 57(2):319-323 (1979), van Munster et al., "Difference in volume of X- and Y-chromosome-bearing bovine sperm heads matches difference in DNA content," Cytometry, 35(2):125-128 (1979)) by quantifying Hoechst 33342 emission fluorescence (Johnson, "Sex preselection by flow cytometric separation of X and Y chromosome-bearing sperm based on DNA difference: a review," Reprod Fertil Dev, 7(4):893-903 (1995)). Once the sex of the sperm is determined, sperm are either segregated into separate containers based on sex (Johnson et al., "Sex preselection: high-speed flow cytometric sorting of X and Y sperm for maximum efficiency" Theriogenology, 52(8): 1323-1341 (1999)), or the undesired cell population is eliminated by laser-ablation (Faust et al., "1133 Effects for fertility of processing steps of a new technology platform for producing sexed sperm" Journal of Animal Science, 94(suppl_5):544-544 (2016)). The maximum achievable sex skew (enrichment for either the X or Y population) is at minimum dependent upon how well the cells are stained, alignment of the pancake shaped sperm head in the optical detection plane, and speed at which sperm flow through the cytometers (Johnson and Welch 1999).

Given the inherent challenges in separating two cell populations based on a 4% difference in total DNA content (Seidel, "Update on sexed semen technology in cattle," Animal, 8 Suppl 1:160-164 (2014)), the resulting product is variable in its final sex skew. Historical field performance has reported the percentage of female calves (vs. male calves) born after artificial insemination with sexed semen ranges from 86-93% (Cerchiaro et al., "A field study on fertility and purity of sex-sorted cattle sperm," J Dairy Sci, 90(5):2538-2542 (2007), Borchersen et al., "Danish A.I. field data with sexed semen," Theriogenology, 71(1):59-63 (2009), Norman et al., "Use of sexed semen and its effect on conception rate, calf sex, dystocia, and stillbirth of Holsteins in the United States," J Dairy Sci, 93(8):3880-3890 (2010), Healy et al., "Artificial insemination field data on the use of sexed and conventional semen in nulliparous Holstein heifers," J Dairy Sci, 96(3):1905-1914 (2013). The percentage of female calves born from the thousands of sexed semen inseminations most likely reflects variance in the actual skew of sexed semen straws.

An accurate, precise method for quantifying the sex skew of frozen-thawed semen is critical to define the current sexed semen products for farmers, and subsequently to improve the skew to meet market demands. To date, the available orthogonal methods for quantifying the sex skew of bovine semen have included fluorescence in situ hybridization (FISH) (Kawarasaki et al., "Verification of flow cytometorically-sorted X- and Y-bearing porcine spermatozoa and reanalysis of spermatozoa for DNA content using the fluorescence in situ hybridization (FISH) technique," *Theriogenology*, 50(4):625-635 (1998), Habermann et al., "Validation of sperm sexing in the cattle (*Bos taurus*) by dual colour fluorescence in situ hybridization," *J Anim Breed Genet*, 122 Suppl 1:22-27 (2005)), and quantitative PCR (qPCR) (Parati et al., "Sex ratio determination in bovine semen: a new approach by quantitative real time PCR" *Theriogenology*, 66(9):2202-2209 (2006), Puglisi et al., "In vitro fertilisation with frozen-thawed bovine sperm sexed by flow cytometry and validated for accuracy by real-time PCR" *Reproduction*, 132(3):519-526 (2006), Khamlor et al., "Determination of Sperm Sex Ratio in Bovine Semen Using Multiplex Real-time Polymerase Chain Reaction," *Asian-Australas J Anim Sci*, 27(10):1411-1416 (2014)). In addition, sex skew is commonly determined by re-quantifying the sex-skewed product using the same flow cytometers used to originally produce the sexed the semen (Seidel, "Update on sexed semen technology in cattle," Animal, 8 Suppl 1:160-164 (2014)). All of these approaches have drawbacks that limit their usefulness for robustly quantifying the sex-skew of sexed semen.

Available orthogonal assays (FISH and qPCR) specifically identify X and Y chromosomes, but lack quantitative sensitivity. FISH can be performed using X and/or Y-specific fluorescent probes which bind to target sequences on the desired chromosome. By definition, sex skew FISH assays which utilize only Y chromosomes probes (Kawarasaki et al., 1998, Habermann et al., 2005) perform as negative assays for X-skewed semen, such that the desired female cell is quantified based on a lack of signal. FISH assays which elegantly detect both sex chromosomes, however, have also been validated (Kawarasaki et al., 1998, Rens et al., "An X-Y paint set and sperm FISH protocol that can be used for validation of cattle sperm separation procedures," *Reproduction*, 121(4):541-546 (2001)). Data collection for FISH involves either capturing images from slides followed by manual or software assisted quantification, or manual binary scoring by a technician viewing the slides under the microscope. In either case, FISH provides absolute cell counts, but is low-throughput, with users typically scoring 100-500 cells per sample (Kawarasaki et al., 1998, Rens et al., 2001). These small sample sizes limit statistical rigor, and the assay is sensitive to user subjectivity.

Quantitative PCR (qPCR) also provides the opportunity to probe specifically for both the X and Y chromosomes (Parati et al., 2006, Puglisi et al., 2006, Khamlor et al., 2014), but may not provide the required accuracy and precision to guarantee farmers receive semen with the desired sex skew. qPCR is most useful for quantifying the relative abundance of target DNA compared to a control DNA (for example, X amplicon vs. autosome amplicon) based on number of PCR cycles required to surpass a fluorescence threshold. The fluorescence signal which reports each target DNA sequence to doubles with each PCR cycle, making this approach best suited for measuring large differences in relative DNA abundance (>2×). Relative qPCR quantification lacks the sensitivity to detect small differences in the skew of sexed semen. Absolute quantitation of DNA copy number can be attempted with qPCR, but requires a standard curve varying input template DNA to create a linear regression for each assay run Smith et al., "Advantages and limitations of quantitative PCR (Q-PCR)-based approaches in microbial ecology," *FEMS Microbiol Ecol*, 67(1):6-20 (2009). This 'absolute quantification' only represents a comparison to the standard curve rather than a known copy number when utilizing samples like genomic DNA (rather than synthetic DNA constructs), making it difficult to perform this assay in a high throughput and statistically rigorous manner.

Using semen sexing cytometers to quantify sex skew utilizes the exact same DNA binding dye and detection scheme that was originally used to identify X or Y chromosome-containing sperm during the sexing process, and is therefore subject to the same variations or biases that may have been present when producing the sex skewed product. Such pitfalls may include resolution limits imposed by flow speed, suboptimal cell orientation during fluorescence quantification, or DNA staining efficiency. This approach fails to confirm product quality with an independent, orthogonal test, and does not use unique, positive identifiers for either the X or Y chromosome.

Droplet digital PCR (ddPCR) has the capacity to provide an accurate and precise sex skew measurement by subdividing a pool of template DNA into nanoliter scale droplets containing either one or zero copies of template DNA. PCR amplification occurs in these droplets, and the number of copies of the amplicon of interest can be counted as the number of fluorescence-positive droplets based on classic qPCR fluorescent reporters. The present specification provides optimized and validated a multiplexed ddPCR assays that use this copy counting method to quantify the sex skew (ratio of X or Y chromosomes) in frozen-thawed bovine sexed semen. The present specification further provides for copy counting in sex selected semen prior to the freezing process. The specification further provides for methods to validate additional primers for use in ddPCR.

FIELD OF DISCLOSURE

Technologies for assessing, quantifying and isolating sperm cell populations and/or subpopulations having specific genetic signatures are provided, as well as methods and systems to assess the efficacy of semen sexing methods. Compositions for identification of X-chromosomes and Y-chromosomes in semen are also provided and for differentiating sperm containing X-chromosomes (e.g., female) and Y-chromosomes (e.g., male).

SUMMARY OF THE INVENTION

Among other things, the present disclosure provides technologies that can achieve reliable qualitative and/or quantitative assessment of sperm cells in sexed semen (e.g., differentiate the chromosomal content of the individual sperm cells in a semen sample). Such reliable assessment determines the usefulness and value of sex selected semen in non-naturally occurring populations of spermatozoa for applications-including but not limited to sex selection of offspring from mammals, various in vitro protocols for the fertilization of ova, various in vivo protocols such as artificial insemination, business methods involving the production of prize animals or meat animals, or preservation of rare or endangered animals. Accordingly, in some embodiments, the present disclosure provides higher quality sex selected semen non-naturally occurring populations of sperm cells.

In some embodiments, the present disclosure provides both systems and methods for the production of high-purity chromosomally differentiated sperm samples. Chromosomal differentiation can include differentiating X-chromosome bearing and Y-chromosome bearing sperm cells.

Particular embodiments of the invention are described, which may be used in numerous applications as set out elsewhere, that can be used to differentiate between or among sperm cells based on the chromosomal content of those sperm cells, or to assess such differentiation achieved through other means, such as flow cytometry.

In some embodiments, the present disclosure provides technologies to specifically determine within a sperm cell population the proportion of spermatozoa that are X-chromosome bearing and Y-chromosome bearing.

In some embodiments, the present disclosure provides artificial insemination samples that are sex-selected into X-chromosome bearing or Y-chromosome bearing spermatozoa.

In certain embodiments, the present disclosure provides in vitro insemination samples that are sex-selected into X-chromosome bearing or Y-chromosome bearing spermatozoa, for which the portion of X-chromosome bearing or Y-chromosome bearing spermatozoa has been reliably and directly quantified.

In some embodiments, the present disclosure provides technologies to preselect the sex of offspring of females inseminated with artificial insemination samples, or preselect the sex of offspring of ova fertilized with high purity artificial insemination samples, using sperm cell samples for which the portion of X-chromosome bearing or Y-chromosome bearing spermatozoa has been reliably and directly quantified at 80%, 85%, 90%, 95%, or greater than 95%.

In some embodiments, the present disclosure provides technologies to substantially eliminate or reduce uncertainty regarding the efficacy of chromosomal differentiation processes.

In some embodiments, the present disclosure provides systems and methods for quantitative assessment of both X-chromosome bearing and Y-chromosome bearing sperm cells in a population.

In some embodiments, the present disclosure provides technologies to validate or confirm the purity of the sperm samples provided by chromosomal differentiation methods.

In some embodiments, the present disclosure provides techniques for confirming or validating the differentiation of X-chromosome bearing sperm from Y-chromosome bearing sperm where there is a small difference in the amount of Y chromosome DNA to the amount of X chromosome DNA relative to the total amount of nuclear DNA.

In some embodiments, the present disclosure provides for a method of assessing sex-skew in a population of sperm cells, the method comprising steps of: detecting binding of a set of oligonucleotide agents to sperm DNA obtained from a sample of sperm cells, wherein the set includes: a first oligonucleotide agent that selectively binds to an X-chromosome nucleic acid sequence; a first oligonucleotide agent that selectively binds to a Y-chromosome nucleic acid sequence; and a third oligonucleotide agent that selectively binds to an autosomal chromosome nucleic acid sequence.

In some embodiments, the present disclosure provides for a method of producing a validated sex-skewed population of sperm cells comprising: obtaining a population of sperm cells; subjecting the population of sperm cells to sex selection; collecting the sex selected sperm cells; assessing the sex-skew of a sample of the sex selected sperm cell population against a sex skew benchmark value; and validating the sex-skewed population.

In some embodiments, the present disclosure provides for a kit for assessing the sex-skew in a population of sperm cells comprising: a first oligonucleotide agent that selectively binds to an X-chromosome nucleic acid sequence; a second oligonucleotide agent that selectively binds to a Y-chromosome nucleic acid sequence; and a third oligonucleotide agent that selectively binds to an autosomal chromosome nucleic acid sequence.

In some embodiments, the present disclosure provides for a method of fertilizing a mammalian ovum comprising: contacting a population of sperm cells to the ovum using artificial insemination (AI) or in vitro fertilization (IVF) with a validated population of sex skewed sperm cells.

In some embodiments, the present disclosure provides for a method of producing a sex skewed sperm cell population comprising: obtaining a population of sperm cells; photolysing the cells; treating the cells with a photoreactive DNA binding dye; suspending cells in a sperm separation and purification product; subjecting the population of sperm cells to sex selection; collecting the sex selected sperm cells; and assessing the sex skew of a sample of the sex selected sperm cell population.

Further embodiments of the invention are disclosed throughout other areas of the specification and claims.

BRIEF DESCRIPTION OF THE DRAWINGS

FIG. 9 shows that ddPCR according to an exemplary embodiment of the invention, is consistent with historical FISH in its ability to assess the efficacy of sex skewing. To have a 95% confidence that 95% of customers experience 85% skew, cutoff would be 85.8%, given an average assay error of 0.05%.

Figure 1:
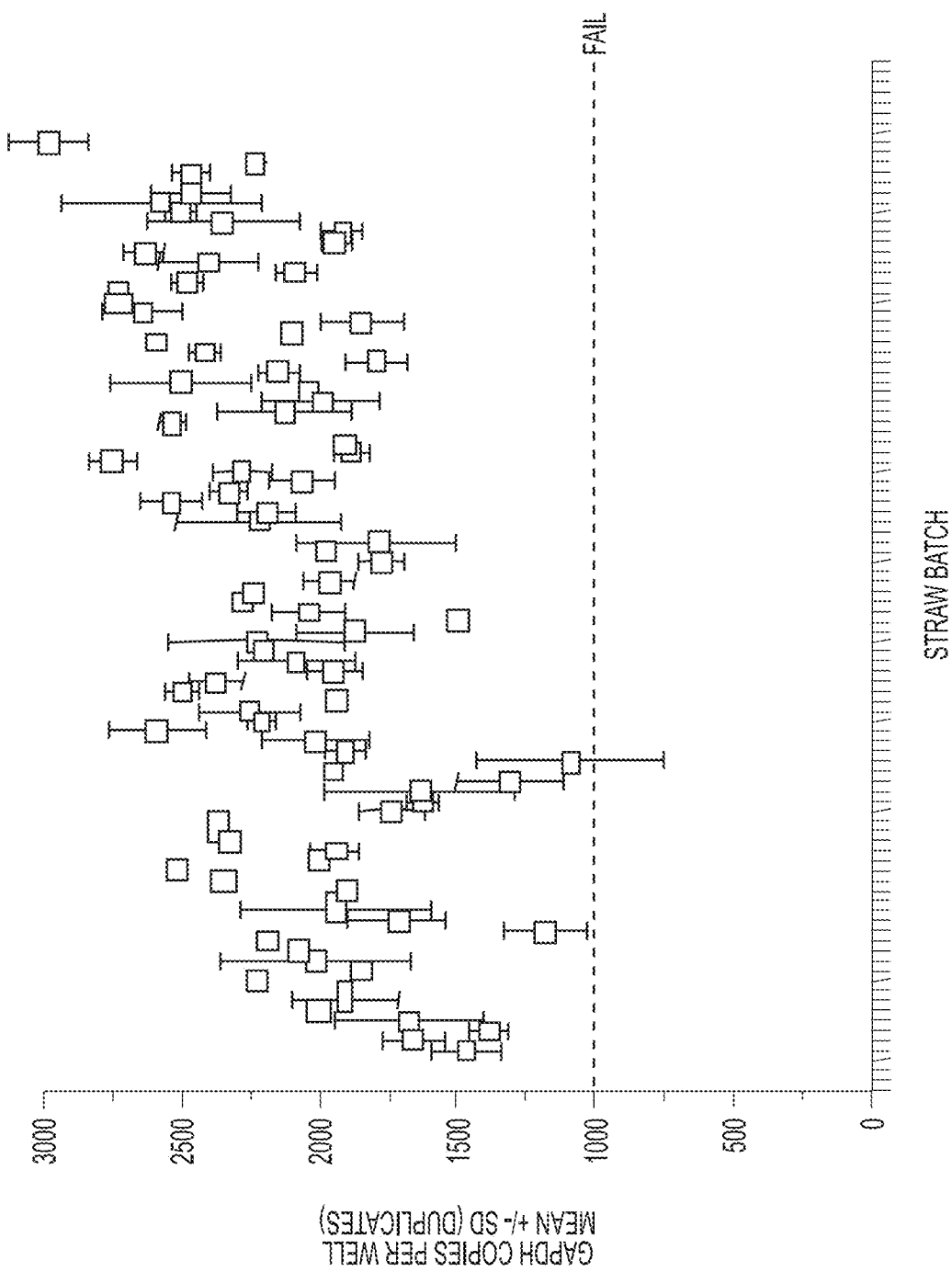
FIG. 1 shows detection of a housekeeping gene according to an exemplary embodiment of the invention using Droplet Digital PCR (ddPCR™). Detection of GAPDH demonstrated that for all samples tested (strawbatch, X-axis), at least 1000 copies of the gene are present per reaction well. The average total droplet count was 16,125±1481, with 12.5% occupancy (positive droplets).

The examples set out herein illustrate several embodiments of the present disclosure but should not be construed as limiting the scope of the present disclosure in any manner.

DETAILED DESCRIPTION

Differentiation Technologies

A number of techniques, directly or indirectly based on differences in size, mass, or density have been disclosed for use in discriminating X-chromosome-bearing from Y-chromosome-bearing spermatozoa. The most commonly used methods utilize flow cytometer techniques for the sex-skewing of spermatozoa and generally involve staining spermatozoa with a fluorochrome; the stained spermatozoa are made to flow in a narrow stream or band passing by an excitation or irradiation source such as a laser beam. As stained particles or cells pass through the excitation or irradiation source, the fluorochrome emits fluorescent light. An optical lens assembly collects the fluorescent light, focused on a detector—typically a photomultiplier tube—that generates and multiplies an electronic signal, which may then be analyzed by an analyzer. The data can then be displayed as multiple or single parameter chromatograms or histograms. The number of cells and fluorescence per cell may be used as coordinates. Detection of the two populations provides the opportunity to skew the population towards one population or the other, including by sorting X- and Y-chromosome bearing cells into separate populations, enriching the population for either X- or Y-chromosome bearing cells, or selectively removing, destroying, or otherwise inactivating either X- or Y-chromosome bearing cells in a population. However, with respect to this type of technology a variety of problems remain unresolved, and ensuring that chromosomal differentiation techniques yield highly purified populations (e.g. X-chromosome bearing or Y-chromosome bearing sperm cells) can be difficult.

The most common methods for assessing the efficacy of sperm cell differentiation are fluorescence in situ hybridization (FISH) and re-running the differentiation method for quality control (i.e. using the same flow-cytometric analysis that was used for the original differentiation to determine the efficacy of the original differentiation). These methods have significant limitations for providing meaningful assessment of differentiation. For example, FISH relies on manual assessment via microscopy, which is both time-consuming and labor intensive, rendering it ill-suited to rapid or large-scale implementation. In addition, FISH analysis typically involves specifically identifying Y-bearing spermatozoa by a DNA fragment hybridizing to a large pericentromeric repetitive DNA block on the bovine Y chromosome. FISH assay does not quantify the desired product, but assumes X-chromosome cell counts based on the absence of signal from a Y-chromosome probe. As a result, where a sperm cell population is skewed to X-chromosome bearing cells, this technique is insufficient.

With respect to the other common assessment method—validation via flow cytometric re-measurement of the DNA content of the sexed sperm—this method relies on the same instrument that produced the original sperm separation, it is therefore not truly independent. Further, these flow cytometry based assessment methods suffer from the same problems as the initial flow cytometric differentiation, resulting in inaccurate assessment. One problem can be the orientation of objects, particles, or cells in the sheath fluid stream. This can be particularly problematic when the object or cell is irregular in shape with respect to more than one axis, such spermatozoa for example. One aspect of this problem may be establishing the initial orientation of the object within the sheath fluid stream. A second aspect of this problem may be maintaining the orientation of the object with respect to the detector (photomultiplier tube or otherwise) during the period that emitted light from the object is measured. Another significant problem with conventional flow cytometer technologies can be the failure to encapsulate the objects or cells in a droplet of liquid, especially when droplets are formed around irregularly shaped objects and the droplet may not be of sufficient size to completely surround all the features of the objects or cells. Another significant problem with conventional flow cytometer technologies, as well as other technologies, can be a coincidence of measurable events, such that two events remain at least partially unresolved from one another, or the multiplicity of events may not be resolved at all and the objects corresponding to the multiplicity of events can be incorrectly assigned to a population or not assigned to a population at all, or both. Other significant problems include variability of signal depending on the orientation of irregularly shaped objects, such as spermatozoa, and lack of uniformity in exposure to the excitation source. There may be additional problems with assessment technologies that rely on stain bound to the nuclear DNA of sperm cells. First, because the DNA in the nucleus is highly condensed and flat in shape, stoichiometric staining of the DNA may be difficult or impossible. Second, stained nuclei may have a high index of refraction. Third, stain bound to the DNA to form a DNA-stain complex may reduce fertilization rates or the viability of the subsequent embryos. Fourth, the DNA-stain complex is typically irradiated with ultra-violet light to cause the stain to fluoresce. This irradiation may affect the viability of the spermatozoa. Due to these various problems, it may be preferable to use a method that requires less or no stain, or less or no ultraviolet radiation, or less or none of both. These problems highlight the need for techniques for independent assessment of sperm cell differentiation achieved using flow cytometry.

With respect to assessing the efficacy of differentiating X-chromosome bearing sperm cell or Y-chromosome bearing sperm cell populations, or more generally differentiating sperm cells based on chromosomal differences, the instant invention addresses every one of the above-mentioned problems in a practical fashion.

In the following description and examples, a number of terms are used. In order to provide a clear and consistent understanding of the description and claims, including the scope to be given such terms, definitions are provided for the terms as used in the description and claims. Unless otherwise defined herein, all technical and scientific terms used have the same meaning as commonly understood by one of ordinary skill in the art to which this invention belongs.

The invention involves the determination of the efficacy of techniques for differentiating sperm cells based on chromosomal differences. Such determination is essential for ensuring the quality of the sex-selected cells, and the success of subsequent use of those cells, for example in production of offspring having characteristics based on those chromosomal differences. In one aspect, sperm cells may be sex-selected based on the presence of an X-chromosome or a Y-chromosome, and the quality of that differentiation must be accurately assessed so as to permit reliable sex-selection of offspring. Sperm cells may also be differentiated based on other chromosomal differences, and confirmation of that differentiation must also be reliably made.

In one aspect, the present invention relates to chromosomal discrimination or differentiation of sperm cells. Because sperm cells are haploid, and contain only a single copy of each chromosome, individual sperm cells can be differentiated based on which copies of the chromosomes they possess. As used herein a "differentiation region" refers to a chromosome, or a specific portion or combination of portions thereof (e.g. an allele or haplotype) that permits differentiation of individual sperm cells in a population. For example, each sperm cell in a population obtained from a single male animal will contain one of two copies of a particular gene, which may be represented by two different alleles in the animal (i.e. the animal is heterozygous at that locus). Therefore, sperm cells in the population obtained from that animal can be differentiated based on which copy (or allele) they possess. Alternatively, sperm cells possess either a X chromosome or a Y chromosome, and can be differentiated based on which chromosome they possess. Chromosomal differentiation also includes selective identification or recognition of chromosomal DNA, including by binding to or otherwise recognizing a differentiation region. For example, this includes, but is not limited to, the binding of oligonucleotides to specific target chromosomal DNA sequences, such as antisense primers or guide RNAs. Discrimination of the sperm cells can be achieved using a variety of techniques, including but not limited to flow cytometry, magnetic techniques, columnar techniques, gravimetric techniques, use of electrical properties, combinations of electrical and gravimetric properties, use of motility properties, chemical techniques involving monoclonal antibodies and/or membrane proteins. Chromosomal differentiation may include sex skewing.

Sex skewing as used herein refers to altering a population of sperm cells to increase or decrease the proportion of X-chromosome or Y-chromosome bearing sperm cells. Methods for sex skewing include, but are not limited to, flow cytometric differentiation using the quantitative difference in the DNA content of X and Y chromosomes and consequently in the DNA content of X- and Y-bearing sperm. Other methods for differentiating using the quantitative difference in the DNA content of X and Y chromosomes and consequently in the DNA content of X- and Y-bearing sperm, without using dyes, are described in U.S. Pat. No. 9,683,922. U.S. Pat. No. 5,135,759 issued to Johnson involves individual discrimination and separation of the sperm through the techniques of flow cytometry; magnetic techniques, such as appears disclosed in U.S. Pat. No. 4,276,139, to columnar techniques as appears disclosed in U.S. Pat. No. 5,514,537, to gravimetric techniques as discussed in U.S. Pat. No. 3,894,529, U.S. Reissue Patent No. 32350, U.S. Pat. Nos. 4,092,229, 4,067,965, and 4,155,831. Use of electrical properties has also been attempted as shown in U.S. Pat. No. 4,083,957 as well as a combination of electrical and gravimetric properties as discussed in U.S. Pat. Nos. 4,225,405, 4,698,142, and 4,749,458. Use of motility properties has also been attempted as shown in U.S. Pat. Nos. 4,009,260 and 4,339,434. Chemical techniques have also been disclosed, such as those shown in U.S. Pat. Nos. 4,511,661 and 4,999,283 (involving monoclonal antibodies) and U.S. Pat. Nos. 5,021,244, 5,346,990, 5,439,362, and 5,660,997 (involving membrane proteins), and U.S. Pat. Nos. 3,687,803, 4,191,749, 4,448,767, and 4,680,258 (involving antibodies) as well as the addition of serum components as shown in U.S. Pat. No. 4,085,205. The production of chromosomally differentiated sperm cell populations, including sex-skewed (e.g. X-skewed) sperm cells can be achieved using a variety of approaches, including flow cytometric sorting or separation (e.g. by droplet sorting) or using focused energy, for example to inactivate certain differentiated sperm cells, as described in U.S. Pat. No. 9,588,100.

Differentiated sperm cell populations can be provided in a variety of forms. Differentiated sperm cell populations may be frozen or unfrozen, and may be in media that include one or more of water, salts (e.g. NaCl, KCl, $Na_2HPO_4$, $NaHCO_3$, $MgCl_2.6H_2O$), glucose, sodium pyruvate, sodium lactate, HEPES, bovine serum albumin (BSA), sodium hydroxide, tris, extenders (e.g. egg yolk), cryo-preservatives (e.g. glycerol), dyes, and antibiotics. Samples may also include compounds that inactivate or decrease cell motility, or increase viability. Inactivated or dead cells, or cell components or debris, may also be present in differentiated samples. In an exemplary embodiment, the sperm cell population comprises primarily X-chromosome bearing sperm in the presence of dead or inactivated sperm cells and cell debris, wherein the sperm cells are in a cryopreservative-containing media. In another exemplary embodiment, the sperm cell population comprises a separated sperm cell population that is primarily X-chromosome bearing sperm cells.

Providing sperm cell samples with an accurately assessed population enrichment, in accordance with the invention, can be achieved with the sperm cells obtained from numerous and varied species of mammals, including without limitation, mammals selected from the group consisting of a bovine species of mammal, an equine species of mammal, an ovine species of mammal, a canine species of mammal, a feline species of mammal, a swine species of mammal, a marine species of mammal, a deer species of mammal, a primate species of mammal, a goat species of mammal, or a species of mammal listed by Wilson, et. al., "Mammal Species of the World," Smithsonian Institution Press, (1993), hereby incorporated by reference herein.

The term "oligonucleotide agent", as used herein, refers to an agent that binds specifically with a target nucleic acid molecule or sequence or, alternatively, depending on the nature of the oligonucleotide agent, with its complement. Typically, an oligonucleotide agent comprises one or more oligonucleotides, although those skilled in the art will be familiar with various oligonucleotide variants (e.g., peptide nucleic acids, etc) that analogously bind to (e.g., hybridize with) nucleic acids. In some embodiments, an oligonucleotide agent is directed to a single target sequence; in some such embodiments, an oligonucleotide may contain a single oligonucleotide (or PNA, etc) molecule, that may be present in multiple copies. In such embodiments, each included oligonucleotide molecule has the same nucleotide sequence. Alternatively, in some embodiments, an oligonucleotide agent that targets a single sequence may contain a plurality of different oligonucleotide (or PNA, etc) molecules—i.e., oligonucleotides of different sequence, so that the oligonucleotide agent can be described as containing a "degenerate" oligonucleotide in that individual oligonucleotide molecules within the degenerate oligonucleotide agent each have a sequence directed to a different variant of the same target. Alternatively, as will be clear from context, in some embodiments, the term "oligonucleotide agent" may refer to a set of oligonucleotide (or PNA, etc) molecules that, when utilized together as described herein, perform a particular function or achieve a particular result. For example, in some embodiments, an oligonucleotide agent may comprise a first oligonucleotide and a second oligonucleotide whose sequences are directed to sites that are spaced apart and on complementary strands of a target nucleic acid molecule, so that together they are a primer set designed and constructed to amplify sequences between them. Analogously, in some embodiments, an oligonucleotide agent may comprise a set of oligonucleotides that includes one or more primer oligonucleotides and one or more probe oligonucleotides that together can be used as described herein in detection of a selected target sequence. In some embodiments one or more oligonucleotides within a set of oligonucleotides that together may be considered an oligonucleotide agent, may be a degenerate oligonucleotide. Those skilled in the art will appreciate that the term "oligonucleotide" typically refers to a polymer of nucleic acid residues (i.e., of DNA and/or RNA residues). In some embodiments, an oligonucleotide may incorporate one or more nucleic acid residue analogs, as is known in the art; in some such embodiments, an oligonucleotide may have one or more backbone modifications relative to DNA and/or RNA, and/or may have one or more sugar and/or one or more base modifications. For example, in some embodiments, an oligonucleotide may include one or more, or substantially all, phosphorothioate and/or phosphoroamidite linkages (rather than phosphodiester linkages). Alternatively or additionally, in some embodiments, an oligonucleotide may include one or more residues with a 2' modification relative to DNA and/or RNA. As is known in the art, natural nucleosides include, for example, adenosine, thymidine, guanosine, cytidine, uridine, deoxyadenosine, deoxythymidine, deoxy guanosine, and deoxycytidine;

exemplary nucleoside analogs include, for example, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof. As already noted, those skilled in the art are aware of other formats that can act as "oligonucleotides" as described herein such as, for example, peptide nucleic acid formats. Those skilled in the art will also be aware of various technologies for production of oligonucleotide agents and components thereof including for example, amplification and/or isolation from a source, chemical synthesis, recombinant production, etc.

In some embodiments, an oligonucleotide is partly or wholly single stranded; in some embodiments, an oligonucleotide is partly or wholly double stranded. In some embodiments an oligonucleotide has a nucleotide sequence comprising at least one element that encodes, or is the complement of a sequence that encodes, a polypeptide or portion thereof. In some embodiments, an oligonucleotide agent comprises one or more of a primer and/or probe.

The term primer refers to a single-stranded oligonucleotide capable of acting as a point of initiation of template-directed DNA synthesis under appropriate conditions (i.e., in the presence of four different nucleotide triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with the template. The term primer site, or priming site, refers to the area of the target DNA to which a primer hybridizes. The term primer pair means a set of primers including a 5' upstream primer that hybridizes with the 5' end of the DNA sequence to be amplified and a 3' downstream primer that hybridizes with the complement of the 3' end of the sequence to be amplified.

The term "probe"" or "hybridization probe" denotes a defined nucleic acid segment (or nucleotide analog segment) which can be used to identify by hybridizing to a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid. Probes can include one or more dyes. For example, a TaqMan® probe may include a reporter (fluorescent) dye and a quenching dye, such that when the probe is intact, the proximity of the quenching dye to the reporter dye suppresses the reporter fluorescence. These probes are useful for use with a PCR reaction using a polymerase that has exonuclease activity, such as AmpliTaq, which will cleave the probe if, during the PRC reaction, the region to which the probe is bound is amplified, thereby separating the reporter dye from the quenching dye, and resulting in a detectable fluorescence.

The present disclosure identifies combinations of primers or probes having a high binding specificity. It has become apparent that prior art probes—in particular X-chromosome probes—have a high level of cross reactivity to non-target chromosomal material and chromosomal RNA product that reduces their utility in many systems where the test samples include large amounts of non-target chromosomal nucleic acid. The present inventive probes and assay methods avoid these limitations of the prior art probes and assay methods. The combination of primers or probes is also highly suitable for use in other assay systems, including standard PCR, qPCR, real time PCR. Their lack of cross-reactivity would allow them to be employed in some cases for a reduced cost in existing assay systems due to their higher specificity. The relatively small size of the inventive probes would allow for cheaper production cost and a wider range of appropriate vectors and labels as compared to prior art probes.

The probes of the subject invention may be labeled in any of the conventional manners, such as with specific reporter molecules, (biotin, digoxygenin, etc.), fluorescent chemicals, radioactive materials, or enzymes such as peroxidases and phosphatases. Double labeling can also be employed. A preferred method particularly suited to the present invention is labeling by biotinylation during amplification or other production methods. Hybridization probes of the present invention may be made from DNA, RNA, or some combination of the two. The probes may include modified nucleotides. Modified internucleotide linkages are useful in probes comprising deoxyribonucleotides and ribonucleotides to alter, for example, hybridization strength and resistance to non-specific degradation and nucleases. The links between nucleotides in the probes may include bonds other than phosphodiester bonds, for example, peptide bonds. Modified internucleotide linkages are well known in the art and include methylphosphonates, phosphorotlioates, phosphorodithionates, phosphoroamidites and phosphate ester linkages. Dephospho-linkages are also known, as bridges, between nucleotides and include siloxane, carbonate, carboxymethyl ester, acetamidate, carbamate, and thioether bridges. "Plastic DNA," having for example N-vinyl, methacryloxyethyl, methacrylatiide or ethyleneimine internucleotide linkages can also be used in probes ((see e.g. Uhlmann and Peyman (1990)) "Peptide Nucleic Acid" (PNA), the entire contents and disclosure of which is hereby incorporated by reference) and is particularly useful because of its resistance to degradation by nucleases and because it forms a stronger hybrid with natural nucleic acids. (Orum et al. (1993); Egholm, et al. (1993), the entire contents and disclosure of which is hereby incorporated by reference).

Exemplary primers and probes of the present invention are including in the following list. The primers and probes are included in the Sequence Listing as SEQ ID NOS: 1-9, listed from top to bottom.

TABLE 1

Exemplary Chromosomal Differentiation Probes and Primers for assessment of sex skew

| Name (SEQ ID NO) | Target/description | Sequence |
| --- | --- | --- |
| GAPDH Forward #48 (SEQ ID NO: 1) | Forward (sense) primer; NTs 279-299 | AGATTGTCAGGTGAGCGCAG |

TABLE 1-continued

Exemplary Chromosomal Differentiation Probes and Primers for assessment of sex skew

| Name (SEQ ID NO) | Target/description | Sequence |
| --- | --- | --- |
| GAPDH Reverse #49 (SEQ ID NO: 2) | Reverse (antisense) primer; NTs 444-464 | CCATAAGTCCCTCCACGATG |
| GAPDH Probe (SEQ ID NO: 3) | Sense probe; NTs 381-403 | CAATGCCTCCTGCACCACCAAC |
| X-D1438319 Forward #22 (SEQ ID NO: 4) | Forward (sense) primer; NTs 18320-18345 | AGAGAAGACCCATGATGCAAAGTCC |
| X-D1438319 Reverse #23 (SEQ ID NO: 5) | Reverse (antisense) primer; NTs 18391-18414 | CCTTTCATAGCATCCATGCCTCC |
| X-D1438319 Probe (SEQ ID NO: 6) | Sense probe; NTs 18364-18390 | TCAACGATGGGAGCACTTTATGCTGT |
| Y-Y 1624 Forward #42 (SEQ ID NO: 7) | Forward (sense) primer; NTs 1583-1602 | TTAAGCCGGTCACAGTCCG |
| Y-Y 1624 Reverse #43 (SEQ ID NO: 8) | Reverse (antisense) primer; NTs 1769-1794 | GAGATAAAGAGCGCCTTTGTTAGCG |
| Y-Y 1624 Probe (SEQ ID NO: 9) | Sense probe; NTs 1670-1694 | CGAAATCCGTGTAGCCAATGTTAC |
| BT-ACTB-39344985 Plus #44 (SEQ ID NO: 10) | Forward (sense) primer | CCAACCgTgAgAAgATgACC |
| BT-ACTB-39345146 Minus #45 (SEQ ID NO: 11) | Reverse (antisense) prime | gAACCTgCAAAgTTCCAAAggAg |
| BT-ACTB-39344882 Plus #46 (SEQ ID NO: 12) | Forward (sense) primer | gACgACATggAgAAgATCTggC |
| BT-ACTB-39345121 Minus #47 (SEQ ID NO: 13) | Reverse (antisense) primer | TCAgCTCAgAgAAgAAAgTCCTA |
| #5 BT-gAPDH-279 Plus (SEQ ID NO: 14) | | AgATTgTCAggTgAgCgCAg |
| BT-gAPDH-463 Minus (SEQ ID NO: 15) | | CCATAAgTCCCTCCACgATg |
| BT-HMBS-30201851 Plus (SEQ ID NO: 16) | | CAgCATgAAgATggCCCTg |
| BT-HMBS-30202080 Minus (SEQ ID NO: 17) | | ggATgRAggCACTgggTgAC |
| BT-HMBS-30201033 Plus (SEQ ID NO: 18) | | TATgCTTgCCCACggAAgCC |
| BT-HMBS-30201259 Minus (SEQ ID NO: 19) | | gATCgTTCAgCAATgCAgCg |
| BT-B2M-104143141 Plus (SEQ ID NO: 20) | | CTTTCTACCTgCTgTCCCACg |
| BT-B2M-104143373 Minus (SEQ ID NO: 21) | | TACgCAgCggTTTAATAACATTCCC |
| BT-HPRT1-18150129 Plus (SEQ ID NO: 22) | | TTTgAACAgACTgATggTTCCC |
| BT-HPRT1-18150227 Minus (SEQ ID NO: 23) | | CAAgAAgTgTCACCCCTCgC |
| BT-PRLPO-64812825 Plus (SEQ ID NO: 24) | | gTAggCCCCTCAgTACATgC |
| BT-PRLPO-64813030 Minus (SEQ ID NO: 25) | | TTTCTCTCCTCAgTgACATCg |

TABLE 1-continued

Exemplary Chromosomal Differentiation Probes and Primers for assessment of sex skew

| Name (SEQ ID NO) | Target/description | Sequence |
| --- | --- | --- |
| BT-TBP-105690929 Plus (SEQ ID NO: 26) | | TTAAACAAgTACCAAACACCACgC |
| BT-TBP-105691127 Minus (SEQ ID NO: 27) | | AgCAgCCATTACgTTgTCTTCC |
| BT-X-1437318 Plus (SEQ ID NO: 28) | | TTACCTgAgAgAAgACCCATgATgC |
| BT-X-1438393 Minus (SEQ ID NO: 29) | | gAgCTTTgTACAgCCTTgggC |
| BT-X-1425187 Plus (SEQ ID NO: 30) | | gCACACTCACTAggAgAAACAAACC |
| BT-X-1425295 Minus (SEQ ID NO: 31) | | TggAACTgCTCCTCAAATCTgC |
| BT-X-1431878 Plus (SEQ ID NO: 32) | | gACTCAAgTCATTgAAgTCTgCTCC |
| BT-X1431983 Minus (SEQ ID NO: 33) | | CTCCTACAgCATAAAgTgCTCCC |
| BT-X-1438319 Plus (SEQ ID NO: 34) | | AgAgAAgACCCATgATgCAAAgTCC |
| BT-X-1438412 Minus (SEQ ID NO: 35) | | CCTTTCATAgCATCCATgCCTCC |
| BT-Y-786 Plus (SEQ ID NO: 36) | | AAgCCTgggCCACAATAAgg |
| BT-Y-922 Minus (SEQ ID NO: 37) | | AAgAgCgCCTTTgTTAgCg |
| BT-Y-1427 Plus (SEQ ID NO: 38) | | ATTAAgCCggTCACAgTCCg |
| BT-Y-1633 Minus (SEQ ID NO: 39) | | AAAgAgCgCCTTTgTTAgCg |
| BT-Y-1695 Plus (SEQ ID NO: 40) | | gAgCCTggACTTTCTTgTgC |
| BT-Y-1764 Minus (SEQ ID NO: 41) | | ATAAAgAgCgCCTTTgTTAgCg |
| BT-Y-1650 Plus (SEQ ID NO: 42) | | TTggCTACACggATTTCggC |
| BT-Y-1765 Minus (SEQ ID NO: 43) | | gATAAAgAgCgCCTTTgTTAgCg |
| BT-Y-1648 Plus (SEQ ID NO: 44) | | CATTggCTACACggATTTCgg |
| BT-Y-1767 Minus (SEQ ID NO: 45) | | gAgATAAAgAgCgCCTTTgTTAgCg |
| BT-Y-1804 Plus (SEQ ID NO: 46) | | TACTCTCgCTAACAAggCg |
| BT-Y-2012 Minus (SEQ ID NO: 47) | | TgAACTCAAgCAgTTTTggTgC |
| BT-Y-1717 Plus (SEQ ID NO: 48) | | TTggCTACACggATTTCggC |
| BT-Y-1827 Minus (SEQ ID NO: 49) | | AgAgCgCCTTTgTTAgCg |
| BT-Y-1802 Plus (SEQ ID NO: 50) | | CTTACTCTCgCTAACAAggCg |

TABLE 1-continued

Exemplary Chromosomal Differentiation Probes and
Primers for assessment of sex skew

| Name (SEQ ID NO) | Target/description | Sequence |
|---|---|---|
| BT-Y-2011 Minus (SEQ ID NO: 51) | | gAACTCAAgCAgTTTTggTgC |
| BT-Y-1803 Plus (SEQ ID NO: 52) | | TTACTCTCgCTAACAAAggCg |
| BT-Y-2010 Minus (SEQ ID NO: 53) | | AACTCAAgCAgTTTTggTgC |
| BT-Y-1624 Plus (SEQ ID NO: 54) | | TTAAgCCggTCACAgTCCg |
| BT-Y-1834 Minus (SEQ ID NO: 55) | | gAgATAAAgAgCgCCTTTgTTAgCg |

The present invention also contemplates the use of primers and probes specific for orthologous sequences in other species of mammals, including without limitation, mammals selected from the group consisting of a bovine species of mammal, an equine species of mammal, an ovine species of mammal, a canine species of mammal, a feline species of mammal, a swine species of mammal, a marine species of mammal, a deer species of mammal, a primate species of mammal, a goat species of mammal, or a species of mammal listed by Wilson, D. E. and Reeder, D. M., Mammal Species of the World, Smithsonian Institution Press, (1993), hereby incorporated by reference herein.

In some embodiments of the present invention, suitably stringent conditions should be of a highly stringent nature to ensure the elimination of false positives, such that (as with Affymetrix chips) a single nucleotide mismatch in the center of the probe will be sufficient to prevent hybridization. The precise hybridization conditions of the final reaction of biological samples with the oligonucleotides, present for example on oligo-chips, will, however, vary depending on the length of the oligonucleotides ultimately chosen as probes and their GC content as well as on the source of the test RNA population. Therefore, hybridization conditions can vary between 42° C. and 60° C. for approximately 16 hours. In certain embodiments, the present invention may use hybridization conditions that are <10° C. below the calculated melting temperature (Tm) of the perfect hybrid. Salt concentration and source also affect the hybridization conditions, i.e., whether sodium chloride or quaternary alkylammonium salts are employed. Stringency is also affected by post-hybridization washes and will vary based on rapidity of washing and on salt concentration and temperature employed (e.g., low stringency [1×SSC/0.1% SDS/45° C.] vs. moderate stringency [0.1×SSC/0.1% SDS/45° C.] vs. high stringency [0.1×SSC/0.1% SDS/60° C.]). The exact hybridization conditions may be adjusted according to one of ordinary skill in the art based on the disclosure of the present invention.

High purity separated spermatozoa from the various species of mammals can be incorporated into products that can be used with artificial insemination protocols or as part of commercial business methods such as those as described in U.S. Provisional Application Nos. 60/211,093, 60/224,050, or International Application No. PCT/US1999/017165; or be used with low dose insemination protocols as described in International Application No. PCT/US1998/027909, or used for in vitro fertilization of oocytes from animals, including humans, as described in U.S. Provisional Application No. 60/253,785 and U.S. patent application Ser. No. 15/476,509, each of the above-mentioned references are hereby incorporated by reference.

The use of the term "purity" or "high purity" should be understood to be the percent of the sperm cell population that are intact and viable, bearing a particular differentiating characteristic or desired combination of characteristics. Sperm cells that are dead, inactivated, or non-viable are not considered for purposes of purity herein. For example, where a population of spermatozoa are differentiated based upon bearing an X-chromosome as opposed to a Y-chromosome, a X-chromosome bearing population having 90% purity comprises a population of spermatozoa of which 90% of the individual intact, viable spermatozoa bear an X-chromosome while 10% of such population of spermatozoa may bear a Y-chromosome. As such, high purity with respect to X-chromosome bearing populations or Y-chromosome bearing populations can comprise a purity selected from the group consisting of between 90% to about 100%, between about 91% to about 100%, between about 92% to about 100%, between about 93% to about 100%, between about 94% to about 100%, between about 95% to about 100%, between about 96% to about 100%, between about 97% to about 100%, between about 98% to about 100%, between about 99% to about 100%.

Importantly, while numerous embodiments of the invention describe the assessment of high purity X-chromosome and Y-chromosome bearing populations of spermatozoa, the basic concepts of the invention should be understood to be applicable to the quantification or assessment made using other differentiation, such as differentiation based on the presence of particular alleles or haplotypes. It should be understood that the invention can be applicable to a variety of circumstances in which verification, assessment, and/or differentiation of the resolution of small differences in photo-generated signal may be necessary, such as product defect detection, field flow fractionation, liquid chromatography, electrophoresis, computer tomography, gamma cameras, time of flight instruments, or the like as would be readily understood by those skilled in those arts.

Assessment of Chromosomal Differentiation

In one aspect, the present invention provides systems and methods for accurate, quantitative assessment of chromosomal differentiation of sperm cells having either X- or Y-chromosomes (e.g., sex-skewed sperm cells or inseminate). Assessment of sex skew generally involves a determination of the overall representation of a particular chromosome, or a portion thereof, in a sperm cell population. For example, in a sperm cell population that has been sex-selected, assessment of sex skew will determine the representation of the X chromosome and the Y chromosome in the population as a whole, thereby quantifying the sex-skew. Sperm cell samples subjected to sex selection can be assessed using these systems and methods, providing information and data about the sperm cell population that is important for subsequent applications, including, for example, use of the sperm cells in fertilization. In a further aspect, the sperm cell population can be assessed for the presence or absence of one or more particular chromosomes, or a particular region or sequence of a chromosome, and the amount of each chromosome, or region or sequence thereof, can be quantified with respect to a housekeeping or reference gene.

Depending on the application, amplification may be useful in achieving desired goals in the detection of chromosomal differentiation region nucleic acid sequences. For example, the Y specific sequences of chromosomal DNA from a sperm cell population can be highly amplified using the inventive techniques and primers of the subject invention. This allows an increase in DNA for detection of differentiation regions, and thereby quantitative assessment of differentiation. Such amplification techniques may be minimized or excluded altogether when the Y chromosomal nucleic acid to be tested for is present in the sample at sufficiently high levels, or when samples can be enriched for the target nucleic acid.

PCR amplification techniques provide some advantages in producing large numbers of probes without the time and expenses required by some cloning or other production methods. However, one could always use these more conventional methods of nucleic acid replication for any of various reasons. In some cases, such as mass production in a fermentation type situation, conventional amplification techniques might be preferable to PCR methods.

According to one exemplary embodiment, primers as described herein allow specific amplification of the DNA target region in a test sample where the region is known to exist at a very low level prior to testing. It provides for one of several methods for producing large numbers of probe copies. Such primers can also serve as the basis for a test where a resultant high level of nucleic acid production indicates the presence of the target sequence.

In one aspect, the primers chosen are some distance from one another on the highly repeated region of the Y chromosome. The DNA product from such a pairing in a PCR amplification procedure would be useful in Y chromosome painting or decoration efforts. This type of product when bound to an appropriate label is useful in observing deletions or translocations. Long arm crossing over of the chromosome will be readily observed by these products because the sequences are in the distal arm region of the chromosome. A number of the DNA products produced in this manner can be used in concert to produce a more complete painted effect.

The present invention allows the identification of specific nucleic acid sequences corresponding to differentiation regions within chromosomal DNA from sperm cells. For example, probes can specifically bind to particular sequences of the Y chromosome, which permit differentiation from the X chromosome. Alternatively, or in combination therewith, the probes can bind specifically to sequences on the X chromosome, or bind to a reference or housekeeping chromosomal sequence. In one exemplary embodiment, the probes bind to sequences within differentiation regions bound by primer pairs, such that the target-binding sequence of the probe is included in the sequence amplified by the primers in a PCR reaction. These inventive probes display little or no nonspecific binding to autosomal and X chromosomes. The nonspecific binding of the probes of the present invention is generally less than $10^{-4}$. The nonspecific binding can range from $10^{-2}$ to $10^{-7}$, preferably $10^{-3}$ to $10^{-6}$, and most preferably $10^{-4}$ to $10^{-5}$. The level of nonspecific binding of a selected sequence is tolerated based on the requirements of the particular system for which the probes are being developed, and counterbalancing positive aspects of any particular probe sequence. Additional sequences for preparing probes having the reduced nonspecific binding are provided in the attached sequence listing and the present disclosure (SEQ ID NO:1 to 900).

According to some embodiments of the invention, different specific probes can be employed, alone or in combination. The size of these probes can be from 8-600 bp in length. Within this large range, 8-250 bp will be the usual range, 8-100 bp the average range, a preferable range will be 8-75 bp, and the most preferred range is 8-30 bp.

In another aspect, the disclosure provides for probes having a length of 10-20, 20-30, 30-40, 40-50, 50-60, 60-70, 70-80, 80-90, 90-100, 100-110, or 110-120 bp. In another aspect, the disclosure provides for probes having at least 10 bp, 20 bp, 30 bp, 40 bp, 50 bp, 60 bp, 70 bp, 80 bp, 90 bp, 100 bp, or 110 bp. In yet another aspect, the disclosure provides for probes having between 8-25 bp, 8-35 bp, 8-45 bp, and 8-55 bp. Additional sequences for preparing probes having reduced nonspecific binding are provided in the attached sequence listing and the present disclosure (SEQ ID NO:1 to 900).

The length of the candidate probe sequence can be chosen with a view towards the intended function of the final probe and its diagnostic environment. Alternatively, large probes can be chosen, and then the size narrowed. As the size is diminished, further testing is required to assure that the smaller conserved sequence still maintains sufficient hybridization capacity to fit a particular need.

Among other things, the present disclosure provides certain sets of oligonucleotide primers and/or probes from highly specific sequences, which permit quantitative assessment of the sex skew of sperm cell populations. Several of these DNA probes are shown in Table 1. Combinations and rearrangements of these probes and probe fragments either sequentially or in repeats can provide for effective probes. Promoter and restriction sites are also useful additions to the probes for cloning and other purposes, and do not diminish the usefulness of the resulting product. These multiple approaches of the inventive concept allow the production of probes specifically designed to be optimally suitable for particular production methods or applications of the end product.

Alternatively or additionally, in some embodiments, in order to facilitate the simultaneous use of three or more probe/primer sets for the detection of three or more specific sequences, the inventors have optimized the chemistry of the ddPCR implemented according to an exemplary embodiment of the invention. In one aspect, the optimization involves providing adequate dNTPs to drive the PCR reactions to completion.

The probes developed by the above method are useful for improving present assay methods. This can be done by substituting the small, highly specific inventive probes for the conventional probes employed in prior art methods. Additionally, the probe isolation and manufacture method of the present invention allows great flexibility in custom designing probes to meet particular requirements. In some cases, it may be advantageous to produce probes of a very large size, say well over the 400 bp probes suggested above.

The applications of the inventive probes can be augmented using PCR technology. PCR technology allows amplification of the DNA template without employing conventional cloning methods. Alternatively, PCR can be used as an adjunct to conventional DNA cloning methods. For instance, PCR can be used to amplify the DNA in sample fractions to be tested in order to increase the sensitivity of the test.

Identification of appropriate primer sequences can be important to facilitate achieving such advantageous amplification of sample DNA. Probes can be used in combination with primers which bind to particular nucleic acid sequences. Examples of such primers for amplification of particular target sequences of the Y chromosome, X chromosome, and the GAPDH gene are shown in Table 1 (SEQ ID NOS: 1-9). Exemplary combinations of primers and probes are demonstrated in the Examples below.

The basic requirement for oligonucleotide primers for use in the present invention is that they be homologous to an appropriate stretch of the base pair sequence flanking the desired probe sequence. They can include base pair sequences in common with the probe, and may also extend away from it in either direction as much as is useful to the needs of specificity and other considerations. The stretch of base pair sequence can include a chromosomal differentiation region, part or all of which may be in common with a probe.

In the examples provided below, primer sequences are chosen which flank the desired probe sequence. Typically, the primers are included within the desired probe sequence in order to avoid the requirement for separation and to maximize the production of the desired probe sequence. In particular, primer sequences are chosen to flank intron/exon junctions in order to specifically amplify genomic DNA, and not amplify any DNA sequences that have undergone splicing. The primers may be from 5 to 100 bp in length. In the case of very small sizes, annealing must be accomplished at low temperatures, often as low as 4° C. A preferable range of sizes for primers is 10-53 bp. The most preferred range is 15-30 bp primer length. In another aspect, the primer is 8-10 bp, 10-20 bp, or 20-30 bp. In yet another aspect, the primers are at least 8 bp, at least 10 bp, at least 15 bp, or at least 20 bp. Additional sequences for preparing primers having reduced nonspecific binding are provided in the attached sequence listing and the present disclosure (SEQ ID NO:1 to 900).

For primers according to some embodiments of the invention, it is best to select a sequence which will not bind to other areas of the chromosomal DNA. For example, primers for Y chromosome sequences should not bind to autosomal sequences or X chromosomal sequences. The same will be true for other exemplary sequences, such as X chromosome sequences, GAPDH sequences, or other housekeeping genes. When a primer does bind to non-selected sequences, a number of complicating phenomena occur. The resulting product is contaminated by undesirable sequences. These sequences tend to be much longer than the desired sequences because they are not flanked by a primer reading in the opposite direction on the homologous strand.

Non-target polymerization also causes a competitive use of the pool of substrate enzymes and other reactant material. This non-target polymerization compromises the efficient amplification of the desired sequence. Further, the resulting pool of nucleic acid fragments is likely to be highly contaminated with undesirable sequences.

In an aspect, the present disclosure provides for genomic DNA below 3 ng, below 2 ng, below 1 ng. In another aspect the genomic DNA is at least 1 ng, 2 ng, or 3 ng. In another aspect, the genomic DNA is between 9-27 ng, 9-12 ng, 12-15 ng, 15-20 ng, 20-24 ng, or 24-27 ng. In yet another aspect, the genomic DNA is 55 ng, 14 ng, or 15 ng. In another aspect, the forward and reverse primer are at a final concentration of 500, 900, or 1300 nM. In another aspect, the probe is added to reach a final concentration of 125, 150, 250, or 350 nM.

In another aspect, the sex skew methods provide for a replicate failure rate of less than 5% when provided at least 3 ng of genomic sample DNA. In an aspect, the sex skew methods provide for a replicate failure rate of less than 3% when provided at least 3 ng of genomic sample DNA. In an aspect, the sex skew methods provide for a replicate failure rate of less than 2.5% when provided at least 3 ng of genomic sample DNA. In another aspect, the sex skew methods provide for a replicate failure rate of at most 10% when provided at least 3 ng of genomic sample DNA. In another aspect, the sex skew methods provide for a replicate failure rate of at most 5% when provided at least 3 ng of genomic sample DNA. In another aspect, the sex skew methods provide for a replicate failure rate of at most 2.5% when provided at least 3 ng of genomic sample DNA.

In another aspect, the sex skew methods provide for a replicate failure rate of less than 5% when provided at least 9 ng of genomic sample DNA. In an aspect, the sex skew methods provide for a replicate failure rate of less than 3% when provided at least 9 ng of genomic sample DNA. In an aspect, the sex skew methods provide for a replicate failure rate of less than 2.5% when provided at least 9 ng of genomic sample DNA. In another aspect, the sex skew methods provide for a replicate failure rate of at most 10% when provided at least 9 ng of genomic sample DNA. In another aspect, the sex skew methods provide for a replicate failure rate of at most 5% when provided at least 9 ng of genomic sample DNA. In another aspect, the sex skew methods provide for a replicate failure rate of at most 2.5% when provided at least 9 ng of genomic sample DNA.

In another aspect, the sex skew methods provide for a replicate failure rate of less than 5% when provided between 9 and 27 ng of genomic sample DNA. In an aspect, the sex skew methods provide for a replicate failure rate of less than 3% when provided between 9 and 27 ng of genomic sample DNA. In an aspect, the sex skew methods provide for a replicate failure rate of less than 2.5% when provided between 9 and 27 ng of genomic sample DNA. In another aspect, the sex skew methods provide for a replicate failure rate of at most 10% when provided between 9 and 27 ng of genomic sample DNA. In another aspect, the sex skew methods provide for a replicate failure rate of at most 5% when provided between 9 and 27 ng of genomic sample DNA. In another aspect, the sex skew methods provide for a replicate failure rate of at most 2.5% when provided between 9 and 27 ng of genomic sample DNA.

In another aspect, the sex skew methods provide for a replicate failure rate of less than 5% when provided at least 1 ng of genomic sample DNA. In an aspect, the sex skew methods provide for a replicate failure rate of less than 3% when provided at least 1 ng of genomic sample DNA. In an aspect, the sex skew methods provide for a replicate failure rate of less than 2.5% when provided at least 1 ng of genomic sample DNA. In another aspect, the sex skew methods provide for a replicate failure rate of at most 10% when provided at least 1 ng of genomic sample DNA. In another aspect, the sex skew methods provide for a replicate failure rate of at most 5% when provided at least 1 ng of genomic sample DNA. In another aspect, the sex skew methods provide for a replicate failure rate of at most 2.5% when provided at least 1 ng of genomic sample DNA.

In another aspect, the sex skew methods provide for a replicate failure rate of less than 5% when provided less than 3 ng of genomic sample DNA. In an aspect, the sex skew methods provide for a replicate failure rate of less than 3% when provided less than 3 ng of genomic sample DNA. In an aspect, the sex skew methods provide for a replicate failure rate of less than 2.5% when provided less than 3 ng of genomic sample DNA. In another aspect, the sex skew methods provide for a replicate failure rate of at most 10% when provided less than 3 ng of genomic sample DNA. In another aspect, the sex skew methods provide for a replicate failure rate of at most 5% when provided at less than 3 ng of genomic sample DNA. In another aspect, the sex skew methods provide for a replicate failure rate of at most 2.5% when provided less than 3 ng of genomic sample DNA.

In another aspect, the sex skew methods provide for a replicate failure rate of less than 5% when provided less than 30 ng of genomic sample DNA. In an aspect, the sex skew methods provide for a replicate failure rate of less than 3% when provided less than 30 ng of genomic sample DNA. In an aspect, the sex skew methods provide for a replicate failure rate of less than 2.5% when provided less than 30 ng of genomic sample DNA. In another aspect, the sex skew methods provide for a replicate failure rate of at most 10% when provided less than 30 ng of genomic sample DNA. In another aspect, the sex skew methods provide for a replicate failure rate of at most 5% when provided at less than 30 ng of genomic sample DNA. In another aspect, the sex skew methods provide for a replicate failure rate of at most 2.5% when provided less than 30 ng of genomic sample DNA.

In another aspect, the present disclosure provides for primers at a final concentration of 900 nM primer, 125 nM probe for GAPDH (split into both FAM and HEX), 900 nM primer with 250 nM probe for the X chromosome (FAM only), and 1300 nM primer with 350 nM probe for the Y chromosome (HEX only). In yet another aspect, the present disclosure provides for primers at a final concentration of 900 nM primer, 125 nM probe for GAPDH, 900 nM primer with 250 nM probe for the X chromosome, and 1300 nM primer with 350 nM probe for the Y chromosome.

In another aspect, the present disclosure provides for primers at a final concentration of at least 100 nM primer, at least 50 nM probe for GAPDH (split into both FAM and HEX), at least 100 nM primer with at least 50 nM probe for the X chromosome (FAM only), and at least 100 nM primer with at least 50 nM probe for the Y chromosome (HEX only). In yet another aspect, the present disclosure provides for primers at a final concentration of between 50 and 1500 nM primer, between 20 and 500 nM probe for GAPDH, between 50 and 1500 nM primer with between 20 and 500 nM probe for the X chromosome, and between 50 and 1500 nM primer with between 20 and 500 nM probe for the Y chromosome.

In an aspect, the present disclosure provides for a kit for assessing the sex-skew in a population of cells, comprising: a first oligonucleotide agent that selectively binds to an X-chromosome nucleic acid sequence; a first oligonucleotide agent that selectively binds to an X-chromosome nucleic acid sequence; and a third oligonucleotide agent that selectively binds to an autosomal chromosome nucleic acid sequence. In another aspect, the first nucleotide agent comprises oligonucleotide primer sequences SEQ ID NOS: 4 and 5, and oligonucleotide probe sequence SEQ ID NO: 6. In another aspect, the second nucleotide agent comprises oligonucleotide primer sequences SEQ ID NOS:7 and 8, and oligonucleotide probe sequence SEQ ID NO: 9. In another aspect, the third nucleotide agent comprises oligonucleotide primer sequences SEQ ID NOS:1 and 2, and oligonucleotide probe sequence SEQ ID NO: 3. In a further aspect, the present disclosure provides for a kit comprising one or more oligonucleotide primer and probe sequences selected from the group consisting of SEQ ID NOS: 1-900, and fragments thereof. In yet another aspect, the present disclosure provides for a kit comprising two or more oligonucleotide primer and probe sequences selected from the group consisting of SEQ ID NOS: 1-900, and fragments thereof. In another aspect, the present disclosure provides for a kit comprising three or more oligonucleotide primer and probe sequences selected from the group consisting of SEQ ID NOS: 1-900, and fragments thereof. In a further aspect, the present disclosure provides for a kit comprising four or more oligonucleotide primer and probe sequences selected from the group consisting of SEQ ID NOS: 1-900, and fragments thereof. In another aspect, the present disclosure provides for a kit comprising five or more oligonucleotide primer and probe sequences selected from the group consisting of SEQ ID NOS: 1-900, and fragments thereof. Further, in an aspect, the present disclosure provides for a kit comprising six or more oligonucleotide primer and probe sequences selected from the group consisting of SEQ ID NOS: 1-900, and fragments thereof.

In an aspect of the present disclosure, a population of cells comprises an X-skewed sample sperm population. In an aspect, the sample population comprises 0 to 4000, 10 to 4000, 100 to 4000, 500 to 4000, 1000 to 4000, 2000 to 4000, 2500 to 4000, 3000 to 4000, and 3500 to 4000 cells. In another aspect, the sample population comprises at least 10, 100, 500, 100, 1500, 2000, 2500, 3000, 3500, 4000, or 4500 cells.

In an aspect, the present disclosure provides for a method of assessing sex-skew in a population of sperm cells, the method comprising steps of: detecting binding of a set of oligonucleotide agents to sperm DNA obtained from a sample of sperm cells, wherein the set includes: a first oligonucleotide agent that selectively binds to an X-chromosome nucleic acid sequence; a second oligonucleotide agent that selectively binds to a Y-chromosome nucleic acid sequence; and a third oligonucleotide agent that selectively binds to an autosomal chromosome nucleic acid sequence.

In another aspect, the first nucleotide agent comprises oligonucleotide primer sequences selected from the group consisting of SEQ ID NOS: 1-900, and oligonucleotide probe sequence selected from the group consisting of SEQ ID NOS: 1-900. In another aspect, the second nucleotide agent comprises oligonucleotide primer sequences selected from the group consisting of SEQ ID NOS:1-900, and oligonucleotide probe sequence selected from the group consisting of SEQ ID NOS: 1-900. In a further aspect, the third nucleotide agent comprises oligonucleotide primer sequences selected from the group consisting of SEQ ID NOS:1-900, and oligonucleotide probe sequence selecting from the group consisting of SEQ ID NO: 1-900.

In a further aspect, the present disclosure provides for a first oligonucleotide agent comprising a first oligonucleotide primer sequence selected from the group consisting of SEQ ID NOS: 1-900, a second oligonucleotide primer sequence selected from the group consisting of SEQ ID NOS: 1-900, and an oligonucleotide probe sequence selected from the group consisting of SEQ ID NOS: 1-900. In another aspect, the present disclosure provides for a second oligonucleotide agent comprising a first oligonucleotide primer sequence selected from the group consisting of SEQ ID NOS: 1-900, a second oligonucleotide primer sequence selected from the group consisting of SEQ ID NOS: 1-900, and an oligonucleotide probe sequence selected from the group consisting of SEQ ID NOS: 1-900. In yet another aspect, the present disclosure provides for a third nucleotide agent comprising a first oligonucleotide primer sequence selected from the group consisting of SEQ ID NOS: 1-900, a second oligonucleotide primer sequence selected from the group consisting of SEQ ID NOS: 1-900, and an oligonucleotide probe sequence selected from the group consisting of SEQ ID NOS: 1-900. In a further aspect, the first oligonucleotide agent, second oligonucleotide agent, and third oligonucleotide agents comprise different primers or probes.

In an aspect of the present disclosure, the sample of sex selected sperm cells comprise at least 10, 20, 30, 40, 50, 55, 60, 70, or 75% X chromosome bearing cells. In another aspect, sample of sex selected sperm cells comprise at least 10, 20, 30, 40, 50, 55, 60, 70, or 75% Y chromosome bearing cells. In another aspect of the present disclosure, the sample of sex selected sperm cells comprise between 10 and 20, 20 and 30, 30 and 40, 40 and 50, 50 and 55, 55 and 60, 60 and 70, 70 and 75, 75 and 85, or 85 and 100% X chromosome bearing cells. In another aspect of the present disclosure, the sample of sex selected sperm cells comprise between 10 and 20, 20 and 30, 30 and 40, 40 and 50, 50 and 55, 55 and 60, 60 and 70, 70 and 75, 75 and 85, or 85 and 100% Y chromosome bearing cells.

In an aspect, the present disclosure provides for a method of producing a validated sex skewed population of sperm cells comprising: obtaining a population of sperm cells; subjecting the population of sperm cells to sex selection; collecting the sex selected sperm cells; assessing the sex-skew of a sample of said sex selected sperm cell population against a sex skew benchmark value; and validating said sex-skewed population. In an aspect, the sex-skewed population is confirmed to bear an X-chromosome in at least 75%, at least 80%, at least 85%, at least 90%, or at least 95% of the sperm cells in the population. In another aspect, the sex-skewed population is confirmed to bear a Y-chromosome in at least 75%, at least 80%, at least 85%, at least 90%, or at least 95% of the sperm cells in the population. In another aspect, the sex-skewed population is confirmed to bear a Y-chromosome in between 60 and 75%, between 75 and 80%, between 80 and 85%, between 85 and 90%, between 90 and 95%, and between 95 and 95% of the sperm cells in the population. In yet another aspect, the sex-skewed population is confirmed to bear an X-chromosome in between 60 and 75%, between 75 and 80%, between 80 and 85%, between 85 and 90%, between 90 and 95%, and between 95 and 95% of the sperm cells in the population. In yet another aspect, the present disclosure provides technologies to preselect the sex of offspring of females inseminated with artificial insemination samples, or preselect the sex of offspring of ova fertilized with high purity artificial insemination samples, using sperm cell samples for which the portion of X-chromosome bearing or Y-chromosome bearing spermatozoa has been reliably and directly quantified at greater than 60%, greater than 80%, greater than 90%, greater than 95%, or greater than 98%. In another aspect, the present disclosure provides technologies to preselect the sex of offspring of females inseminated with artificial insemination samples, using sperm cell samples for which the portion of X-chromosome bearing or Y-chromosome bearing spermatozoa has been reliably and directly quantified at between 60% and 70%, between 70% and 75%, between 75% and 80%, between 80% and 85%, between 85% and 90%, between 90% and 95%, between 95% and 98%, between 80% and 95%, and between 98% and 100%. In another aspect, the present disclosure provides technologies to preselect the sex of offspring of ova fertilized with high purity artificial insemination samples, using sperm cell samples for which the portion of X-chromosome bearing or Y-chromosome bearing spermatozoa has been reliably and directly quantified at between 60% and 70%, between 70% and 75%, between 75% and 80%, between 80% and 85%, between 85% and 90%, between 90% and 95%, between 95% and 98%, between 80% and 95%, and between 98% and 100%.

In an aspect of the present disclosure, reliable quantification includes less than 10%, less than 5%, less than 4%, less than 3%, less than 2%, or less than 1% failure. In another aspect, reliable quantification includes at most 10%, at most 5%, at most 4%, at most 3%, at most 2%, or at most 1% failure.

The polymerase chain reaction process can be accomplished in a discontinuous stepwise fashion as has been demonstrated by a number of researchers in the field. Examples of this approach to PCR is shown in the Mullis patents (U.S. Pat. No. 4,683,195 issued Jul. 28, 1987, and U.S. Pat. No. 4,683,202 issued Jul. 28, 1987), which are hereby incorporated by reference. There are a number of well-known DNA polymerases which can be successfully employed in various PCR methods, such as those listed in the 1989 Sigma catalog (1989 Sigma Cytochemical Catalog, pp. 1028-1029). Other PCR methods and reagents may also be employed.

A PCR method better suited to large scale assay processing is an automated programmable system. One such system has been developed, as described in DNA, Vol. 7, No. 6, pp. 441-447, 1988. This article also describes the use of a thermostable DNA polymerase which is particularly suited to the production of the subject DNA probe and to the amplification of the test sample material. More advanced automated programmable systems especially suited for the present invention include the Droplet Digital PCR (ddPCR™) produced by BioRad. ddPCR is an adaptation of qPCR or realtime PCR in which a fluorescent probe reports amplification, but the reaction is divided into thousands of droplets. The ddPCR technique is described by Hindson et al., ("High-throughput droplet digital PCR system for absolute quantitation of DNA copy number.", Anal Chem 83(22): 8604-8610 (2011)). The template for ddPCR is optimally distributed so that each droplet contains one copy of the target template, and as a result the readout is counting the number of fluorescent-positive droplets. As with other PCR techniques, ddPCR requires a source of DNA, such as for example isolated genomic DNA. ddPCR is a PCR method that is based on water-oil emulsion droplet technology, wherein each sample is fractionated into around 20,000 or more droplets, and PCR amplification of the template DNA occurs in each individual droplet. ddPCR technology uses reagents and workflows similar to those used for most standard TaqMan probe-based assays. The massive sample partitioning is a key aspect of the ddPCR technique, allowing for simultaneous multiplication of amplification (and detection), up to 1000-fold over other PCR techniques. The PCR reaction can be carried out with one or more primer pairs, to amplify one or more corresponding regions in the template DNA. The PCR reaction can be carried out in the presence of one or more probes, which are specific for and allow for specific detection of the one or more amplified regions. Following PCR, each droplet is analyzed or read in a flow cytometer to determine the fraction of droplets in which the target DNA was amplified, typically by detecting fluorescence emitted by the specific probes.

The sex skew assay is designed to interrogate one target each on the X and Y chromosomes as well as an autosomal target to confirm total cells counted. Optimizing a triplex ddPCR assay requires maximizing separation of the droplet populations containing only individual target amplicons (X, Y, or GAPDH), as well as the dual and triple occupancy droplets (X+Y, X+GAPDH, Y+GAPDH, and X+Y+GAPDH), which can be challenging when utilizing a 2-channel detection platform. Two amplicons can be discretely identified, one in each of the two fluorescent channels utilizing HEX and FAM probes for the two targets, respectively. The third amplicon is detected using a mix of two probes which are sequence identical, but differentially tagged with either HEX or FAM fluorophores (see FIG. 3 schematic). A robust sex skew assay intended as a quality control metric also requires assaying as many cells as necessary from a single semen straw without compromising the ability to separate the target populations. To achieve the necessary quality control target for validation, input quantities for template genomic DNA and each primer and probe are iteratively adjusted until maximal separation of the fluorescent droplet populations is achieved, while assaying the maximal total number of cells. The results are shown in Example 4 below.

A 1:1 autosomal:(X+Y) copy ratio is observed in conventional semen samples obtained from genomic DNA isolated from the viable sperm population in frozen-thawed sex skewed semen straws. However, given the unique nature of IntelliGen X skew sexed semen, which contains laser-sliced cells predominantly comprising Y chromosome sperm, attention is needed to clean up the samples prior to genomic DNA extraction. If DNA is extracted from the frozen-thawed sexed semen sample without removing the laser-killed cells, the expected result is an apparent 50/50 X/Y chromosome representation. This does not, however, reflect the viable, motile population which provides the cells that will ultimately produce a pregnancy. The present specification provides for removing non-viable sperm from the sample prior to genomic DNA extraction. In an aspect, the non-viable sperm are removed using BoviPure™ gradient centrifugation followed by glass wool column purification.

Prior to amplification, restriction enzymes are often employed to cut the nucleic acid into smaller pieces and to digest non-target sequences. The restriction enzymes used must be chosen to assure that they will not cause breaks within the target or primer sequences but will none the less effectively digest undesirable sequences. The preferred restriction enzymes for some uses are set out in the example section below. Virtually any restrictive enzyme can be used depending on the particular requirement involved. These can include those listed in the Sigma catalog, among others (1989 Sigma Biochemical catalog, pp. 1008-1027).

PCR primers produced by the method of the present invention have a number of uses outside gender assay probe development. When paired with a sister primer some substantial length downstream, a very long nucleic acid strand is produced. While such strands are likely not suitable for gender determination, they have numerous other uses. By way of example, when appropriately labeled these sequences can serve as Y chromosome painting or decorating material. This provides a tagging method by which to observe translocations and deletions in the distal arm regions of the Y chromosome.

An objective of the present invention is assessing or validating chromosomal differentiation, that is, to determine whether the chromosomes present in a differentiated sample in fact comprise those that have been selected for. Many references describe genotyping methods that can be useful, such as Chen et al., "Single nucleotide polymorphism genotyping: biochemistry, protocol, cost and throughput," *Pharmacogenomics J.*, 3(2):77-96 (2003); Kwok et al., "Detection of single nucleotide polymorphisms," *Curr Issues Mol. Biol.*, 5(2):43-60 (2003); Shi, "Technologies for individual genotyping: detection of genetic polymorphisms in drug targets and disease genes," *Am J. Pharmacogenomics*, 2(3): 197-205 (2002); and Kwok, "Methods for genotyping single nucleotide polymorphisms," *Annu Rev Genomics Hum Genet.*, 2:235-58 (2001). Common genotyping methods include, but are not limited to, TaqMan assays and modifications thereof such as Molecular Beacon assays, SNPlex platforms, Bio-Plex system, CEQ and SNPstream systems, Molecular Inversion Probe array technology, BeadArray Technologies (e.g., Illumina GoldenGate and Infinium assays), single stranded conformation polymorphism assays (SSCP), molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

The sequence of a differentiation region can be used to design detection reagents such as oligonucleotide probes, which may optionally be implemented in a kit format. Preferably, the oligonucleotide probe will have a detectable label. Experimental conditions can be chosen such that if the sample DNA contains the differentiation region, a hybridization signal can be detected because the probe hybridizes to the corresponding complementary DNA strand in the sample, while if the sample DNA does not contain a chromosome including the differentiation region, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, such as a chromosomal differentiation region. The use of the polymerase chain reaction is described in Saiki et al., *Science*, 230:1350-1354 (1985). Amplification may be used to determine whether a particular chromosome is present, by using a primer that is specific for a differentiation region of that chromosome. Alternatively, various methods are known in the art that utilize oligonucleotide ligation as a means of detecting specific chromosomes, for examples see Riley et al., *Nucleic Acids Res.*, 18:2887-2890 (1990); and Delahunty et al., *Am. J. Hum. Genet.*, 58:1239-1246 (1996). The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in International Publication No. WO 95/11995. The arrays would contain a battery of allele-specific oligonucleotides representing each of the polymorphic sites. One or both polymorphic forms may be present in the array, for example the polymorphism of a SNP position may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay, *Nat. Biotech.*, 16:4044 (1998); Hacia et al., *Nature Genetics*, 14:441-447 (1996); Lockhart et al., *Nature Biotechnol.*, 14:1675-1680 (1996); and De Risi et al., *Nature Genetics*, 14:457-460 (1996).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE),6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product. In some embodiments, a composition contains two or more differently labeled oligonucleotides for simultaneously probing the identity of nucleotides or nucleotide pairs at two or more differentiation regions. It is also contemplated that primer compositions may contain two or more sets of specific primer pairs to allow simultaneous targeting and amplification of two or more regions. In one embodiment, the present invention provides methods for assessment of chromosomal differentiation of a sperm cell population, comprising obtaining a population of sperm cells, isolating the DNA from said population of sperm cells, and exposing said DNA to at least one oligonucleotide that selectively identifies a chromosomal differentiation region. In a further embodiment, the sperm cells are bovine sperm cells.

In a further aspect, the sperm cell population can be chromosomally differentiated in a variety of ways. For example, the sperm cells may be differentiated based on the presence of one or more alleles or haplotypes. Alternatively, or in combination, the sperm cells may be differentiated based on the presence of an X-chromosome or a Y-chromosome (i.e. sex-skewed). The chromosomal differentiation can be carried out in a variety of ways, including flow cytometry, magnetic techniques, columnar techniques, gravimetric techniques, use of electrical properties, combinations of electrical and gravimetric properties, use of motility properties, chemical techniques involving monoclonal antibodies and/or membrane proteins. In one embodiment chromosomal differentiation of the sperm cells comprises sex skewing using the quantitative difference in the DNA content of X and Y chromosomes and consequently in the DNA content of X- and Y-bearing sperm, including, but not limited to, by staining with a DNA-intercalating dye or using focused energy. In another aspect, the sperm cell populations can be sorted or separated populations, wherein one or more populations have been selected and removed, or the population may include sperm cell, or portions thereof, that have been selectively inactivated, killed, or ablated.

In another aspect, the invention involves isolation of DNA from a chromosomally differentiated sperm cell population. DNA can be isolated using a variety of techniques, using a combination of physical and chemical methods. Generally, DNA isolation includes cell lysis to expose the cytoplasm and nucleus of the cells, along with the DNA contained in the nucleus. Lysis can be achieved through chemical disruption of the membrane (e.g. using detergents and/or surfactants) and or physical disruption of the membrane (e.g. using sonication, osmotic shock, or freeze-thaw). Lysis is generally performed in the presence of both proteases to break down proteins and enzymes, and RNase to degrade RNA. The lysate is then treated to isolate the DNA, typically by ethanol precipitation, phenol-chloroform extraction, or adsorption to a column or filter.

The present invention further provides one or more specific nucleic acid molecules or aptamers, preferably an oligonucleotide, more preferably a DNA molecule, that binds preferentially to either a sperm cell containing a X-chromosome (hereinafter referred to as a "X sperm cell") or a sperm cell containing a Y-chromosome (hereinafter referred to as a "Y sperm cell"), and preferably preferentially binds better to one of the X sperm cells or binds with significantly different affinities to each type of X and Y sperm cells.

In a further aspect, the invention includes at least one pair of primers. In a further aspect, the invention includes at least one pair of primers and an oligonucleotide probe that is specific for a region. In a further aspect, a first pair of primers and probe are specific for an X chromosome, a second pair of primers and probe are specific for a Y chromosome, and a third pair of primers and probe are specific for a reference sequence, which is equally represented in the sperm cell population regardless of chromosomal differentiation (e.g. GAPDH). An exemplary embodiment of the invention includes amplification of at least a portion of a first differentiation region, comprising nucleotide 18320 to 18414 of a bovine X chromosome. Another exemplary embodiment of the invention includes detection of at least a portion of a first differentiation region, comprising nucleotide 18320 to 18414 of a bovine X chromosome. The X-chromosome primers may comprise SEQ ID NOS: 4 and 5, and the detection probe may comprise SEQ ID NO:6. In a further aspect, an exemplary embodiment of the invention includes amplification of at least a portion of a second differentiation region, comprising nucleotides 1583 to 1794 of a bovine Y chromosome. Another exemplary embodiment of the invention includes detection of at least a portion of a second differentiation region, comprising nucleotides 1583 to 1794 of a bovine Y chromosome. The Y chromosome primers may comprise SEQ ID: NOS: 7 and 8, and the detection probe may comprise SEQ ID NO: 9. In a further embodiment the invention includes amplification and/or detection of a reference of housekeeping chromosomal nucleotide sequence, such as GAPDH. The GAPDH primers may comprise SEQ ID NOS: 1 and 2, and the detection probe may comprise SEQ ID NO: 3. In a preferred embodiment the X-chromosome primers and probe are used in combination with the GAPDH primers and probe, the Y-chromosome primers and probe are used in combination with the GAPDH primers and probe, or both the X-chromosome and Y-chromosome primers and probe are used in combination with the GAPDH primers and probe, in order to specifically quantify the proportion of sperm cells in the population that are X-chromosome or Y-chromosome bearing sperm cells.

In another aspect, the present invention provides for detection of a reference housekeeping chromosomal nucleotide sequence selected from the group consisting of GAPDH, TATA-box binding protein (TBP), β-actin (ACTB), and prolactin-like protein O (PRLPO).

In another aspect, the invention involves the amplification and/or detection of chromosomal nucleotide sequence orthologous to 18320 to 18414 of a bovine X chromosome, nucleotides 1583 to 1794 of a bovine Y chromosome. Such orthologous sequences can include, for example, the corresponding chromosomal nucleotide sequences of X and Y chromosomes of an equine species of mammal, an ovine species of mammal, a canine species of mammal, a feline species of mammal, a porcine species of mammal, a marine species of mammal, a deer species of mammal, a primate species of mammal, or a goat species of mammal. In another aspect, the disclosure provides for the detection of chromosomal nucleotide sequence orthologous to 18320 to 18414 of a bovine X chromosome, nucleotides 1583 to 1794 of a bovine Y chromosome. Such orthologous sequences can include, for example, the corresponding chromosomal nucleotide sequences of X and Y chromosomes of an equine species of mammal, an ovine species of mammal, a canine species of mammal, a feline species of mammal, a porcine species of mammal, a marine species of mammal, a deer species of mammal, a primate species of mammal, or a goat species of mammal.

In a preferred embodiment, the present invention involves amplification and detection of differentiation regions in DNA from a chromosomally differentiated sperm cell population using ddPCR. In a further aspect, analysis of the amplification and detection using ddPCR is carried out using an algorithm that distinguishes or gates droplets based on the presence of any one of the target differentiation regions. The gating strategy can discriminate two or more, three or more, four or more, five or more, six or more, seven or more, eight or more, nine or more, ten or more, etc. groups of droplets based on the presence of copies of the target differentiation region. In an exemplary embodiment, the gating strategy differentiates droplets based on seven different potential occupancy combinations. Analysis of the ddPCR results can also be carried out using an analysis algorithm that accounts for multiple occupancy of droplets by individual probes, for example by Poisson correction. Analysis of the ddPCR results can also be carried out using an analysis algorithm that identifies samples wherein one or more of the following conditions applies: (1) Where duplicate wells provided a percentage of the population having at least one differentiation region with variance greater than 0.8% (=1.635 SD replicate variance to provide 95% confidence) and the duplicates fall on either side of the 85% mark; (2) where the counts for either a differentiation region, including a housekeeping or reference region, fall below 1000 copies/well; (3) where mean fluorescence is below detection range; and (4) where the total of any two mutually exclusive differentiation regions is different from a housekeeping region total copies by more than 2 standard deviations.

Systems for Assessing Chromosomal Differentiation

Another aspect of the present invention provides systems that permit accurate, quantitative assessment of chromosomal differentiation. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated systems comprise, DNA from a chromosomally differentiated sperm cell population, and at least one set of primers and probes designed for specific determination of the overall representation of a particular chromosome, or a portion thereof, in the DNA from a chromosomally differentiated sperm cell population. The systems and kits may further comprise any addition component necessary, sufficient, or useful for practicing any of the methods described herein, including, but not limited to, polymerase enzymes, dNTPs, oils, thermocylers, droplet generators, droplet readers, and cytometers.

Use of Differentiated Sperm Cells for Fertilization

Another aspect of the present invention is the fertilization of an egg or insemination of a female mammal, generally employing the novel process for sorting spermatozoa as described above. Once a chromosomally differentiated sperm cell population has been assessed as discussed in greater detail above, the sperm cell population may be used to inseminate a female mammal. Insemination may be performed according to any of a number of methods well known to those of skill in the art. These methods include, for example, artificial insemination, including standard artificial insemination and deep uterine insemination, and other methods well known to those of skill in the art. For example, a chromosomally differentiated sperm cell population of a known, assessed quality may be used to inseminate a female mammal, such as for example, by artificial insemination. In a particular embodiment, the sperm cell population may be in an elongated container for use in the insemination of a female mammal. Alternatively, the sperm dispersion may be used to fertilize an egg, and more particularly, an egg in vitro, such as for example, by microinjection, including intracytoplasmic sperm injection (ICSI), and other methods well known to those in the art. The fertilized egg may thereafter be introduced into the uterus of a female mammal by any of a number of means well known to those of skill in the art, such as for example embryo transplant.

Fertilization by insemination of a female mammal or fertilization of an egg in vitro (followed by introduction of the fertilized egg into the uterus of a female) using a chromosomally differentiated sperm cell population may occur shortly after formation of the sperm cell population, such as for example, within about 120 hours, preferably within about 96 hours, more preferably within about 72 hours, still more preferably within about 48 hours, and in a particular embodiment, within about 24 hours after formation of the sperm dispersion. Prior to use in fertilization, in order to ensure the fertilization will yield the desired results, the quality and/or efficacy of the differentiation should be assessed, as described herein. For example, a sperm cell population that will be used for fertilization can be confirmed, according to the invention, to be comprised of at least 75%, at least 80%, at least 85%, at least 90%, or at least 95% chromosomally differentiated cells. As a further example, in a sperm cell population sorted on the basis of bearing an X-chromosome to be used for production of female offspring, at least 75%, at least 80%, at least 85%, at least 90%, or at least 95% of the sperm cells in the population are confirmed to bear an X-chromosome, (and not bear a Y-chromosome), controlling for a housekeeping gene, using the methods and systems described herein.

In such instances, generally the differentiated sperm cell populations may not have been cryopreserved prior to fertilization; instead it may have been maintained in a motility inhibitor and/or may have been refrigerated at temperatures of about 4° C. to about 25° C., more preferably from about 10° C. to about 25° C., still more preferably from about 15° C. to about 20° C., and most preferably at about 18° C. Alternatively, the population may be cryopreserved and then thawed prior to fertilization (i.e., the dispersion is frozen/thawed or comprises frozen/thawed sperm cells). Typically, in such an instance, the cryopreserved population will be thawed immediately, such as, for example, within about 15 minutes, before fertilization. Alternatively, the cryopreserved population may be thawed over a period of time or thawed and subsequently stored for a period of time, such as for example less than about 5 days, more preferably less than about 2 days, still more preferably less than about 1 day, and most preferably, less than about 12 hours.

The specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function is accomplished by a device, subroutine, or program. Apparatus claims may not only be included for the devices described, but also method or process claims may be included to address the functions the invention and each element performs. Neither the description nor the terminology is intended to limit the scope of the claims which now be included.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms-even if only the function or result is the same. Such equivalent, broader, or even more generic terms should be considered to be encompassed in the description of each element or action. Such terms can be substituted where desired to make explicit the coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "droplet generator" should be understood to encompass disclosure of the act of "generating droplets" whether explicitly discussed or not and, conversely, are the only disclosure of the act of "generating droplets", such a disclosure should be understood to encompass disclosure of a "droplet generator" and even a means for "generating droplets". Such changes and alternative terms are to be understood to be explicitly included in the description.

Additionally, the various combinations and permutations of all elements or applications can be created and presented. All can be done to optimize the design or performance in a specific application.

Any acts of law, statutes, regulations, or rules mentioned in this application for patent: or patents, publications, or other references mentioned in this application for patent are hereby incorporated by reference.

In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted broadly and in their most expansive form.

Thus, the applicant(s) should be understood to have support to claim at least: i) each of the liquid to gas conversion devices described herein, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and the x) the various combinations and permutations of each of the elements disclosed.

In an aspect, the present disclosure provides for the following embodiments:

Embodiment 1. A method of assessing sex-skew in a population of sperm cells, the method comprising steps of: detecting binding of a set of oligonucleotide agents to sperm DNA obtained from a sample of sperm cells, wherein the set includes: a first oligonucleotide agent that selectively binds to an X-chromosome nucleic acid sequence; a second oligonucleotide agent that selectively binds to a Y-chromosome nucleic acid sequence; and a third oligonucleotide agent that selectively binds to an autosomal chromosome nucleic acid sequence.

Embodiment 2. The method of embodiment 1, further comprising isolating sperm DNA from a population of sperm cells from a semen sample.

Embodiment 3. The method of embodiment 1, wherein laser ablated sperm cells are removed from said semen sample prior to isolating the sperm DNA.

Embodiment 4. The method of embodiment 1, wherein the population of cells comprises an X-skewed sperm population.

Embodiment 5. The method of embodiment 1, wherein the step of detecting comprises simultaneously detecting binding by the set of oligonucleotide agents.

Embodiment 6. The method of embodiment 1, wherein the step of detecting comprises detecting binding of the first oligonucleotide agent, the second oligonucleotide agent, and the third oligonucleotide agent, or combinations thereof.

Embodiment 7. The method of embodiment 5 or 6, wherein the step of detecting comprises admixing the sperm DNA with all of the oligonucleotide agents of the set under specific binding conditions.

Embodiment 8. The method of any one of embodiments 1 through 7, wherein the sperm cells comprise bovine sperm cells selected from a semen sample from *Bos taurus*, *Bos indicus*, or *Bos bubalis*, or hybrids thereof.

Embodiment 9. The method of any one of embodiments 1 through 8, wherein the step of detecting comprises amplifying at least one of an X-chromosome target site, a Y-chromosome target site, and a housekeeping target site.

Embodiment 10. The method of any one of embodiments 1 through 8, wherein prior to the step of detecting, the method comprises a step selected from the group consisting of amplifying at least one of an X-chromosome target site, a Y-chromosome target site, and a housekeeping target site.

Embodiment 11. The method of any one of embodiments 1 through 10, wherein the first oligonucleotide agent comprises: a first primer; a second primer; and a probe.

Embodiment 12. The method of any one of embodiments 1 through 10, wherein the second oligonucleotide agent comprises: a first primer; a second primer; and a probe.

Embodiment 13. The methods of any of the preceding embodiments, wherein the detecting comprises subjecting the DNA and oligonucleotides to thermocycling in the presence of a DNA polymerase enzyme, and detecting the amplification of X-chromosome, Y-chromosome, and housekeeping chromosomal nucleotide sequences.

Embodiment 14. The method of embodiment 11, wherein the X-chromosome primer sequences comprise SEQ ID NOS: 4 and 5, and the probe sequence comprises SEQ ID NO: 6.

Embodiment 15. The method of embodiment 12, wherein the Y-chromosome primer sequences comprise SEQ ID NOS: 7 and 8, and the probe sequence comprises SEQ ID NO: 9.

Embodiment 16. The method of any one of embodiments 10 through 14, wherein the probes include a detectable label.

Embodiment 17. The method of any one of embodiments 10 through 16, wherein the probes include a detectable label, the label selected from the group consisting of fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE),6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), and radioactive labels Embodiment 18. The method of any of the preceding embodiments, wherein the autosomal chromosome nucleic acid sequence is a glyceraldehyde 3-phosphate dehydrogenase (GAPDH) nucleotide sequence.

Embodiment 19. The method of any of the preceding embodiments, wherein the selective identification of the autosomal chromosome nucleic acid sequence comprises exposing the DNA to a third oligonucleotide agent, wherein the agent selectively binds to a GAPDH nucleotide sequence.

Embodiment 20. The method of embodiment 19, wherein the third oligonucleotide agent comprises primer sequences comprising SEQ ID NOS: 1 and 2, and a probe sequence comprising SEQ ID NO: 3.

Embodiment 21. A method of producing a validated sex-skewed population of sperm cells comprising: obtaining a population of sperm cells; subjecting the population of sperm cells to sex selection; collecting the sex selected sperm cells; assessing the sex-skew of a sample of the sex selected sperm cell population against a sex skew benchmark value; and validating the sex-skewed population.

Embodiment 22. The method of embodiment 21, wherein the sex skew benchmark value is at least 75% X.

Embodiment 23. The method of embodiment 21, wherein the sex selected sperm cells comprise at least 75% X cells.

Embodiment 24. The method of embodiment 21, wherein the assessing the sex skew in the sperm cell population comprises: obtaining a sample of a sex selected sperm cell population; exposing the DNA to a first oligonucleotide agent that selectively binds to an X-chromosome nucleic acid sequence; exposing the DNA to a second oligonucleotide agent that selectively binds to a Y-chromosome nucleic acid sequence; and detecting the sex skew in the population by detecting the binding of the first oligonucleotide agent or the second oligonucleotide agent to the X-chromosome and Y-chromosome nucleic acid.

Embodiment 25. The method of embodiment 21, further comprising isolating DNA from a sample of sex selected sperm cell population.

Embodiment 26. The method of embodiment 21, wherein laser ablated sperm cells are removed from the semen sample prior to isolating the sperm DNA.

Embodiment 27. The method of embodiment 21, wherein the sperm cell population comprises an X-cell selected sperm cell population.

Embodiment 28. The method of embodiment 24, further comprising exposing the sperm cells to a third oligonucleotide agent that selectively binds to an autosomal chromosome nucleic acid sequence.

Embodiment 29. The method according to any one of embodiments 21 through 29, wherein the assessing is carried out according to any of embodiments 1 through 20.

Embodiment 30. A kit for assessing the sex-skew in a population of cells comprising: a first oligonucleotide agent that selectively binds to an X-chromosome nucleic acid sequence; a second oligonucleotide agent that selectively binds to a Y-chromosome nucleic acid sequence; and a third oligonucleotide agent that selectively binds to an autosomal chromosome nucleic acid sequence.

Embodiment 31. The kit of embodiment 30, wherein the first oligonucleotide agent comprises oligonucleotide primer sequences SEQ ID NOS: 4 and 5, and oligonucleotide probe sequence SEQ ID NO: 6; second oligonucleotide agent comprises oligonucleotide primer sequences SEQ ID NOS:7 and 8, and oligonucleotide probe sequence SEQ ID NO: 9; and third oligonucleotide agent comprises oligonucleotide primer sequences SEQ ID NOS:1 and 2, and oligonucleotide probe sequence SEQ ID NO: 3.

Embodiment 32. The kit of embodiment 30, further comprising reagents and buffers suitable for performing a Polymerase Chain Reaction (PCR), a quantitative PCR (qPCR) reaction, or a Droplet digital PCR (ddPCR) reaction.

Embodiment 33. The kit of embodiment 30, further comprising reagents and buffers for removing non-viable sperm cells.

Embodiment 34. The kit of embodiment 30, further comprising reagents and buffers for isolating DNA from a sample of sperm cells.

Embodiment 35. A method of fertilizing a mammalian ovum, comprising: contacting a population of sperm cells to the ovum using artificial insemination (AI) or in vitro fertilization (IVF) with a validated population of sex skewed sperm cells.

Embodiment 36. The method of embodiment 35, wherein the population of sperm cells has been assessed according to the methods of any one of embodiments 1 through 18.

Embodiment 37. The method of embodiment 25, wherein the population of sperm cells has been produced according to the methods of any one of embodiments 19 through 23.

Embodiment 38. The method of embodiments 35 through 37, wherein at least 75%, at least 80%, at least 85%, at least 90%, or at least 95% of the sperm cells in the population are confirmed to bear an X-chromosome.

Embodiment 39. The method of embodiment 35 through 37, wherein at least 75%, at least 80%, at least 85%, at least 90%, or at least 95% of the sperm cells in the population are confirmed to bear an Y-chromosome.

Embodiment 40. An embryo or animal produced by the method of embodiments 35 through 39.

Embodiment 41. A method of producing a sex skewed sperm cell population comprising: obtaining a population of sperm cells; photolysing the cells treating the cells with a photoreactive DNA binding dye; suspending cells in a sperm separation and purification product subjecting the population of sperm cells to sex selection; collecting the sex selected sperm cells; and assessing the sex skew of a sample of the sex selected sperm cell population.

Embodiment 42. The method of embodiment 41, wherein the photoreactive DNA binding dye is ethidium monoazide (EMA).

Embodiment 43. The method of embodiment 41, where in the sperm selected sperm cells are bovine sperm cells selected from a semen sample from *Bos taurus, Bos indicus*, or *Bos bubalis*, or hybrids thereof.

Embodiment 44. The method of embodiment 41, wherein the sperm separation and purification product is BoviPure®.

Embodiment 45. The method of embodiment 41, wherein the sperm separation and purification product is Percoll®.

Embodiment 46. The kit of embodiment 30, wherein the first nucleotide agent comprises oligonucleotide primer sequences selected from the group consisting of SEQ ID NOS: 1-900, and oligonucleotide probe sequence selected from the group consisting of SEQ ID NOS: 1-900; the second nucleotide agent comprises oligonucleotide primer sequences selected from the group consisting of SEQ ID NOS:1-900, and oligonucleotide probe sequence selected from the group consisting of SEQ ID NOS: 1-900; and the third nucleotide agent comprises oligonucleotide primer sequences selected from the group consisting of SEQ ID NOS:1-900, and oligonucleotide probe sequence selecting from the group consisting of SEQ ID NO: 1-900.

Embodiment 47. The method of embodiment 19, wherein the third nucleotide agent comprises oligonucleotide primer sequences selected from the group consisting of SEQ ID NOS:1-900, and an oligonucleotide probe sequence selecting from the group consisting of SEQ ID NO: 1-900.

Embodiment 48. The method of embodiment 6, wherein the first nucleotide agent comprises oligonucleotide primer sequences selected from the group consisting of SEQ ID NOS: 1-900, and oligonucleotide probe sequence selected from the group consisting of SEQ ID NOS: 1-900; the second nucleotide agent comprises oligonucleotide primer sequences selected from the group consisting of SEQ ID NOS:1-900, and oligonucleotide probe sequence selected from the group consisting of SEQ ID NOS: 1-900; and the third nucleotide agent comprises oligonucleotide primer sequences selected from the group consisting of SEQ ID NOS:1-900, and oligonucleotide probe sequence selecting from the group consisting of SEQ ID NO: 1-900.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The following examples are offered by way of illustration only and should not be construed as intending to limit the invention in any manner Example 1: Assessing the Quality of Sex-Skewing of Sperm Cells Typical existing quality control for sex skewed sperm samples relies on FISH. However, the necessary scale-up for production quality control using FISH to determine the percentage of X-bearing cells is prohibitive, due to requisite labor hours. In addition, current FISH analysis does not quantify the desired product, but assumes X-chromosome cell counts based on the absence of signal from a Y-chromosome probe (a negative result assay). Further, the resources necessary to perform FISH quality control on one straw batch result in high cost, requiring 4 straws and more than 10 hours per day to complete 24 samples. Finally, even if an algorithm can be implemented to quantify signal for the otherwise manual assessment, data are sensitive to equipment, including bulbs which must be routinely replaced. Additionally, typical existing quality control for sex skewed sperm cell samples have limited accuracy and precision, by virtue of implementing a negative result assay (FISH) or lack of independent verification (re-running samples on the same cytometer used to skew). Accordingly, the present invention provides an effective and economical alternative to the commonly used FISH analysis, and provides improved accuracy and precision through direct independent assessment and quantification.

Digital droplet PCR (ddPCR) is an adaptation of quantitative PCR (qPCR) or realtime PCR in which a fluorescent probe reports amplification, but the reaction is divided into thousands of droplets. Template DNA for use in ddPCR is optimally distributed so each droplet contains one copy of the target template, so the readout is counting the number of fluorescent-positive droplets.

There are essentially five main steps involved in the ddPCR assay workflow: Genomic DNA isolation, droplet generation; thermocycling; droplet reading; and data analysis. For the assessment of sex skew, application of ddPCR must meet several basic requirements: the assay error rate should be at or below 1%. Although the error rate for FISH is not reliably ascertainable (as a negative result assay), an error rate at or below 1% is presumed to be comparable to, or more likely better than, the presumed variance of the FISH assay. Results should be available within three days of production of the sperm cell sample; and the technical failure should be less than 10%.

According to an exemplary embodiment of the present invention, a ddPCR assay was developed that would verify the cells counted per reaction using a housekeeping gene, independently assay X and Y chromosomes, quantify at least 2,000 cells across duplicate reaction wells, and achieve less than 1% variance in the percentage of X chromosome bearing cells detected in replicate reads.

X-skewed sperm cells are prepared by ablating Y-chromosome-bearing sperm cells, and the skewed samples are frozen. Two straws per batch (Straw Batch) are thawed and the cells are pelleted using a BoviPure density gradient and re-suspended in warmed media. Dead cells are removed by passing the re-suspended samples through glass wool. The collected intact cells are lysed in the presence of DTT, RNAse A, and proteinase K at 37° C. for 18 hours (1 hour). The lysed samples are then incubated at 55° C. for 1 hour, and DNA was prepared from the samples using the DNAdvance® Kit, according to the manufacturer's instructions. Concentration and purity of DNA samples was measured using a Nanodrop Lite®, and the DNA was diluted to 2.88 ng/µL.

ddPCR was carried out on the samples using the Bio-Rad®Droplet Digital™ PCR (ddPCR™) system, according to manufacturer's instructions. Droplets are generated using the QX200 Droplet Generator and analysis was carried out using the QX200 Droplet Reader, in the presence of the primers and probes listed in Table 2 below. Probes are labeled with carboxyfluorescein (FAM) or hexachlorofluorescein (HEX).

TABLE 2 ddPCR Primers and Probes

| Name | Sequence (5'-3') |
| --- | --- |
| X-D1438319 Plus #22 | AGAGAAGACCCATGATGCAAAGTCC (SEQ ID NO: 4) |
| X-D1438412 Minus #23 | CCTTTCATAGCATCCATGCCTCC (SEQ ID NO: 5) |

TABLE 2-continued ddPCR Primers and Probes

| Name | Sequence (5'-3') |
| --- | --- |
| Y-Y 1624 Plus #42 | TTAAGCCGGTCACAGTCCG (SEQ ID NO: 7) |
| Y-Y 1834 Minus #43 | GAGATAAAGAGCGCCTTTGTTAGCG (SEQ ID NO: 8) |
| GAPDH-279 Plus #48 | AGATTGTCAGGTGAGCGCAG (SEQ ID NO: 1) |
| GAPDH-463 Minus #49 | CCATAAGTCCCTCCACGATG (SEQ ID NO: 2) |
| X-D1438319 FAM | TCAACGATGGGAGCACTTTATGCTGT (SEQ ID NO: 6) |
| Y-Y 1624 HEX | CGAAATCCGTGTAGCCAATGTTAC (SEQ ID NO: 9) |
| GAPD 48/49 HEX | CAATGCCTCCTGCACCACCAAC (SEQ ID NO: 3) |
| GAPDH 48/49 FAM | CAATGCCTCCTGCACCACCAAC (SEQ ID NO: 3) |

Primer and Probe Specificity

Primers and probes are designed specifically based on the Bos_taurus_UMD_3.1.1 Assembly genome to target known autosomal genes, X chromosome genes, and Y chromosome genes. All primers are designed with Primer-Blast software (NCBI, USA) and span an intron/exon boundary. The resulting primers and probes are analyzed using BLAST (Basic sequence alignment tool: blast.ncbi.nlm.nih.gov/Blast.cgi) to ensure no predicted cross-species reactivity. The primers and probes are synthesized by and purchased from Integrated DNA Technologies (Coralville, Iowa). Probes are 5'-labeled with either FAM or HEX as the reporter and BHQ-1 or BHQ-2 (respectively) as the 3'-labelled quencher.

PCR primers are designed for bovine sequence, and are provided in Table 2, Table 3, Table 4 and Table 5. The primers are designed such that there are nopredicted cross-reaction with non-target genes, and melting temperatures are paired to maximize reaction efficiency. The successful primer and probe candidates are tested using PCR and qPCR. Testing demonstrated no amplification in the absence of bovine template (egg yolk present), and no amplification between mismatched primers/probes. In addition, the testing demonstrated amplification in every bull sample tested. In the present example, GAPDH is selected as the housekeeping gene, and the primer/probe combinations for X and Y chromosome detection are compared for accuracy and reproducibility.

DNA Extraction

Sexed semen units are obtained from the American Breeding Service division of Genus PLC. Sperm from two frozen-thawed, sexed semen straws or one frozen-thawed conventional semen straw (Genus, ABS Global, DeForest, Wis.) are centrifuged 10 minutes at 300×g through a Bovipure™ gradient (0.5 mL 40% layered over 0.5 mL 80%) (Nidacon, Sweden). Cells from sexed semen straws generated by laser ablation technology (Genus, IntelliGen, Winsdor, Wis.) are then run through a glass wool column (0.03 g in a 1 cc syringe packed to a 0.1 mL volume) by gravity drip (112X-475 borosilicate, Johns Manville, Denver, C)) to remove laser-killed cells. Cells are lysed in buffer containing 50 mM potassium chloride, 10 mM Tris base pH 8.3, 2.5 mM magnesium chloride, 0.5% Tween-20, 1 M dithiothreitol, 1

µg/µL RNAse A, and 40 mg/mL Proteinase K for 18±1 hours at 37° C. with constant rotation, followed by 1 hour at 55° C. with constant rotation. Genomic DNA is purified using the Agencourt DNAdvance Kit (Beckman Coulter, Indianapolis, Ind.) per manufacturer's instructions. Briefly, 200 µL lysate is mixed with 75 µL Bind I and 40 µL Bind 2 buffer (containing magnetic beads), 5 min at 750 rpm at 24° C. Plates are placed on the magnetic platform for 4 min, and the lysates removed from the wells. After binding step, beads are washed 3× with 150 µL 75% ethanol, shaking 5 min at 850 rpm at 24° C. and eluted in 25 µL of the supplied Elution Buffer, shaking 10 min at 1200 rpm at 37° C. DNA concentration is quantified on a NanoPhotometer (Implen, Germany).

PCR and qPCR

A 20 µL PCR reaction contains 2 µL of 10× DreamTaq Buffer, 1 µL 2 mM dNTP's, 1 µL 25 mM $MgCl_2$, 1 µL of each forward and reverse primer at an initial concentration of 5 µM, 0.2 µL DreamTaq DNA Polymerase, 0.5 µL BAM-HI-HF, and either a 5 µL or 15 µL of 4 ng/µL genomic DNA. Samples are thermocycled in a Labnet Multigene Optimax System under the following conditions: 30 s at 94° C., then 35 cycles of [30 s at 94° C., 30 s at 60° C., 30 s at 72° C.], followed 7 minutes at 72° C. then held at 4° C.

A 20 µL qPCR reaction contains 10 µL Bullseye TaqProbe qPCR MasterMix, 1 µL of each 10 µM forward and reverse primer, 1.5 µL 2 µM probe, and 5 µL genomic DNA. Samples are thermocycled in a PrimePro48 Real-Time PCR System (Techne, UK) as follows: 10 minutes at 95° C., 40 cycles of 15 s at 95° C., 60 s at 60° C. Data are analyzed using Techne Pro and ProStudy.

Agarose Gel Electrophoresis

PCR product is mixed with 3 µL of Amaranth Red dye and 20 µL of that mixture is loaded onto a 1% Agrose Gel with ethidium bromide using 100 bp ladder (New England Biolabs, Ipswich, Mass.). Gels are run at 100 V and imaged under UV light using an Alpha Innotech Corporation MultiImage Light Cabinet.

ddPCR Reaction

The BioRad QX200 Droplet Digital PCR (ddPCR) System is used essentially according to the manufacturer's instructions. The droplet count for the ddPCR assay is established at greater than or equal to 15,000 droplets per well. The critical copy count is >1000 copies/well. The DNA template input is optimized to minimize droplet occupancy while maximizing the number of copies per reaction. In addition, excess dNTPs are added to drive the reaction to completion. Restriction enzyme is included per the manufacturer's recommendations.

A 24 µL ddPCR master mix for each reaction contains 12 µL of 2× ddPCR supermix for Probes, 0.5 µL BAM-HI-HF, 0.5 µL of 2 µM dNTPs, 40 µM each forward and reverse primer to reach a final concentration of 500, 900, or 1300 nM, and 20 µM probe to reach a final concentration of 125, 150, 250, or 350 nM, and 5 µL 11 ng/µL or 2.88 ng/µL genomic DNA template. Droplets are generated using an Automated Droplet Generator with Automated Droplet Generation Oil (Bio-Rad, Hercules, Calif.). The final validated assay conditions used 900 nM primer with 125 nM probe for GAPDH (split into both FAM and HEX), 900 nM primer with 250 nM probe for the X chromosome (FAM only), and 1300 nM primer with 350 nM probe for the Y chromosome (HEX only). Thermocycling is performed in a BioRad C100 Touch Thermal cycler as follows: 10 minutes at 95° C., 40 cycles of [30 s at 94° C., 60 s at 60° C.], then 10 minutes at 98° C., followed by a 4° C. hold, with a ramp rate of 2° C./s. The BioRad QX200 Droplet Reader is used to count total droplets and quantify fluorescent signal per droplet. Amplicon copies per reaction and copies per µL are quantified using QuantaSoft and Analysis pro software (Bio-Rad, version 1.7.4.0917).

Figure 2:
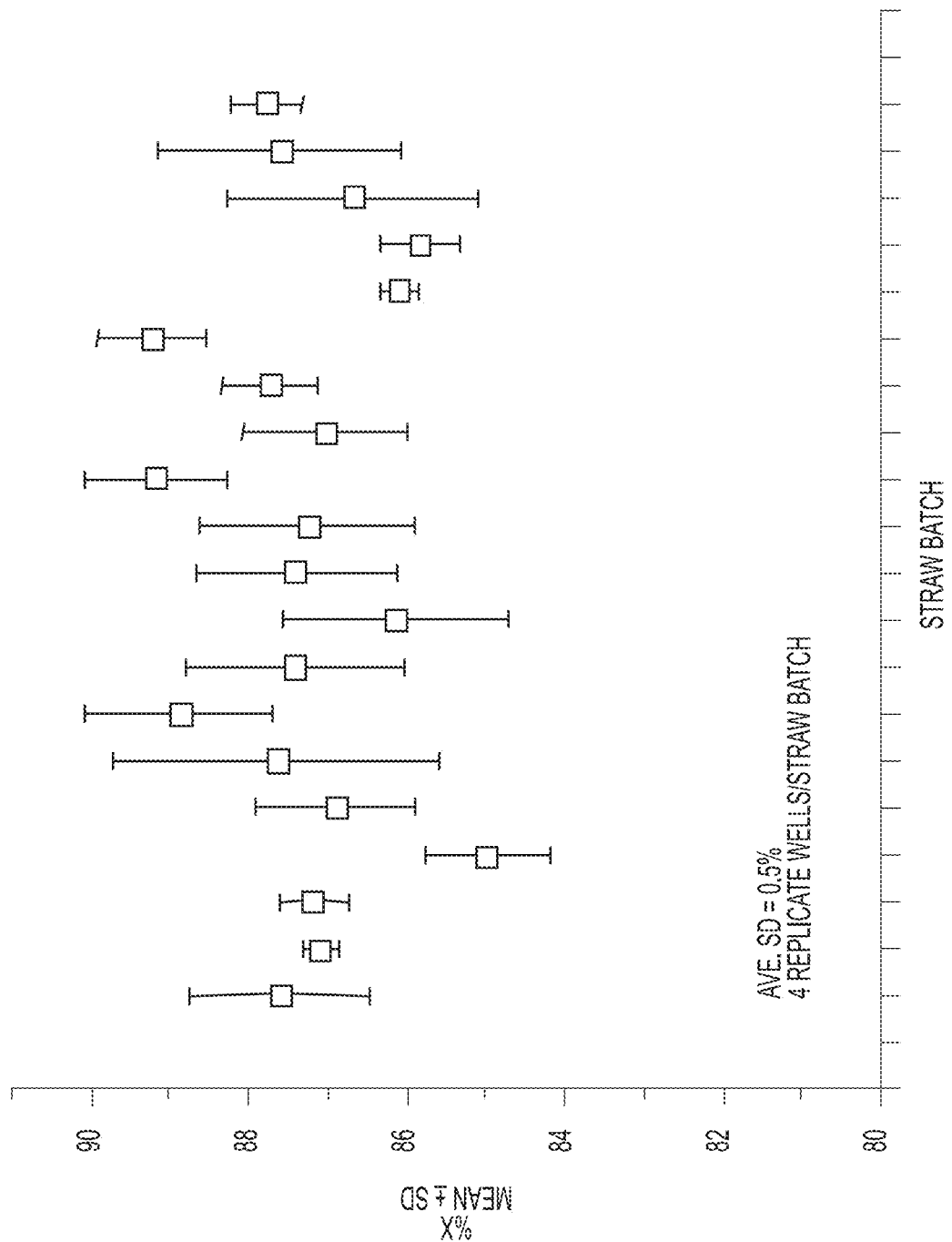
FIG. 2 shows repeat measures of individual samples (straw batch, X axis) using ddPCR according to an exemplary embodiment of the invention provided an average variance of 5% in absolute counts of X-chromosome. Four replicate wells are assayed for each straw batch.
Figure 3:
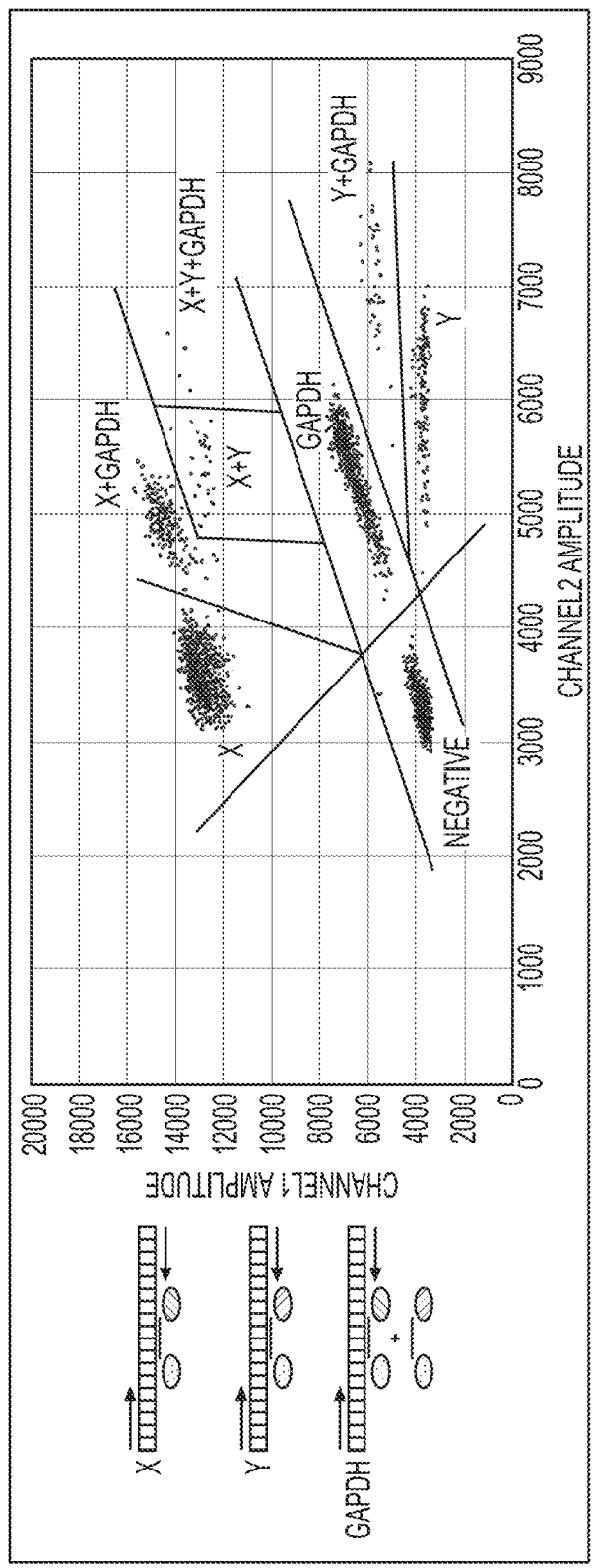
FIG. 3 shows optimized separation of the various droplet populations produced by the ddPCR assay, according to an exemplary embodiment of the invention.

Initial ddPCR demonstrates reproducible counts across repeat measures for each primer/probe combination (no more than 5% variance in absolute counts), and identified successful housekeeping gene, and X- and Y-chromosome primers and probes. Fluorophore conditions (including probe concentration) are adjusted to optimize population separation on scatter plots. As shown in FIG. 1, the assay achieved the critical copy count threshold of more than 1000 copies per well for all samples, as determined by GAPDH copies per well. Further, as shown in FIG. 2, the variance of the percentage X-chromosome (as a function of total cells represented) in repeat measurements of the same sample was 0.5% SD. Importantly, the scatter plot of the populations detected by the different probe sets demonstrated optimal separation, as shown in FIG. 3.

Figure 4:
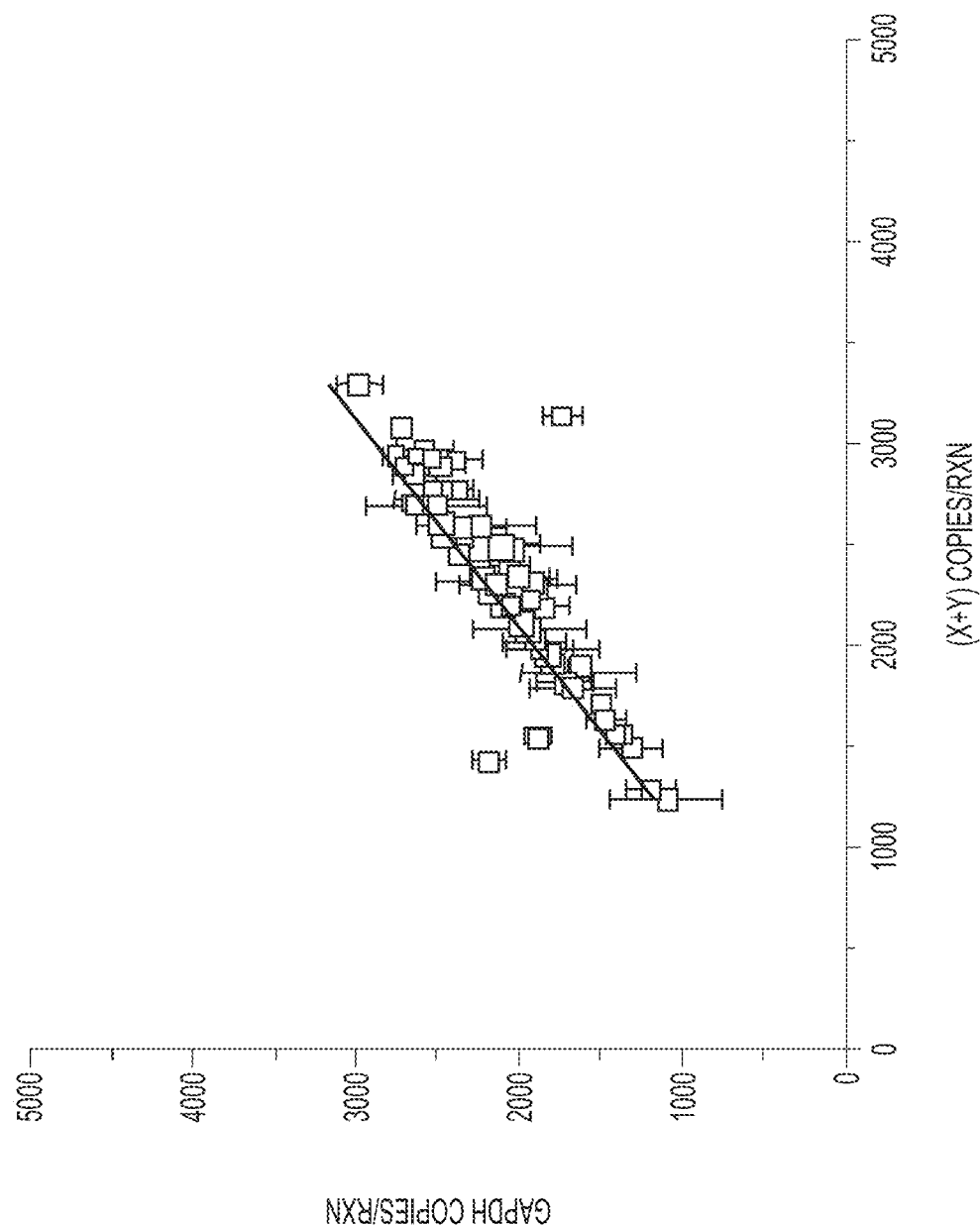
FIG. 4 shows that a ddPCR assay for assessing X-skew according to an exemplary embodiment of the invention provides a direct linear correlation (slope=1) between the detection of copies of X and Y chromosomes and the detection of a reference housekeeping gene (GAPDH). The intercept is −14.51±106.7, the slope is 0.96±0.04, Pearson's R value is 0.932, and the R-square value is 0.852.
Figure 5:
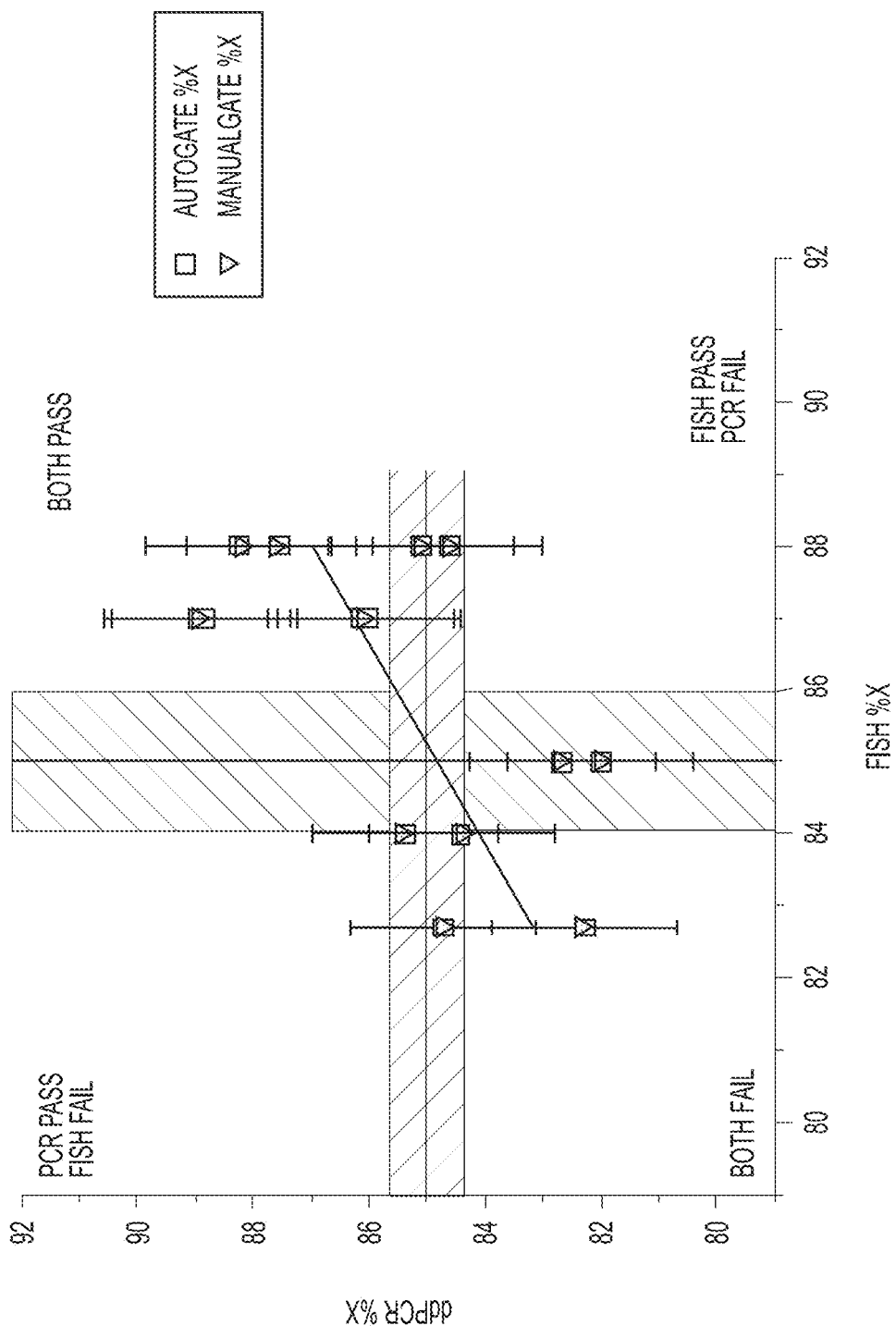
FIG. 5 shows the error rate for the ddPCR assay according to an exemplary embodiment of the invention, which is at least comparable to the industry standard FISH assay. The graph shows a comparison of the percentage of X-chromosome bearing sperm cells, as detected by the standard FISH assay and the ddPCR assay according to the present invention. The intercept is 24.21±22.6, the slope is 0.72±0.2, residual sum of squares is 42.97, Pearson's R value is 0.616, and the R-square value is 0.380.

To ensure accuracy and reliability of the assay, and thereby achieve effective assessment of sex skewing, the combined number of copies of X chromosome and Y chromosome in a given sample needs to have a linear relationship with the number of copies of the housekeeping gene (GAPDH) detected. As shown in FIG. 4, the ddPCR assay according to an exemplary embodiment of the invention demonstrated a direct linear correlation (slope=1) between copies of X+Y and GAPDH. In addition, testing showed that the tolerance of the ddPCR assay was equal to or superior to the FISH assay. As shown in FIG. 5, a comparison of the percentage of X-chromosome bearing sperm cells—as detected by the standard FISH assay and the ddPCR assay according to the present invention—illustrates that the results of the two assays correlate well, and importantly there are no instances in which a sample passed one assay while failing the other. This demonstrates that the error rate for the ddPCR assay is at least comparable to the industry standard FISH assay.

Figure 6:
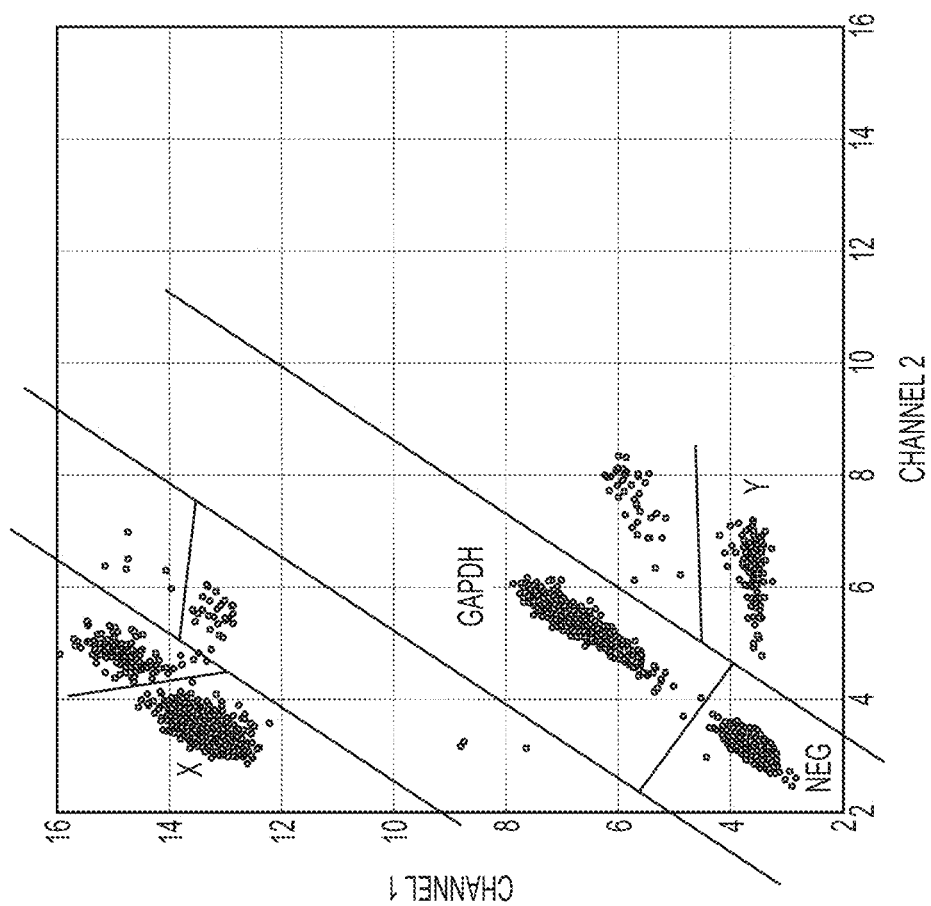
FIG. 6 shows the ddPCR gating strategy used according to an exemplary embodiment of the invention.

To effectively differentiate the PCR products produced in each droplet, it is necessary to develop an effective gating system that could correctly and consistently gate seven different droplet populations, corresponding to X, Y, or GAPDH signal, and every possible combination of multiple occupancy. In addition, the gating and detection needed to include Poisson correction for multi-occupancy for each individual probe (ex: 2 copies of X/droplet). Further, in order to minimize the variations between and among assays, the % X is quantified as number of detected copies of X divided by the total number of detected copies of X and Y. The accuracy of this quantification is only confirmed if the detected number of copies of GAPDH fell within two standard deviations of the combined number of X+Y. The gating strategy for differentiation of the droplet populations, is shown in FIG. 6. Initial efforts to utilize ready-made clustering algorithms are unsuccessful. The developed gating strategy is a generalized clustering algorithm to fit the type of data, but required a priori assumptions about data in order to overcome the inherent fragility of the generalized algorithm.

A further requirement of the analysis system is the need to flag samples as "Error" for rerun. Samples are flagged in four different circumstances: (1) Where the duplicate wells provided a % X with variance greater than 0.8% (=1.635 SD replicate variance to provide 95% confidence) and the duplicates fall on either side of the 85% mark; (2) where GAPDH and/or X counts fall below 1000 copies/well; (3)

where mean fluorescence is below detection range; and (4) where X+Y is different from GAPDH total copies by more than 2 standard deviations.

Figure 7:
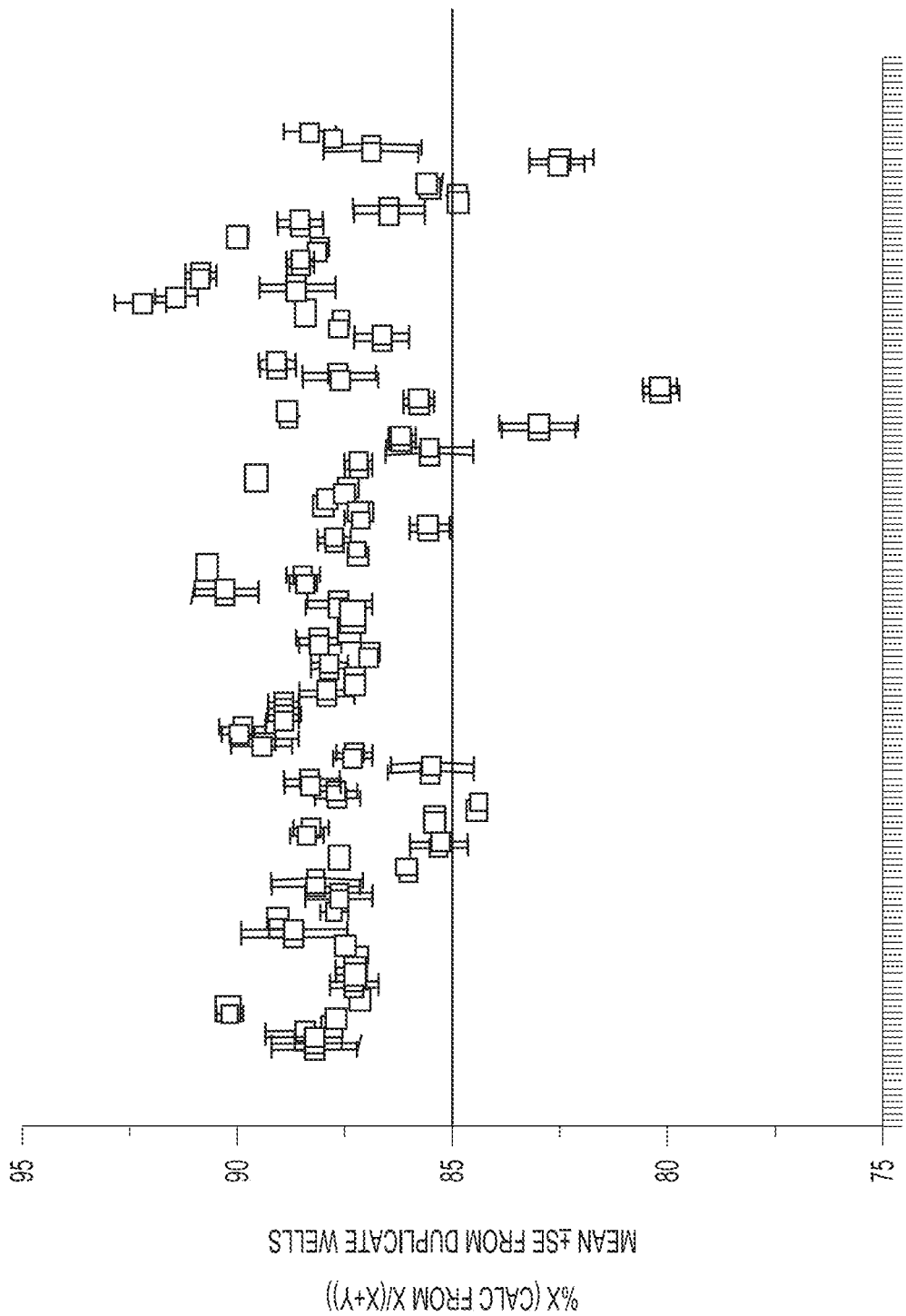
FIG. 7 shows that manual gating and auto-gating using the ddPCR gating strategy shown in FIG. 6 do not produce differences in detection. The gating strategies are compared using 73 different straw batches.
Figure 8:
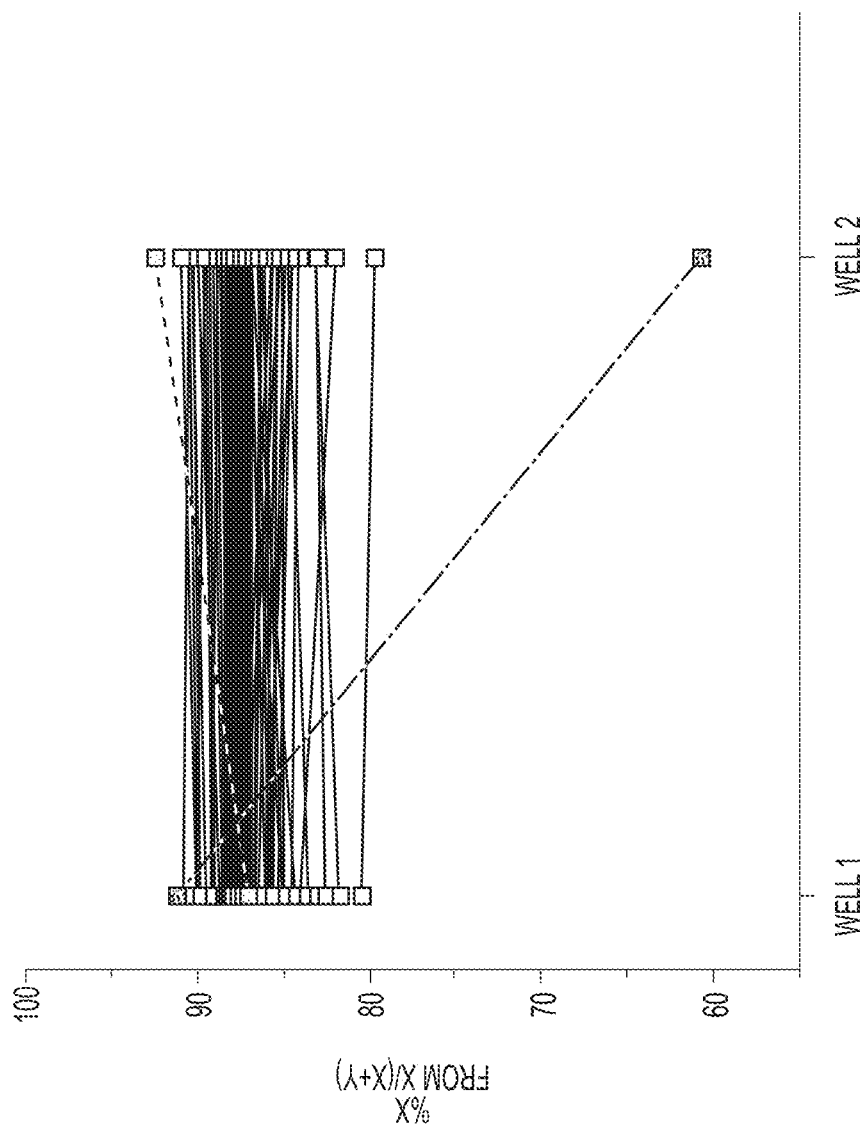
FIG. 8 shows repeats due to replicate failure in only 2% of samples, using the gating and analysis strategies for ddPCR, according to an exemplary embodiment of the invention. Two of the 92 samples failed replicate criteria.

The efficacy of the gating and analysis system is tested with sex-skewed sperm cell samples. The gating strategy developed did not yield demonstrably different results from manually drawing gates around individual populations, as shown in FIG. 7. Repeat analysis of samples using the gating and analysis strategies demonstrated that only 2% of sex-skewed samples (2 of 92 samples) failed the analysis criteria due to replicate failure, as shown in FIG. 8. Overall, as demonstrated in FIG. 9, ddPCR assessment of sex-skewed sperm cell samples was at least as effective for evaluating the efficacy of the skew as historical FISH analysis. Using a set of 158 samples, 91% pass a % X cutoff of 85%, with a population mean of 87±1.7%.

Example 2: Assessing the Quality of EMA-ddPCR Protocol

An alternative protocol to the gender selected semen (GSS) sex skewing protocol includes using ethidium mono-azide (EMA) to remove DNA from dead cells instead of glass wool as described above. EMA is DNA-intercalating dye that penetrates only into cells with damaged membranes or binds to free DNA to inhibit subsequent amplification, and allowing only amplification of DNA from live cells. Additionally, when cells are stained with EMA and exposed to light prior to permeabilization, the EMA is covalently linked to the DNA in the dead cells and cannot subsequently leak out.

Briefly, X-skewed sperm cells are prepared by ablating Y-chromosome-bearing sperm cells, and the skewed samples are frozen. Two straws per batch (Straw Batch) are thawed and the cells are treated with EMA for 30 mins using a PMA-Lite™ photolysis device. The cells are pelleted using BoviPure® density gradient and re-suspended in warmed media. The collected intact cells are either frozen or lysed in the presence of DTT, RNAse A, and proteinase K at 37° C. for 18 hours (1 hour). The lysed samples are then incubated at 55° C. for 1 hour, and DNA is prepared from the samples using the DNAdvance®Kit, according to the manufacturer's instructions. Concentration and purity of DNA samples was measured using a Nanodrop Lite®, and the DNA is diluted to 2.88 ng/μL.

As described above, ddPCR is carried out on the samples using the Bio-Rad® Droplet Digital™ PCR (ddPCR™) system, according to manufacturer's instructions. Droplets are generated using the QX200 Droplet Generator and analysis is carried out using the QX200 Droplet Reader, in the presence of the primers and probes listed in Table 2 above. Probes are labeled with carboxyfluorescein (FAM) or hexachlorofluorescein (HEX).

Example 3: Determination of Sex Skew in Bovine Semen Samples and Assay Validation Primer sets are tested for both the X and Y chromosomes. Three X-chromosome airs are tested:

TABLE 3

*Bos Taurus* X Chromosome Primers

| Label | target Gene | Primer Sequences (SEQ ID NO) (5'-3') |
|---|---|---|
| X₁ | Bos taurus KLHL4 | AGAGAAGACCCATGATGCAAAGTCC (SEQ ID NO: 237) CCTTTCATAGCATCCATGCCTCC (SEQ ID NO: 844) |
| X₂ | Bos taurus KLHL4 | GCACACTCACTAGGAGAAACAAACC (SEQ ID NO: 222) TGGAACTGCTCCTCAAATCTGC (SEQ ID NO: 845) |
| X₃ | Bos taurus X-1437318 | TTACCTGAGAGAAGACCCATGATGC (SEQ ID NO: 846) CTCCTACAGCATAAAGTGCTCCC (SEQ ID NO: 847) GACTCAAGTCATTGAAGTCTGCTCC (SEQ ID NO: 848) GAGCTTTGTACAGCCTTGGGC (SEQ ID NO: 849) |

TABLE 4

*Box Taurus* Y Chromosome Primers

| Label | Target Gene | Primer Sequences | Probe Sequence | Amplicon Length |
|---|---|---|---|---|
| Y₁ | Y Ch. 786 | AAGCCTGGGCCACAATAAGG (SEQ ID NO: 850) AAGAGCGCCTTTGTTAGCG (SEQ ID NO: 852) | TCGGCGGACTTTCCCTGTAACAAA (SEQ ID NO: 851) | 137 bp |
| Y₂ | Y Ch. 1427 | ATTAAGCCGGTCACAGTCCG (SEQ ID NO: 853) AAAGAGCGCCTTTGTTAGCG (SEQ ID NO: 854) | TCGGCGGACTTTCCCTGTAACAAA (SEQ ID NO: 855) | 207 bp |
| Y₃ | Y Ch. 1695 | GAGCCTGGACTTTCTTGTGC (SEQ ID NO: 856) ATAAAGAGCGCCTTTGTTAGCG (SEQ ID NO: 857) | TTCAATATTGACTTCCTTACTCT (SEQ ID NO: 858) | 70 bp |
| Y₄ | Y Ch. 1650 | TTGGCTACACGGATTTCGGC (SEQ ID NO: 859) GATAAAGAGCGCCTTTGTTAGCG (SEQ ID NO: 860) | AAATAAGCACAAGAAAGTCCAGGC (SEQ ID NO: 861) | 116 bp |

TABLE 4-continued

Bos Taurus Y Chromosome Primers

| Label | Target Gene | Primer Sequences | Probe Sequence | Amplicon Length |
|---|---|---|---|---|
| $Y_5$ | | CATTGGCTACACGGATTTCGG (SEQ ID NO: 862) GAGATAAAGAGCGCTTTGTTAGC (SEQ ID NO: 863) | | |
| $Y_6$ | Y Ch. 1804 | TACTCTCGCTAACAAAGGCG (SEQ ID NO: 864) TGACTCAAGCAGTTTTGGTGC (SEQ ID NO: 865) | ACTACAGTTTCACCTGCGACTTAA (SEQ ID NO: 866) | 209 bp |
| $Y_7$ | Y Ch. 1717 | TTGGCTACACGGATTTCGGC (SEQ ID NO: 867) AGAGCGCCTTTGTTAGCG (SEQ ID NO: 868) | AAATAAGCACAAGAAAGTCCAGGC (SEQ ID NO: 869) | 111 bp |
| $Y_8$ | | CTTACTCTCGCTAACAAAGGCG (SEQ ID NO: 767) GAACTCAAGCAGTTTTGGTGC (SEQ ID NO: 870) | | |
| $Y_9$ | Y Ch. 1803 | TTACTCTCGCTAACAAAGGCG (SEQ ID NO: 871) AACTCAAGCAGTTTTGGTGC (SEQ ID NO: 872) | ACTACAGTTTCACCTGCGACTTAA (SEQ ID NO: 873) | 208 bp |
| $Y_{10}$ | | TTAAGCCGGTCACAGTCCG (SEQ ID NO: 874) GAGATAAAGAGCGCCTTTGTTAGCG (SEQ ID NO: 875) | | |

Figure 10A:
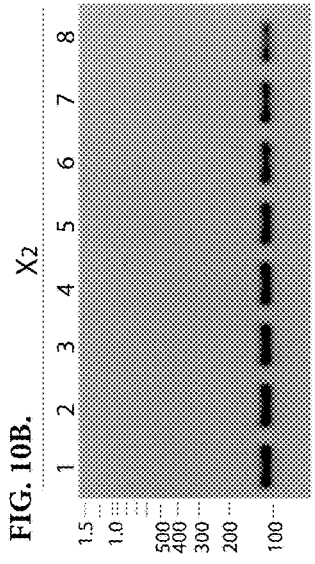
FIG. 10A shows PCR products of primer set $X_4$ tested on eight different sires to determine consistency in amplification.
Figure 10B:
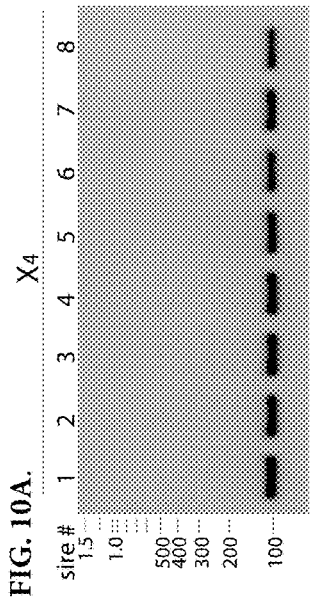
FIG. 10B shows PCR products of primer set $X_2$ tested on eight different sires to determine consistency in amplification.
Figure 10C:
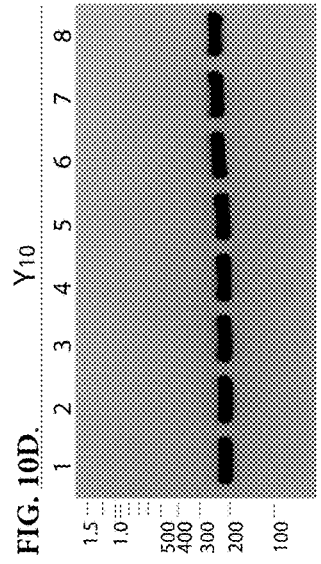
FIG. 10C shows PCR products of primer set $X_1$ tested on eight different sires to determine consistency in amplification.
Figure 10D:
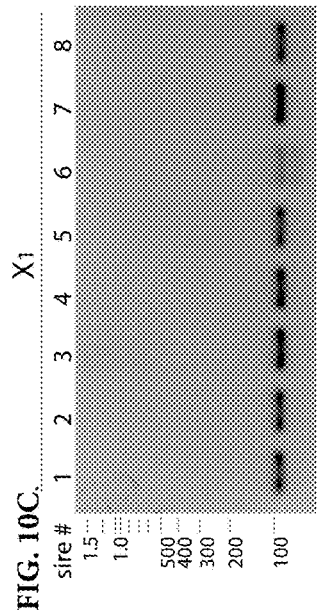
FIG. 10D shows PCR products of primer set $Y_{10}$ tested on eight different sires to determine consistency in amplification.
Figure 10E:
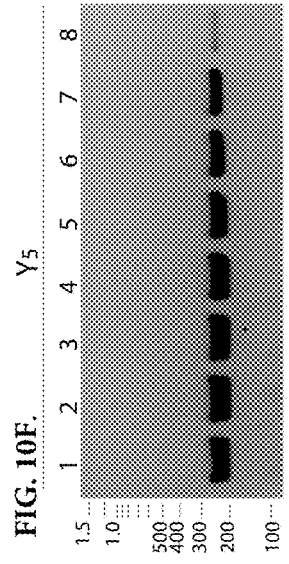
FIG. 10E shows PCR products of primer set $Y_8$ tested on eight different sires to determine consistency in amplification.
Figure 10F:
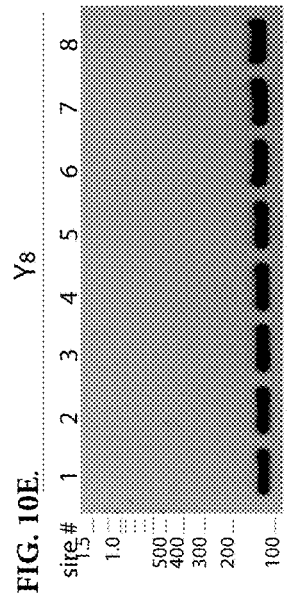
FIG. 10F shows PCR products of primer set $Y_5$ tested on eight different sires to determine consistency in amplification.

To determine variance among individuals, all primer sets are tested on eight different sires to determine whether the targets are consistently amplified in different animals. As shown in FIGS. 10C and 10F, respectively, primer sets $X_1$ and $Y_5$ failed to produce a consistent amplification product across all tested sires and are therefore unsuitable for sex-skew assays.

Figure 11:
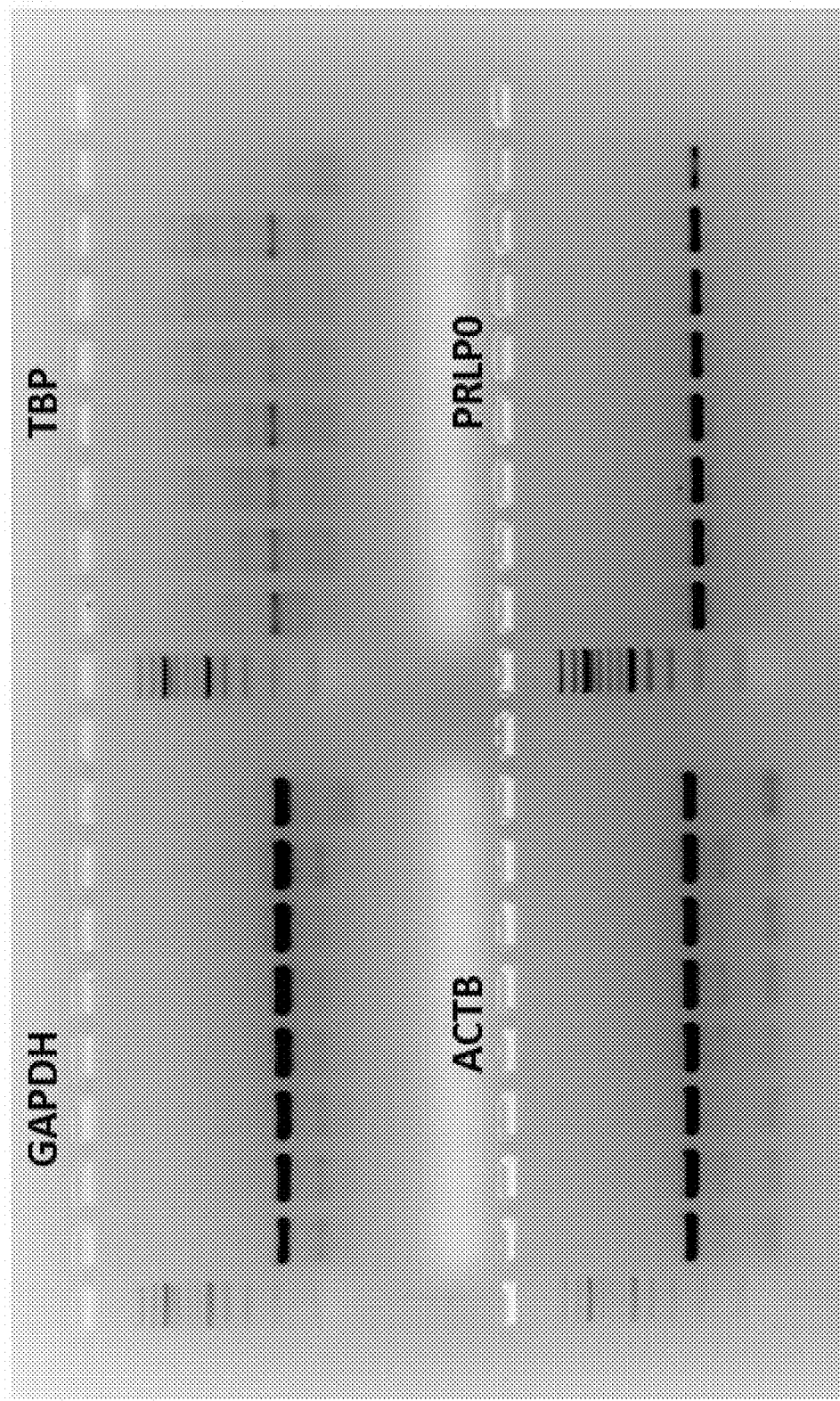
FIG. 11 shows the results four autosomal targets tested as candidate reference genes, Glyceraldehyde 3-phosphate dehydrogenase (GAPDH), TATA-box binding protein (TBP), β-actin (ACTB), and prolactin-like protein O (PRLPO), using DNA from eight different sires. The sires used include Cruz 1 Crux HO16443 (lane 1), Armitage HO14961 (lane 2), Protector JE3886 (lane 3), LiftOff HO16679 (lane 4), Maynard HO16470 (lane 5), Pistol JE4025 (lane 6), Virginian JE3949 (lane 7), and Up River ANG1856 (lane 8).

For normalization, detection of levels of DNA of reference or "housekeeping" genes, whose expression levels should not significantly vary among or within individuals or samples and are located on autosomal chromosomes are used. Four autosomal targets are tested as candidate reference genes: Glyceraldehyde 3-phosphate dehydrogenase (GAPDH), TATA-box binding protein (TBP), β-actin (ACTB), and prolactin-like protein O (PRLPO). The four autosomal targets are assessed using DNA from eight different sires. As shown in FIG. 11, GAPDH and ACTB show consistent amplification across all samples, while amplification of TBP revealed variable amplification and is not suitable for sex-skew determination assays.

TABLE 5

Autosomal genes for normalization

| Label | Target Gene | Primer Sequences (5'-3') | Probe Sequence (5'-3') | Amplicon Length |
|---|---|---|---|---|
| ACTB | ACTB | CCAACCGTGAGAAGATGACC (SEQ ID NO: 876) GAACCTGCAAAGTTCCAAAGGAG (SEQ ID NO: 877) | CCCTTTGCCTCACCCTTCTCACT (SEQ ID NO: 878) | 162 bp |
| | | GACGACATGGAGAAGATCTGGC (SEQ ID NO: 879) TCAGCTCAGAGAAGAAAGTCCTA (SEQ ID NO: 880) | CCCTTTGCCTCACCCTTTCTCACT (SEQ ID NO: 881) | 240 bp |
| B2M | B2M | CTTTCTACCTGCTGTCCCACG (SEQ ID NO: 882) TACGCAGAGGTTTAATAACATTCCC (SEQ ID NO: 883) | AGCTGCCGAGTGAAACACGTTACT (SEQ ID NO: 884) | 233 bp |
| GAPDH* | GAPDH* | AGATTGTCAGGTGAGCGCAG (SEQ ID NO: 885) CCATAAGTCCCTCCACGATG (SEQ ID NO: 886) | CAATGCCTCCTGCACCACCAAC (SEQ ID NO: 887) | 185 bp |

TABLE 5-continued

Autosomal genes for normalization

| Label | Target Gene | Primer Sequences (5'-3') | Probe Sequence (5'-3') | Amplicon Length |
|---|---|---|---|---|
| HMBS | HMBS | CAGCATGAAGATGGCCCTG (SEQ ID NO: 888) GGATGTAGGCACTGGGTGAC (SEQ ID NO: 889) | ATCTTGCACGGCAGCTCAATGAAG (SEQ ID NO: 890) | 230 bp |
|  |  | TATGCTTGACCACGGAAGCC (SEQ ID NO: 197) GATCGTTCAGCAATGCAGCG (SEQ ID NO: 891) | AAGTTCGAGCCAAAGACCAGGACA (SEQ ID NO: 892) | 227 bp |
| HPRT1 | HPRT1 | TTTGAACAGACTGATGGTTCCC (SEQ ID NO: 22) CAAGAAGTGTCACCCTCGCC (SEQ ID NO: 893) | ACATCCTTAGAGCTGGAACTTGGCC (SEQ ID NO: 894) | 99 bp |
| PRLP0 | PRLP0 | GTAGGCCCTCAGTACATGGC (SEQ ID NO: 895) TTTCTCTCCTCAGTGACATCG (SEQ ID NO: 896) | AGGGATTGCCACGCAGGGTTTAA (SEQ ID NO: 897) | 206 bp |
| TBP | TBP | TTAAACAAGTACCAAACACCACGC (SEQ ID NO: 898) AGCAGCCATTACGTTGTCTTCC (SEQ ID NO: 899) | CTACCCTATTCTGAAGGGTTTCA (SEQ ID NO: 900) | 199 bp |

In order to eliminate temporal effect of PCR reactions, amplicons for quantitative and quasi-quantitative PCR-based assays are typically size-matched due to differences in amplification efficiency. Few candidate genes for sex-skew assays provided specific and consistent amplification. Though the amplicons for the present embodiment are not size-matched, they unexpectedly provided robust and reproducible sex-skew determinations. The present amplicons did no exhibit significant size-based effects. Thus, additional amplicons may be identified and tested for robustness and amplicon design does not need require that the various amplicons be size matched. This expands the number and type of genes that are suitable for sex-skew assays.

Example 4: Optimized Triplex Chemistry for Sex Skew Quantification by ddPCR

Sexed semen and DNA samples are prepared as described in Example 1 above. ddPCR is performed according to Example Two. Input quantities for template genomic DNA and each primer and probe are iteratively adjusted until maximal separation of the fluorescent droplet populations is achieved, while assaying the maximal total number of cells. Iterative data are not shown, but FIG. 3 presents an example fluorescent scatter plot from a single assay well run under optimized conditions such that at least 1000 cells are interrogated; each droplet population identified on the scatter plot demonstrates clear population separation.

Both GAPDH and B2M are candidate autosomal "cell counters" based on detection threshold and minimal CT variance in qPCR. To evaluate which of these provide both the most accurate cell counting tool in ddPCR, each are tested to determine whether the total copies counted per ddPCR reaction corresponds to the predicted copy number based on bovine genomic molecular weight, ng input DNA, and the haploid nature of sperm cells. While GAPDH copy counts reflected nanogram input DNA, B2M consistently reports twice the predicted copy number (data not shown) and is therefore excluded. This result demonstrates the need to carefully select and validate the autosomal chromosome nucleic acid for targeting.

Figure 12:
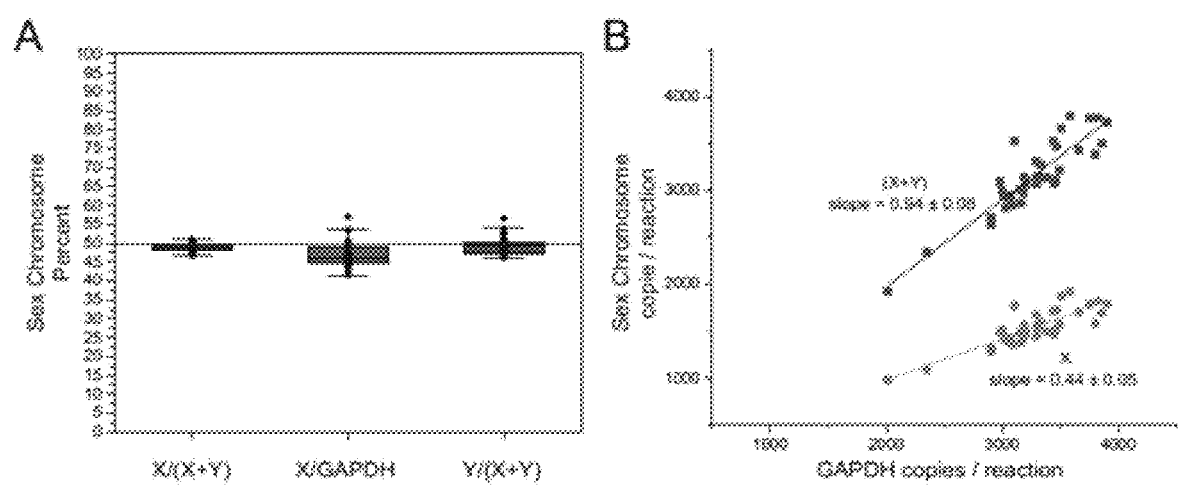
FIG. 12 (A.) Box plot depicts the percent sex chromosome in genomic DNA isolated from frozen-thawed conventional semen, calculated as X/(X+Y), X/GAPDH, and Y/GAPDH, n=40 unique Holstein sires. All three calculations reveal a 50/50 sex chromosome ratio. (B.) Scatter plot of GAPDH copies counter per reaction vs. sex chromosome copies per reaction revealed a linear slope of 0.94±0.08 for (X+Y), demonstrating the autosomal marker tallied the same total number of cells as the additive sum of X+Y copies. The linear slope for GAPDH vs. X chromosome copies/reaction was 0.44±0.05, consistent with a predicted 50% X chromosome distribution in conventional semen.

Using the optimized chemistry, genomic DNA from conventional bovine semen straws are analyzed using the ddPCR sex skew assay as validation. Samples obtained from unselected sperm populations are expected to present a ~50% X, 50% Y chromosome ratio. The percentage of sex chromosome amplicon is quantified from genomic DNA as a function of either total X+Y amplicons or total autosomal (GAPDH) amplicons from n=40 Holstein sires. FIG. 12A demonstrates that X and Y chromosome amplicon representation equaled 50% when calculated as X/(X+Y), X/GAPDH, or Y/GAPDH. FIG. 12B plots GAPDH copies quantified vs. total quantified (X+Y) copies; a linear slope of 0.94±0.08 demonstrates the total number of sex chromosomes counted is equal to the number of autosomal GAPDH copies counted. FIG. 12B also plots GAPDH copies counted versus X chromosome copies counted, where a slope of 0.44±0.05 corresponds to 50% X chromosome distribution in conventional semen. These data from conventional semen verify the ddPCR sex skew assay reports the expected sex chromosome distribution across all genomic templates (sires) tested.

Example 5: Dynamic Range of Optimized ddPCR

Figure 13:
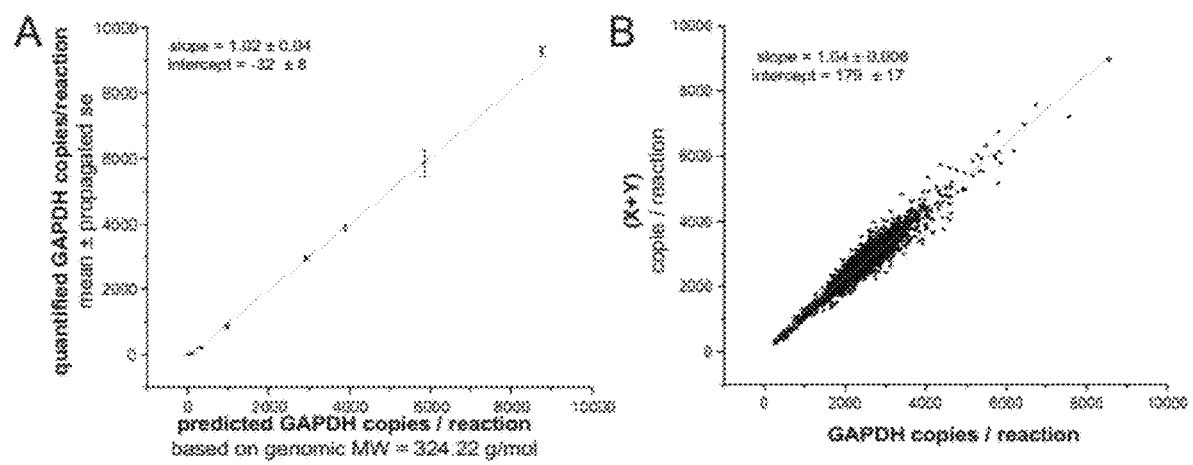
FIG. 13 shows GAPDH copies per reaction aligned with predicted values, with a linear dynamic range spanning 0.3 to 27 ng genomic DNA input. (A.) GAPDH copies counted per reaction from triplex ddPCR sex skew assays are plotted as a function of the predicted number of copies per reaction calculated based on nanogram input DNA and a genomic molecular weight of 324.22 g/mol, revealing a linear slope of 1.02±0.04. B. GAPDH copies counted per reaction from triplex ddPCR sex skew assays are plotted as a function of the predicted number of copies per reaction calculated based on nanogram input DNA and a genomic molecular weight of 349.65 g/mol, revealing a linear slope of 0.95±0.04. For both panels, genomic DNA is isolated from frozen-thawed sex skewed semen, n=4 unique sires (2×Jersey, 2×Holstein) assayed in triplicate.

The dynamic range for the GAPDH primer/probe set is defined by quantifying the number of copies counted per triplex ddPCR reaction (X, Y, GAPDH primer/probes) across a range of ng DNA input doses from frozen-thawed, sexed semen straws, n=4 sires (2 Jersey, 2 Holstein) read in triplicate reactions. FIG. 13 plots predicted copy number per reaction versus GAPDH copies counted, revealing a slope of 1 when using a *Bos taurus* genomic molecular weight of either 324.22 g/mol (FIG. 13A, slope=1.02±0.04), or 349.65 g/mol (FIG. 13B, slope=0.95±0.04). The linear dynamic range for accurate GAPDH copy counts in the sex skew assay is from 0.3-27 ng genomic DNA/20 μL ddPCR reaction.

BoviPure™ gradient centrifugation followed by glass wool column purification is used to eliminate non-viable sperm from the sample prior to genomic DNA extraction.

Briefly, Sperm from two frozen-thawed, sexed semen straws or one frozen-thawed conventional semen straw (Genus, ABS Global, DeForest, Wis.) are centrifuged 10 minutes at 300×g through a Bovipure™ gradient (0.5 mL 40% layered over 0.5 mL 80%) (Nidacon, Sweden). Cells from sexed semen straws generated by laser ablation technology (Genus, IntelliGen, Winsdor, Wis.) are then run through a glass wool column (0.03 g in a 1 cc syringe packed to a 0.1 mL volume) by gravity drip (112X-475 borosilicate, Johns Manville, Denver, Colo.)) to remove laser-killed cells. Cells are lysed in buffer containing 50 mM potassium chloride, 10 mM Tris base pH 8.3, 2.5 mM magnesium chloride, 0.5% Tween-20, 1 M dithiothreitol, 1 µg/µL RNAse A, and 40 mg/mL Proteinase K for 18±1 hours at 37° C. with constant rotation, followed by 1 hour at 55° C. with constant rotation. Genomic DNA is purified using the Agencourt DNAdvance Kit (Beckman Coulter, Indianapolis, Ind.) per manufacturer's instructions. Also, briefly, 200 µL lysate is mixed with 75 µL Bind I and 40 µL Bind 2 buffer (containing magnetic beads), 5 min at 750 rpm at 24° C. Plates are placed on the magnetic platform for 4 min, and the lysates are removed from the wells. After binding step, beads are washed 3× with 150 µL 75% ethanol, shaking 5 min at 850 rpm at 24° C. and eluted in 25 µL of the supplied Elution Buffer, shaking 10 min at 1200 rpm at 37° C. DNA concentration was quantified on a NanoPhotometer (Implen, Germany).

Genomic DNA from frozen-thawed sexed semen straws representing n=220 sires (including Holstein, Jersey, and Angus) is analyzed for sex skew using the ddPCR assay (12 ng input template DNA). The assay is maintained the 1:1 linear relationship between total GAPDH and (X+Y) copies counted per reaction.

Figure 14:
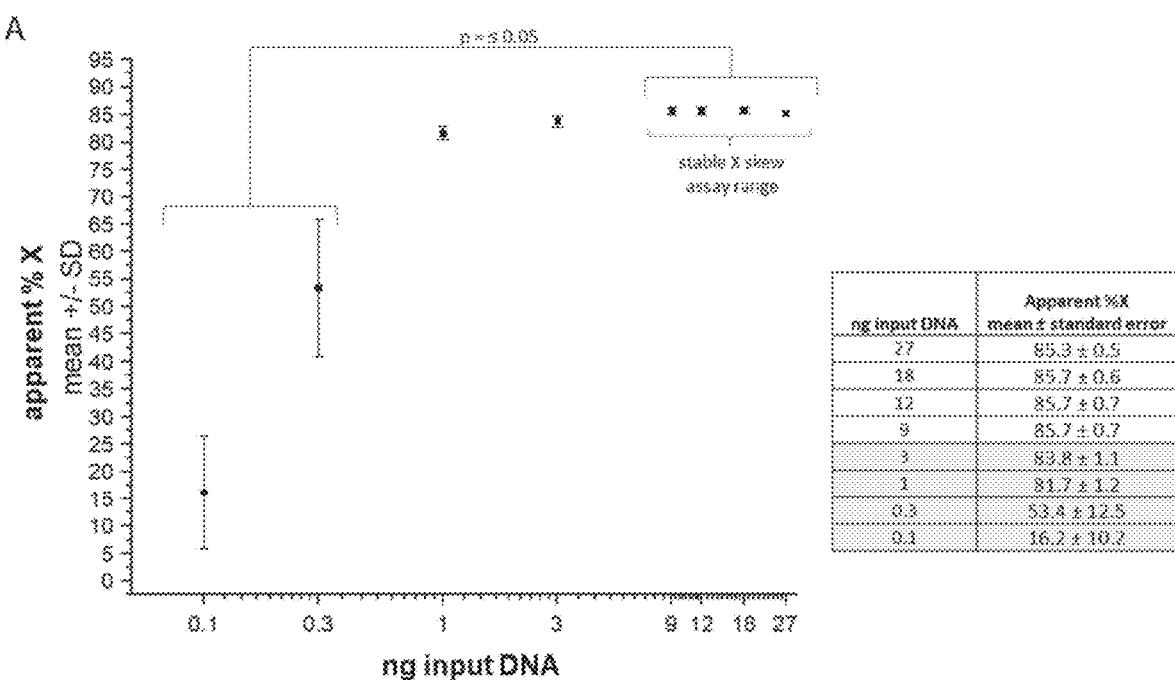
FIG. 14 shows a triplex ddPCR sex skew assay provides reproducible % X quantification from 9-27 ng genomic DNA input. Semi-log scatter plot depicts the calculated (apparent) % X chromosome representation in genomic DNA from sexed semen across a range of ng DNA input. There was no difference in the apparent percent X with input DNA ranging from 9-27 ng. The apparent % X was significantly lower with DNA input ranging from 0.1-0.3 ng (one way ANOVA, Bonferroni means comparison, p<0.05), n=4 unique sires (2×Jersey, 2×Holstein) assayed in triplicate.

Example 6: Determination of Input Range for Precise Sex Skew Assay Based on Percent X Chromosome While total autosomal counts demonstrated a wide linear assay range, a sex skew assay must also reliably provide a precise value for the calculated % X (or % Y chromosome). To determine the input DNA range across which the calculated % X is stable, sex skew is quantified as a function of nanogram DNA input. FIG. 14 plots apparent % X as a function of ng input DNA, demonstrating that between 9 and 27 ng total genomic DNA per reaction, the calculated % X did not change, exhibiting a standard error less than 1% (error propagated from duplicate samples from sexed semen n=4 unique sires). The apparent % X dropped when input DNA is below 3 ng, such that at 0.3 and 0.1 ng genomic DNA, the apparent skew is statistically different from the stable assay range (one-way ANOVA, p<0.05, Bonferroni means comparison). These data demonstrate that the sex skew assay reported reproducible X skew from 9-27 ng input genomic DNA.

Assay precision is determined by calculating X skew in repeat measures for genomic template from sex skewed straws representing n=20 sires. FIG. 2 plots the calculated % X from quadruplicate assays for each straw batch (each straw batch consists of multiple straws of sexed semen from a single ejaculate). The average standard deviation in repeat measures is 0.5 percentage points, demonstrating that under these conditions, the ddPCR sex skew assay reports the X skew 0.5%, making the assay the most precise measurement of sex skew currently available.

To date, the ddPCR sex skew assay has been used to quantify the percentage of X chromosome-containing cells in sexed semen from 7 angus, 14 Brown Swiss, 2 HP, 80 Jersey, and 280 Holstein sires (data not shown), demonstrating the assay is insensitive to background genetic variation.

Example 7: Autosomal Reporter, GAPDH, Confirms Total Cells Interrogated

Figure 15:
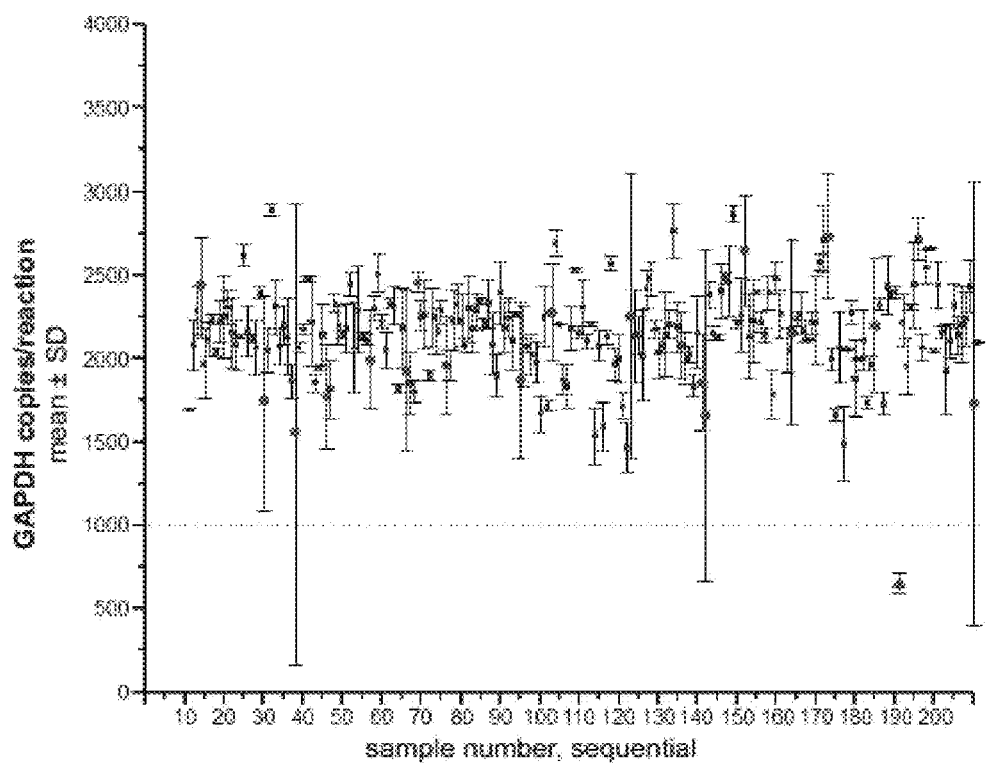
FIG. 15 shows variance and absolute GAPDH copy counts verified sex skew ddPCR assay accuracy, flagging samples for retest when they fall outside acceptable ranges. Scatter plot of GAPDH copies per well from replicate sex skew ddPCR assays representing n=220 unique sexed semen straw batches identified samples which fall into three categories: filled black squares represent samples meeting assay requirements of interrogating at least 1000 cells per well and variance between duplicate wells less than 2SDs for the assay, open circles represent samples which interrogated a sufficient number of cells, but exhibited variance between duplicate wells which was greater than 2SDs for the assay, and filled triangles represent samples which exhibited acceptable variance but did not interrogate a sufficient number of cells. Out of the 220 samples assayed, 16 failed to meet assay criteria the first time they are tested, providing an initial assay retest rate of 7.3%.

Implementing a sex skew assay as a quality control measure requires minimal assay variance, but also the built-in confirmation of assay robustness. The data in FIG. 12A demonstrates the % X has the lowest variance when assay is calculated as a function of X/(X+Y) copies. The quality of the data, however, depend upon the total number of cells interrogated, as well as the variance between duplicate wells, which can be artificially elevated by random and systematic errors such as can occur during pipetting. To increase assay robustness and decrease error, DNA is obtained from at least 1000 cells per assay replicate (where the assay is performed in duplicate) as well as acceptable assay variance in repeat measures. The number of autosomal (GAPDH) copies quantified is required to be equal (X+Y) within assay variance, with less than 10% variance in absolute copy counts between replicates. FIG. 15 presents total GAPDH counts from duplicate reactions as mean SD for n=220 unique sex skewed straw batches. Samples meeting both the minimum interrogation threshold and variance criteria are demarcated with a filled square. Sample which meet count criteria but exhibit variance outside the acceptable range are demarcated with open circles, where samples failing to meet total interrogated cell criteria are marked with filled triangles. Samples which fail to meet stringent assay requirements require re-testing in order to meet validation criteria.

Figure 16:
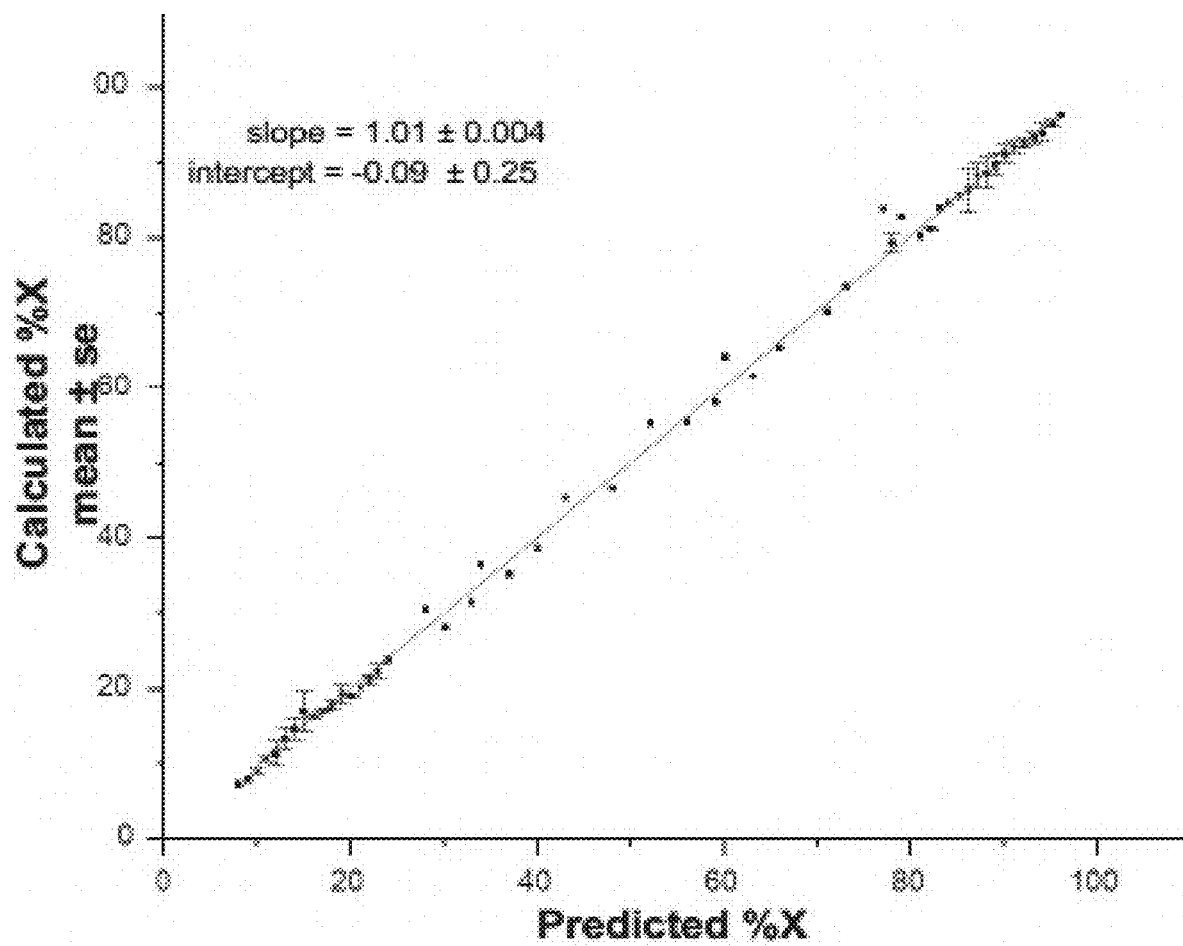
FIG. 16 shows graph plots of predicted % X vs. calculated % X from the ddPCR sex skew assay from n=6 experiments which mixed known high X skew with known high Y skew genomic bovine DNA to create a stepwise dose-response curve. DNA samples represented n=12 different bulls. Linear fit slope=1.01±0.04.

Example 8: ddPCR Sex Skew Assay Demonstrated Linear Dynamic Range for Stepwise X/Y Dose-Response The precision and accuracy of the sex skew assay is demonstrated in repeat measures of genomic DNA from conventional (non-sexed) bovine semen straws. To examine the precision of the assay across a range of sex skews (varying the expected % X), genomic DNA template from samples of known X or Y skew (where starting skew is >90% X or Y, respectively) are mixed in a dose-response manner to span 10-95% X. FIG. 16 plots the predicted vs. calculated % X from n=5 dose-response template mixtures (representing a total of 10 sires). These data reveal a linear fit with a slope of 1.01±0.004, and demonstrate that even at very low X amplicon counts (where skew is 10% X, 90% Y), the assay provides accurate skew quantification.

Figure 17:
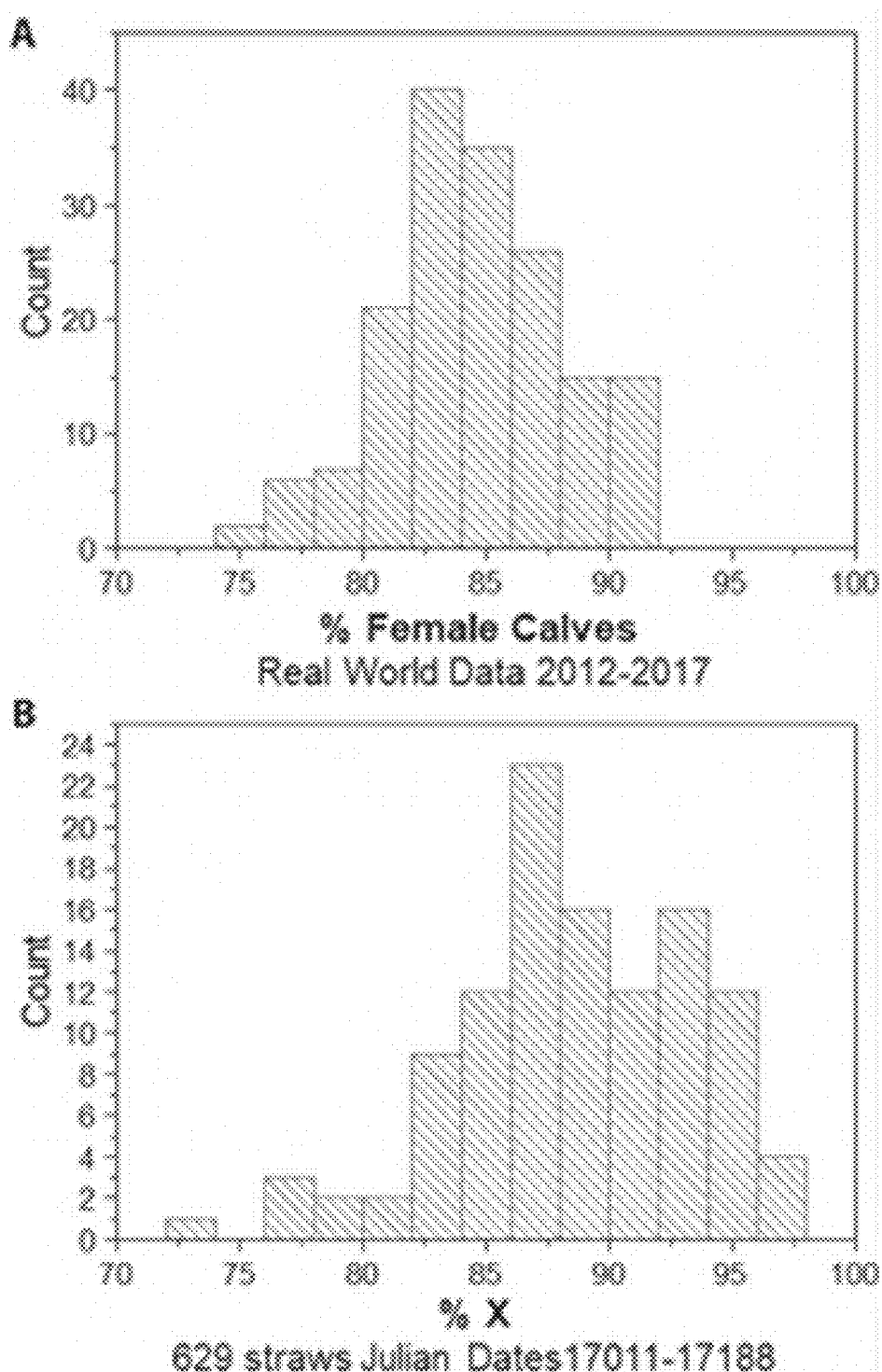
FIG. 17 (A.) Histogram depicts the percentage of female calves born from sexed-semen inseminations from 2012-2017, with mean=84.0% female calves, minimum=74%, maximum=91%. (B.) Histogram depicts % X chromosome sperm in commercial sexed semen straws spanning (17011-17188) from n=115 straw batches, with mean=88.6% X chromosome, minimum=72.7%, maximum=96.5%. Data demonstrate the sex skew assay results correspond with the historical distribution of female calves born from sexed semen inseminations.

Example 9: ddPCR Sex Skew Assay Reflects Historical Female Calves Resulting from Sexed Semen Inseminations To confirm whether the X skew data reflect the customer experience, sex skew is quantified from commercially available 529 Sexation® sexed semen from 2017 and compared to the historical customer experience of female calves born from sexed semen artificial inseminations from 2012-2017. FIG. 17A plots the distribution of female calves born from 2012-2017 from inseminations using sexed semen from the Real World Database (mean=84.0% female calves, n=168 records where each record represents data from 1 sire from all farms reporting >100 births for that sire from a total of 294,732 birth records). FIG. 17B plots the histogram of the sex skew from commercial 629 sexed semen as reported by the ddPCR assay (mean=88.6% X chromosome, n=115, representing 63 Holstein, 52 Jersey 629 straw batches dating 17011-17118). While the data do not represent paired sampling, the histograms confirms the ddPCR sex skew assay of commercially available sexed bovine semen generally reflected the historical customer experience of female calves born.

What is claimed is:

1. A system for assessing the sex-skew in a population of cells, comprising:
a first oligonucleotide agent that selectively binds to an X-chromosome nucleic acid sequence comprising at least one sequence selected from the group consisting of SEQ ID NO: 4-6, 28-35, 222, and 845-847; and
a second oligonucleotide agent that selectively binds to a Y-chromosome nucleic acid sequence comprising at least one sequence selected from the group consisting of SEQ ID: 7-9, 36-55, 767, 850-861, and 864-875.

2. The system of claim 1, further comprising a third oligonucleotide agent that selectively binds to an autosomal chromosome nucleic acid sequence.

3. The system of claim 1, wherein:
said first nucleotide agent comprises oligonucleotide primer sequences SEQ ID NOs: 4 and 5, and oligonucleotide probe sequence SEQ ID NO: 6; and
said second nucleotide agent comprises oligonucleotide primer sequences SEQ ID NOs: 7 and 8, and oligonucleotide probe sequence SEQ ID NO: 9.

4. The system of claim 3, further comprising a third nucleotide agent comprising oligonucleotide primer sequences SEQ ID NOs: 1 and 2, and oligonucleotide probe sequence SEQ ID NO: 3.

5. The system of claim 1, further comprising reagents and buffers for removing non-viable sperm cells.

6. The system of claim 1, further comprising reagents and buffers for isolating DNA from a sample of sperm cells.

7. The system of claim 1, wherein the oligonucleotide agent is contained in an oligo-chip.

8. The system of claim 1, wherein the oligonucleotide agent comprises a detectable label.

9. The system of claim 8, wherein the detectable label is selected from the group consisting of a fluorochrome and a radioactive isotope.

10. The system of claim 8, wherein the detectable label is selected from the group consisting of fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE),6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), $^{32}$P, $^{35}$S, and $^{3}$H.

11. The system of claim 1, wherein the system further comprises a droplet generator and a droplet reader.

12. The system of claim 1, wherein the system further comprises a cytometer.

13. The system of claim 1, further comprising dNTPs and polymerase enzymes.

14. A method of assessing sex-skew in a population of sperm cells, the method comprising steps of:
    detecting binding of a set of oligonucleotide agents to sperm DNA obtained from a sample of sperm cells, wherein the set includes:
    a first oligonucleotide agent that selectively binds to an X-chromosome nucleic acid sequence comprising at least one sequence selected from the group consisting of SEQ ID NO: 4-6, 28-35, 222, and 845-847; and
    a second oligonucleotide agent that selectively binds to a Y-chromosome nucleic acid sequence comprising at least one sequence selected from the group consisting of SEQ ID: 7-9, 36-55, 767, 850-861, and 864-875.

15. The method of claim 14, further comprising isolating sperm DNA from a population of sperm cells from a semen sample.

16. The method of claim 15, further comprising removing laser ablated sperm cells from said semen sample of sperm cells prior to said isolating sperm DNA.

17. The method of claim 1, wherein said population of cells comprise an X-skewed sperm population.

18. The method of claim 14, wherein said step of detecting comprises amplifying at least one of an X-chromosome target site and a Y-chromosome target site.

19. The method of claim 15, wherein said semen sample is from *Bos taurus, Bos indicus, Bos bubalis*, or hybrids thereof.

20. The method of claim 14, wherein said detecting comprises performing multiplex ddPCR.

* * * * *